(12) United States Patent
Gross et al.

(10) Patent No.: US 12,108,713 B1
(45) Date of Patent: Oct. 8, 2024

(54) ALGAE SYSTEM FOR WATER TREATMENT, BIOENERGY PRODUCTION, AND RESOURCE REUSE

(71) Applicant: Gross-Wen Technologies, Inc., Slater, IA (US)

(72) Inventors: Martin Gross, Boone, IA (US); Joseph Edward Zuback, Camarillo, CA (US); Paul Simpson, Harlan, IA (US)

(73) Assignee: Gross-Wen Technologies, Inc., Ames, IA (US)

( * ) Notice: Subject to any disclaimer, the term of this patent is extended or adjusted under 35 U.S.C. 154(b) by 51 days.

(21) Appl. No.: 18/121,800

(22) Filed: Mar. 15, 2023

Related U.S. Application Data

(60) Provisional application No. 63/438,995, filed on Jan. 13, 2023.

(51) Int. Cl.
| | | |
|---|---|---|
| *A01G 33/00* | (2006.01) | |
| *C12M 1/00* | (2006.01) | |
| *C12M 1/26* | (2006.01) | |
| *C12M 3/00* | (2006.01) | |

(52) U.S. Cl.
CPC ............. *A01G 33/00* (2013.01); *C12M 21/02* (2013.01); *C12M 23/26* (2013.01); *C12M 23/34* (2013.01); *C12M 23/48* (2013.01); *C12M 23/50* (2013.01); *C12M 29/00* (2013.01); *C12M 33/18* (2013.01)

(58) Field of Classification Search
CPC ........ A01G 33/00; A01G 31/00; A01H 4/001; C12M 33/18
See application file for complete search history.

(56) References Cited

U.S. PATENT DOCUMENTS

| | | | |
|---|---|---|---|
| 11,339,070 B2 | 5/2022 | Gross et al. | |
| 2008/0155890 A1* | 7/2008 | Oyler | C12M 23/38 47/1.4 |
| 2010/0018214 A1 | 1/2010 | Katchanov | |
| 2010/0224574 A1* | 9/2010 | Youngs | B01D 33/646 210/780 |
| 2010/0236164 A1 | 9/2010 | Chuang et al. | |

(Continued)

FOREIGN PATENT DOCUMENTS

| | | |
|---|---|---|
| CN | 103283582 | 9/2013 |
| CN | 204491563 | 7/2015 |

(Continued)

OTHER PUBLICATIONS

International Search Report and Written Opinion for PCT/US2023/064433 dated Aug. 17, 2023, 10 pages.

*Primary Examiner* — Kristen C Hayes
(74) *Attorney, Agent, or Firm* — Frost Brown Todd LLP; Vance V. VanDrake, III; Alexander J. Johnson

(57) ABSTRACT

The present disclosure teaches an algal growth system. The algal growth system includes a flexible sheet material, a liquid reservoir, a mechanism to rotate the flexible sheet material, a resource reclamation device, and an enclosure. The flexible sheet material facilitates growth of a biofilm. The liquid reservoir is configured to retain a contacting liquid in contact with the flexible sheet material and the mechanism rotates the flexible sheet material through the contacting liquid. The resource reclamation device associated with the enclosure is configured to collect and provide a resource for reuse.

16 Claims, 35 Drawing Sheets

(56) References Cited

U.S. PATENT DOCUMENTS

| | | | |
|---|---|---|---|
| 2012/0294788 A1* | 11/2012 | Walsh, Jr. | C12M 23/18 |
| | | | 423/225 |
| 2014/0315291 A1* | 10/2014 | Higgs | C12M 41/10 |
| | | | 435/292.1 |
| 2020/0048122 A1* | 2/2020 | Gross | C02F 3/322 |
| 2020/0231477 A1* | 7/2020 | Wen | C12N 1/12 |
| 2020/0308519 A1 | 10/2020 | Gross et al. | |
| 2021/0292201 A1* | 9/2021 | Gross | C02F 3/006 |

FOREIGN PATENT DOCUMENTS

| | | | | |
|---|---|---|---|---|
| CN | 109601200 | | 4/2019 | |
| DE | 3234348 | A1 * | 3/1984 | |
| GB | 1509630 | A * | 5/1978 | A01G 33/00 |

* cited by examiner

ALGAE SYSTEM FOR WATER TREATMENT, BIOENERGY PRODUCTION, AND RESOURCE REUSE

CROSS REFERENCE TO RELATED APPLICATION

This application claims the benefit of U.S. Provisional Application No. 63/438,995 filed Jan. 13, 2023, the disclosures of which are hereby incorporated herein by reference in its entirety.

TECHNICAL FIELD

Embodiments of the present disclosure relate, in general, to biofilm technology, and in particular to a revolving algal biofilm (RAB) photobioreactors for stimulating algal growth and simplified biomass harvesting. More specific embodiments of the present disclosure relate to a RAB photobioreactor that operates to capture water and other resources produced within an enclosure surrounding the photobioreactor for reuse.

BACKGROUND

There is a rising demand for improvements in wastewater treatment technology due to the decreasing availability of freshwater resources and requirements for higher quality water treatment processes across many industrial sectors. The treatment of wastewaters is a major problem today. Currently, municipal and industrial treatment facilities do not have an effective technology for reducing pollutants in their discharged effluents, especially phosphorous. Different states have implemented or are currently implementing various phosphorous discharge limits for municipal and industrial wastewater effluents in compliance with the US EPA National Nutrient Strategy (US EPA, 2008a).

Existing technologies are available for pollutant removal from municipal and industrial wastewaters. However, those technologies are not cost-effective or environmentally friendly. For example, the chemical-based method for pollutant removal is expensive due to the large amount of chemicals (e.g., aluminum and magnesium salts) used. Additionally, the chemical removal of pollutants from wastewaters will result in metal-containing sludge which results in a disposal problem.

It has recently been discovered that a microorganism growing apparatus growing microorganisms, including, but not limited to, bacteria, fungi, and/or algae, can be used to remove contaminants or pollutants from a fluid. Microorganism growing apparatuses, such as revolving algal biofilm (RAB) photobioreactors naturally evaporate water and produce other tangible resources. However, in most instances, that evaporating water is typically lost to the surrounding atmosphere and the other tangible resources are not collected. Therefore, there is a need in the art for a process that can collect the evaporating water and tangible resources for beneficial reuse.

BRIEF DESCRIPTION OF THE DRAWINGS

Various embodiments will become better understood with regard to the following description, appended claims and accompanying drawings wherein:

DETAILED DESCRIPTION

Figure 1:
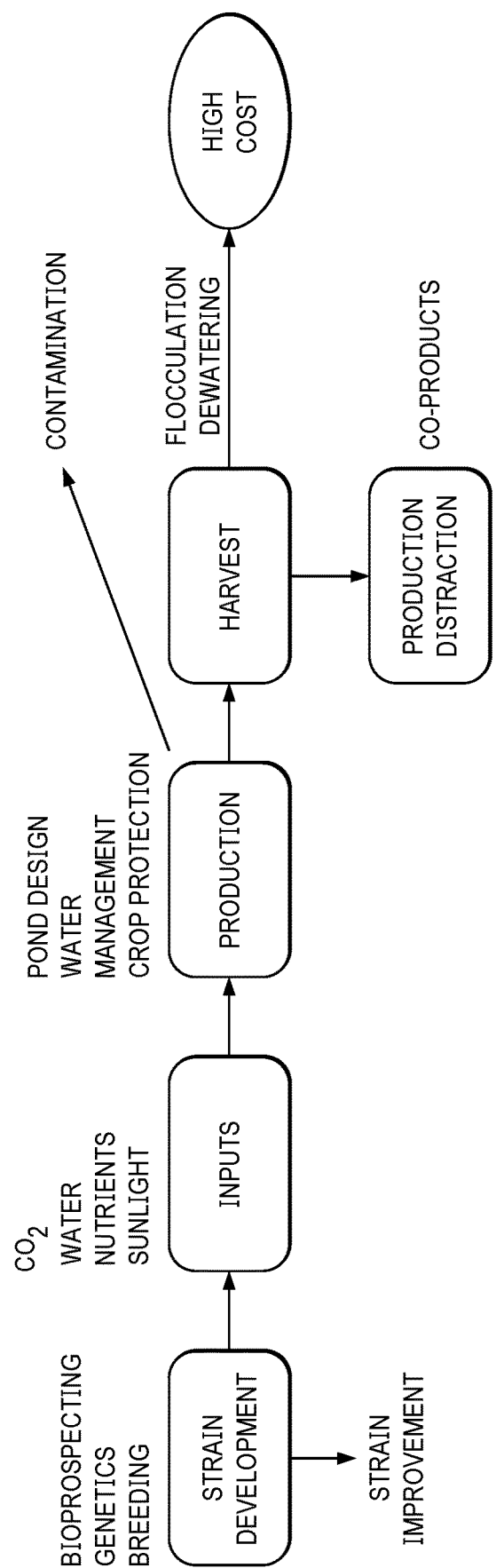
FIG. 1 depicts a flow chart illustrating the methodology generally associated with algae harvesting.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings, wherein like numbers indicate the same or corresponding elements throughout the views. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems, and methods described herein. None of the features or components shown in the drawings or discussed below should be taken as mandatory for any specific implementation of any of these the apparatuses, devices, systems, or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, it should be understood that unless otherwise specified or required by context, any explicit or implicit ordering of steps performed in the execution of a method does not imply that those steps must be performed in the order presented but instead may be performed in a different order or in parallel.

Revolving Algal Biofilm Photobioreactors

Traditionally, algae are grown in open raceway ponds or enclosed photobioreactors, where algae cells are in suspension and are harvested through sedimentation, filtration, or centrifugation. Due to the problem caused by light penetration by mutual shading of suspended algal cells, algal growth in suspension is often limited by light availability. Also, due to the small size (3-30 µm) of algae cells and the dilute algae concentration (<1% w/v), gravity sedimentation of suspended cells often takes a long time in a large footprint settling pond. Filtration of algal cells from the culture broth can result in filter fouling. Centrifugation can achieve high harvest efficiency; however, the capital investment and operational cost for a centrifugation system can be prohibitively expensive. Many of these systems naturally produce a large amount of water and other resources, however, these methods do not incorporate means to utilize the produced water and resources. In most instances, the water produced is much cleaner than any water input into the system to get the processes started. However, the water is usually not collected, and is just syphoned off into the surrounding environment. Due to these drawbacks, an alternative method for growing and harvesting algae biomass and capturing water and other resources produced by the growing process may be advantageous.

Described herein are example embodiments of revolving algal biofilm photobioreactor systems and methods that can not only enhance cell growth and simplify biomass harvesting, but can also capture water and other resources produced by the system and methods for reuse. In one example embodiment, systems and methods can provide cost effective harvesting of algae biomass while also capturing water and other resources produced by the system and methods for reuse. In some embodiments, systems and methods can be used to produce algae for biofuel feedstock, aquacultural feed, and nutraceuticals while also capturing water and other resources produced by the system and methods for reuse. In some embodiments, algal cells can be attached to a material that can be rotated between a nutrient-rich liquid phase and a carbon dioxide rich gaseous phase such that alternative absorption of nutrients and carbon dioxide can occur while also capturing water and other resources produced by the system and methods for reuse. The algal cells can be harvested by scraping from the surface to which they are attached, which can eliminate harvest procedures commonly used in suspension cultivation systems, such as sedimentation, flocculation, floatation, and/or centrifugation and the water and other resources can be captured by a resource reclamation device located on a top portion of the system enclosure. It will be appreciated that systems and methods described herein can be combined with sedimentation, centrifugation, or any other suitable processes.

Example embodiments described herein can mitigate air and water pollution while delivering high value bio-based products such as bio-fuels, nutraceuticals, and animal feeds from microalgae. Example embodiments described herein can also capture and reuse resources produced during the cultivation process such as water, CO2, heated air, and electricity produced utilizing renewable fuels produced from the cultivation process. The captured resources can be reused within the system itself, or the resources can be packaged and utilized for other purposes. Example embodiments of RAB technology can play a beneficial role in creating an algal culture system that can economically produce algae biomass for, for example, biofuels, nutraceuticals, and animal feeds. Microalgae may have a significant impact in the renewable transportation fuels sector. Example embodiments can grow microalgae that can be used in biofuel production with a low harvest cost. Algae, if produced economically, may also serve as a primary feed source for nutraceuticals and aqua feeds production.

Example systems and methods can include developing a biofilm-based microalgae cultivation system (RAB) that could be widely adapted by the microalgae industry for producing, for example, fuels and high value products, as well as for treating municipal, industrial, and agricultural wastewater. Microalgae use photosynthesis to transform carbon dioxide and sunlight into energy. This energy is stored in the cell as oil, which has a high energy content. The oil yield from algae can be significantly higher than that from other oil crops. Algae oil can generally be easily converted to biodiesel and could replace traditional petroleum-based diesel. In addition to fuel production, microalgae have also been rigorously researched for the potential to produce various high value products such as animal feed, omega-3 polyunsaturated fatty acids, pigments, and glycoproteins. The resources captured from the RAB system can also be continuously recycled back through the RAB system itself to create a more efficient, economical, and green system. If systems of the present disclosure are utilized to treat municipal, industrial, and agricultural wastewater, the water captured in systems of the present disclosure will be cleaner than the wastewater that entered the system, and can therefore safely be used in reuse applications.

Referring to FIG. 1, low biomass productivity and high cost of algae production can still be the major limitation in industrial scale operations. Example embodiments described herein may minimize such costs associated with the growth and harvesting of algal cells from an aqueous culture system through, amongst other sources, the capture and reuse of resources produced during the growth process.

Generally, algae cultivation is done using suspended algae culture. This culture method can have drawbacks including low biomass yield and productivity and low efficiency of harvesting the algal cells from liquid culture medium.

Figure 3:
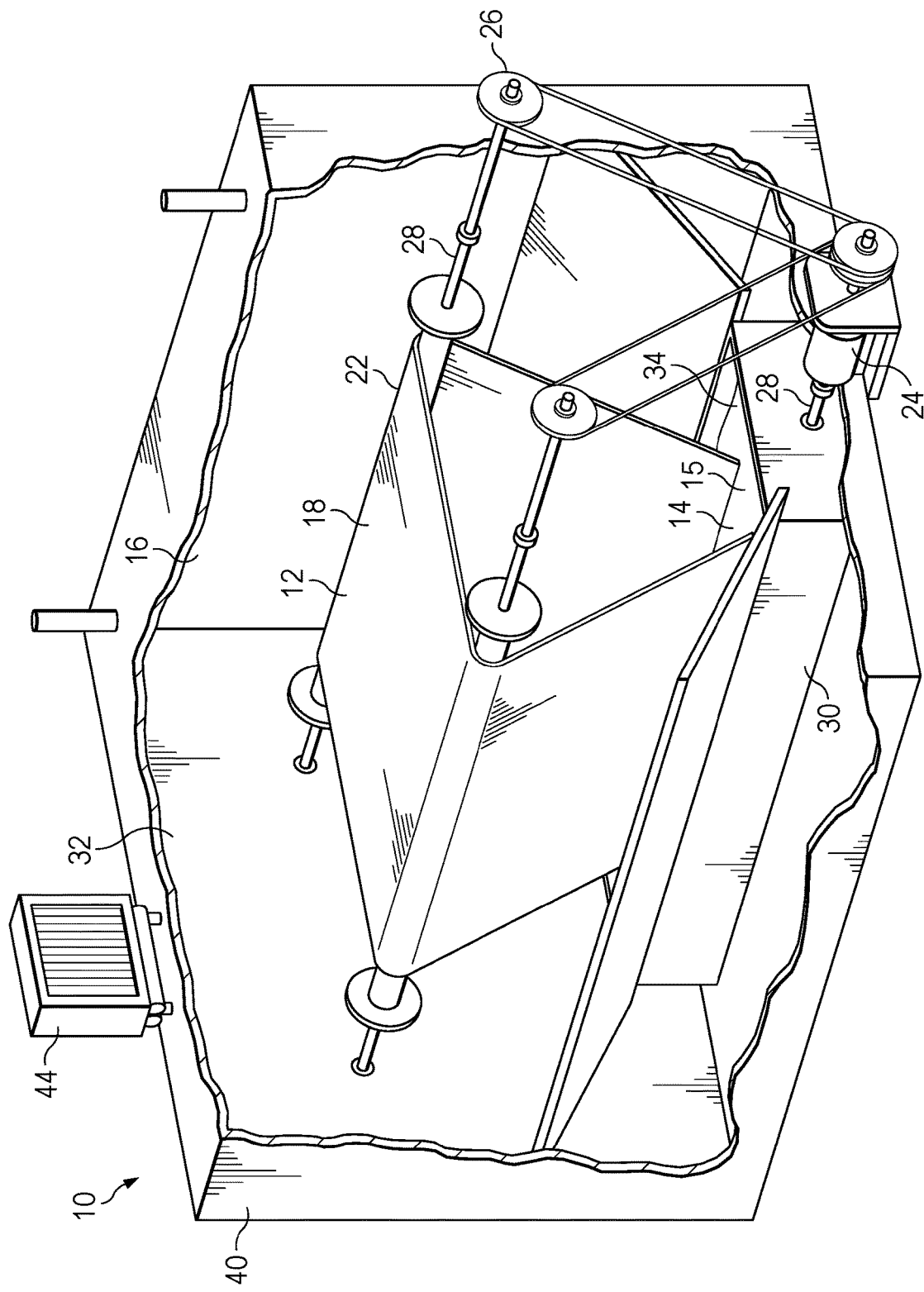
FIG. 3 depicts a partial cutaway perspective view of a revolving algal biofilm photobioreactor with a resource reclamation device on a top portion thereof according to one embodiment.
Figure 4:
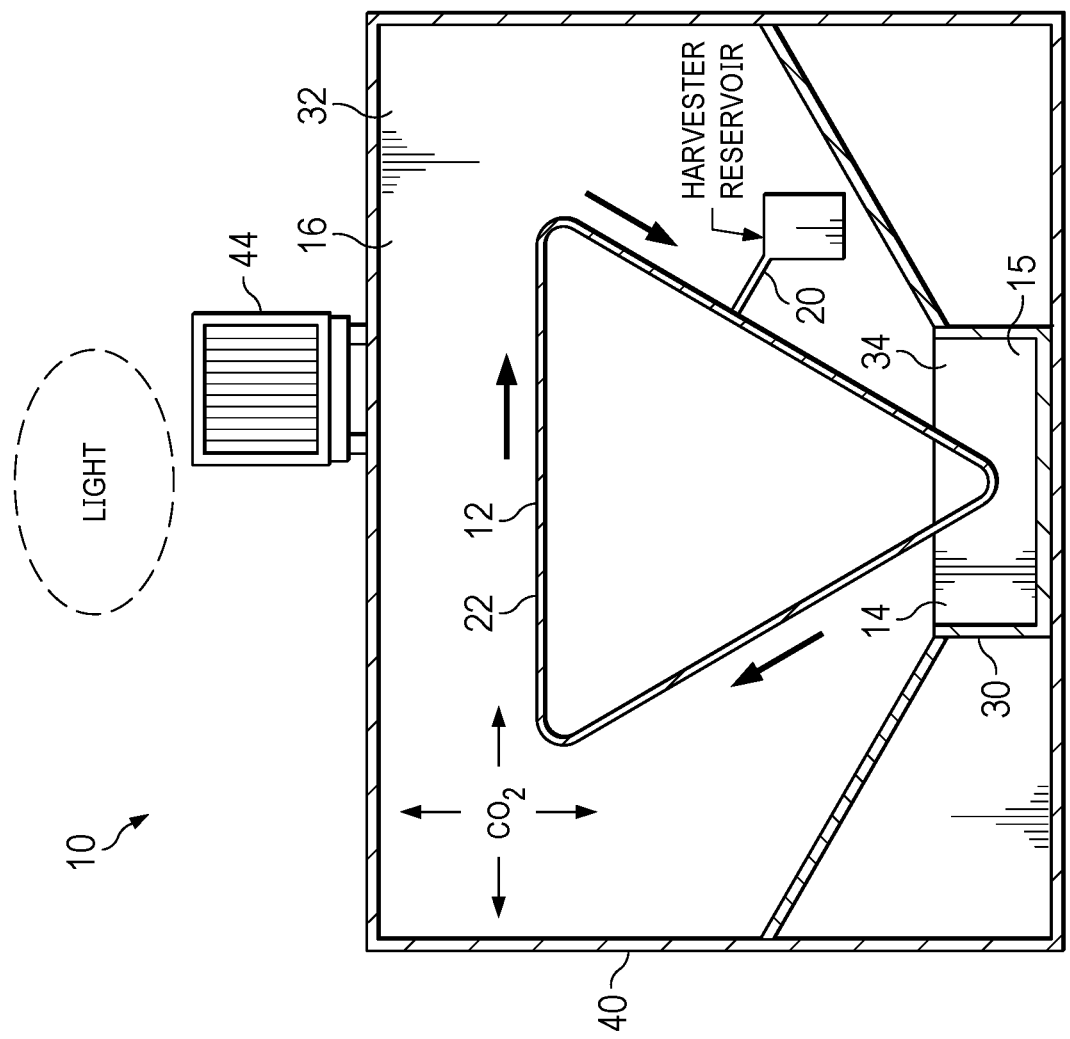
FIG. 4 depicts a schematic front view of the revolving algal biofilm photobioreactor with a resource reclamation device on a top portion thereof illustrated in FIG. 3.

Example embodiments described herein can promote a fast cell growth and a simple economical harvesting method that may be an improvement over existing methods. Example embodiments can include an algal growth system or mechanized harvesting system, which can remove concentrated algae in-situ from an attachment material and can minimize the amount of de-watering needed post-harvest. Example embodiments can optimize gas mass transfer due to the algae cells coming in direct contact with gaseous carbon dioxide when the algae is rotated through the open air. In example embodiments of the present disclosure, the algae is rotated within an enclosure, such as greenhouse 40 as shown in FIGS. 3 and 4 having an increased carbon dioxide concentration relative to the atmosphere, which may improve the growth rate of the algae. Greenhouse 40 also acts a natural apparatus to assist in the capture of evaporated water produced by the growing process. In one or more embodiments, a resource reclamation device 44 is located on a top portion of the greenhouse 40 to assist in the recapture of the resources produced during the growing process. Although the Figures in the present disclosure show a resource reclamation device, such as device 44, located on the exterior upper surface of the enclosure, such as greenhouse 40, it is also contemplated that the resource reclamation device, such as device 44, can be located on an interior upper surface of the enclosure, along the exterior side surfaces of the enclosure, or along the interior side surfaces of the enclosure.

In one or more embodiments of the present disclosure, the size of the enclosure, such as greenhouse 40 is not a limiting feature. However, it is envisioned that the enclosure would be small enough to only surround the RAB system contained within the enclosure. This would not allow the evaporated gas produced from the RAB to escape far from the RAB and into the environment between the RAB and the walls of the enclosure where the resource reclamation device would be located.

In one or more embodiments, the temperature maintained within the enclosure is not a limiting feature. However, it is envisioned that the enclosure could be operated at a temperature that is too high for people to be safely inside. As such, in some embodiments it may be necessary to utilize an optional fan that could be controlled such that it turns on when a human needs to enter the greenhouse to operate on the RAB system contained within the greenhouse. Having the greenhouse designed with limited access points will likely also enhance the amount of CO2 produced by the RAB system, which is a resource that could be collected by a resource reclamation device.

In one or more embodiments, the resource reclamation device 44 is selected from the group consisting of a condenser, a heat exchanger, an air-conditioning compressor, or a chiller. A condenser is considered to be any device that converts water vapor to liquid water. In most instances, this is done by reducing the water temperature (and sometimes pressure) below its dew point. Condensing liquid is about creating a temperature differential between a solid surface and a gas that contains air. Air located within enclosures of the present disclosure is air that contains the water vapor that the present disclosure is looking to capture. That temperature of the air within the enclosures of the present disclosure will be different than either the water temperature or the outside air temperature. This delta in temperature will be the driving force of the system utilized to capture water vapor from the atmosphere within the enclosures of the present disclosure. For example, often at night, the temperature outside of the enclosures of the present disclosure will drop much faster than the air inside the enclosures. As such, the outside air can be pumped through a resource reclamation device, such as a condenser, to capture the water vapor within the air inside the enclosure. In another example, a cool influent water, such as seawater, could be used to cool the condenser and capture the water vapor within the air inside the enclosure.

An air-conditioning compressor will remove water vapor within the air inside the enclosure when said air has a high humidity. A chiller will allow for the air from within the enclosure to flow through it with a refrigerant on the other side of the surface to remove water vapor within the air inside the enclosure.

In one or more embodiments, the resource reclamation device 44 can either be running at all times, or can be run at select intervals. The intervals could be determined on the level of humidity reached within greenhouse 40 or when the temperature difference between the interior of the greenhouse 40 and the exterior environment reaches a certain threshold.

In one or more embodiments, the resource reclamation device 44 can be powered from AC supplied via a grid, or through AC/DC power supplied via a renewable energy source, such as solar power.

Figure 2:
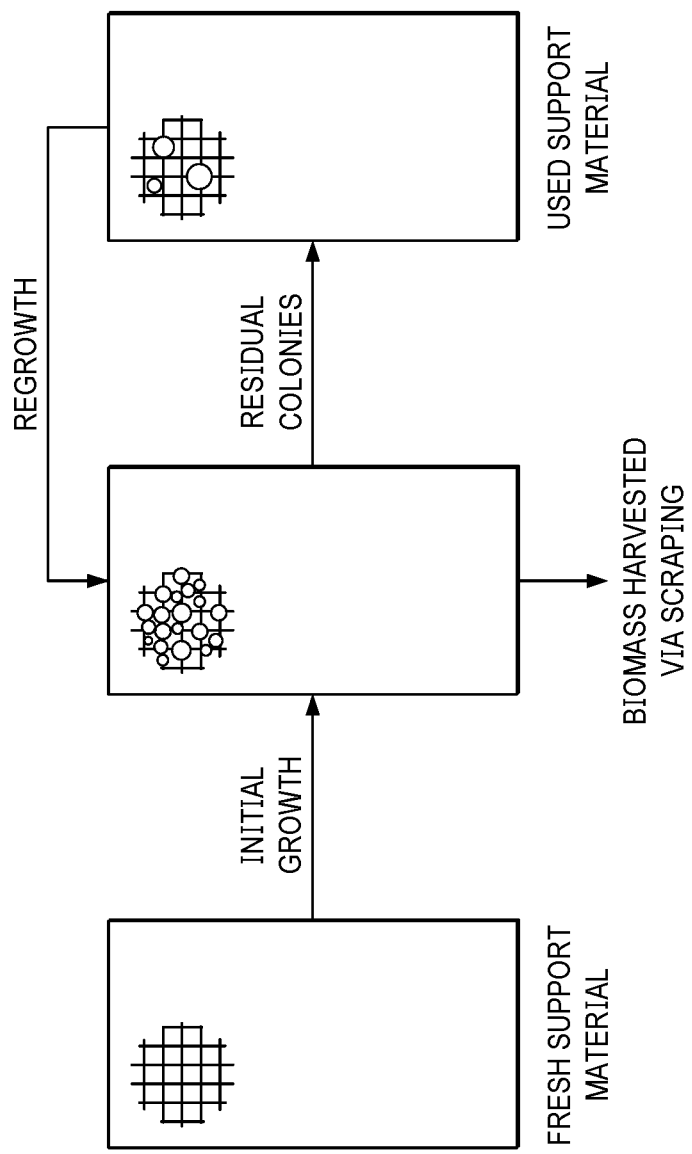
FIG. 2 depicts a top view of microalgae being grown on polystyrene foam.

Example embodiments can utilize minimal growth medium, where the triangular or vertical design of the RAB system in example embodiments may reduce the total water needed for the growth and the chemical costs of growth medium. Any algae growing system that creates a large surface area between the gas and liquid interface are included in the present disclosure. In one embodiment, such advantages may be accomplished by submerging only the lowest portion of a bioreactor, supporting material, algal growth system, or mechanized harvesting system into the medium. Referring to FIG. 2, microalgae can be grown on the surface of polystyrene foam. FIG. 2 illustrates how algae can be harvested by scraping the surface of the foam. The mechanical separation through scraping of biomass from the attached materials can result in biomass with water content similar to centrifuged samples (e.g., 80-95% water content) and the residual biomass left on the surface can serve as an ideal inoculum for subsequent growth cycles.

Referring to FIGS. 3, 4, 7, and 8, an example embodiment of a revolving algal biofilm photobioreactor (RAB) 10, in which algal cells 18 can be attached to a solid surface of a supporting material 12, is disclosed. Although the supporting material is shown as being triangle-shaped, any shaped supporting material 12 is contemplated by the present disclosure. The photobioreactor 10 can keep the algal cells 18 fixed in one place and can bring nutrients to the cells, rather than suspend the algae in a culture medium. As shown in FIGS. 3 and 4, algal cells can be attached to the supporting material 12 that is rotating between a nutrient-rich liquid phase 15 and a $CO_2$-rich gaseous phase 16 for alternative absorption of nutrients and carbon dioxide. By placing the photobioreactor 10 within greenhouse 40, the gaseous phase 16 will be rich in $CO_2$. The algal biomass can be harvested by scrapping the biomass from the attached surface with a harvesting squeegee 20 (FIG. 4) or other suitable device or system. In example embodiments, the naturally concentrated biofilm can be in-situ harvested during the culture process, rather than using an additional sedimentation or flocculation step for harvesting, for example. The culture can enhance the mass transfer by directly contacting algal cells with $CO_2$ molecules in gaseous phase 16, where traditional suspended culture systems have to rely on the diffusion of $CO_2$ molecules from a gaseous phase to a liquid phase, which may be limited by a low gas-liquid mass transfer rate.

In one or more embodiments, the supporting material 12 has a height, which can be considered to be the distance between the uppermost point of the supporting material 12 while being utilized within the photobioreactor 10, and the lowermost point of the supporting material 12 while being utilized within the photobioreactor 10. In one or more embodiments, the height of the supporting material 12 is between 500 feet and 400 feet, in other embodiments between 400 and 300 feet, in other embodiments between 200 feet and 100 feet, in other embodiments between 100 feet and 50 feet, in other embodiments between 50 feet and 10 feet, and in yet other embodiments between 10 feet and 1 foot. In one or more embodiments, the maximum height of the supporting material 12 is 500 feet and the minimum height of the supporting material is 1 foot.

In one or more embodiments, only a certain percentage of the material of the supporting material 12 is placed within the nutrient-rich liquid phase 15 at one time. In one or more embodiments, between 20% and 18% of the material of the supporting material 12 is found within the nutrient-rich liquid phase 15, in other embodiments between 18% and 15%, in other embodiments between 15% and 10%, in other embodiments between 10% and 4%, in other embodiments between 4% and 1%, and in yet other embodiments between 1% and 0.1%. In one or more embodiments, the maximum percentage of the material of the supporting material that is placed within the nutrient-rich liquid phase is 20% and the minimum percentage is 0.1%. A higher-surface area of supporting material 12 that is outside of the nutrient-rich liquid phase 15 at one time equates to more evaporation within the overall system.

Example embodiments may only utilize a small amount of water by submerging the bottom of the algal growth system or mechanized harvesting system 22 in contacting liquid 14, while maximizing the surface are of the system outside of the liquid 14. It may be advantageous to maximize the surface area of the system that is exposed to the air to encourage evaporation. In some embodiments, the contacting liquid 14 can be replenished by utilization of resource water collected by the resource reclamation device 44. In these embodiments, plumbing or any other suitable mechanism can return the resource water back into the liquid reservoir 30. Example embodiments can be scaled up to an industrial scale because the system may have a simple structure and can be retrofit on existing raceway pond systems.

Example embodiments can be used in fresh water systems and can be adapted to saltwater culture systems. For example, embodiments of this system can be placed in the open ocean within a semi-permanent greenhouse enclosure with a resource reclamation device 44 on a top surface thereof, instead of in a raceway pond reactor. In this example application, the ocean can naturally supply the algae with sufficient sunlight, nutrients, water, and $CO_2$, which in turn may decrease operational costs.

Figure 7:
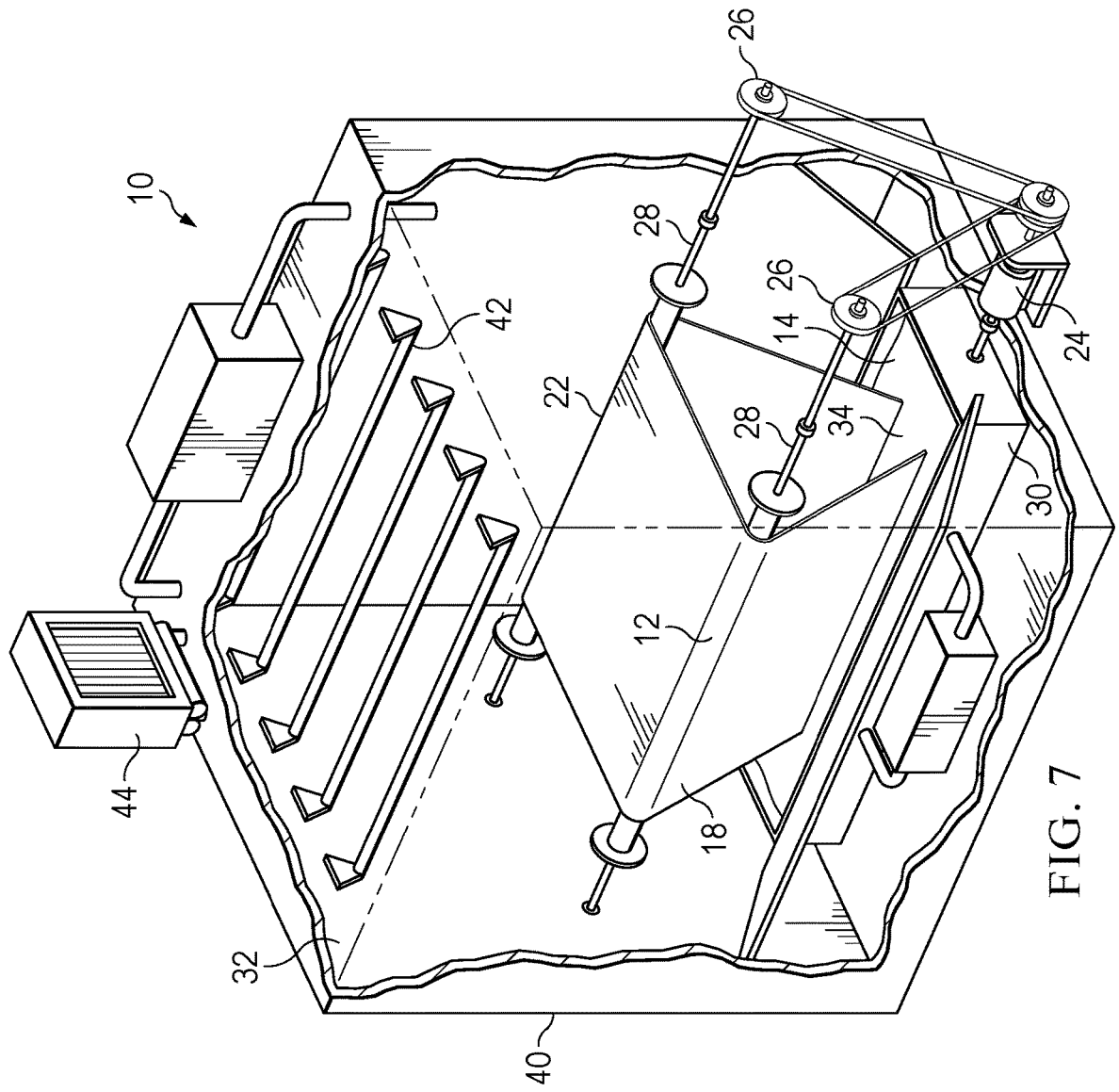
FIG. 7 depicts a partial cutaway perspective view of the revolving algal biofilm photobioreactor with a resource reclamation device on a top portion thereof illustrated in FIG. 3, shown with grow lights and a gas input.

Still referring to FIGS. 3, 4, 7, and 8, embodiments of the system can include a drive motor 24 and a gear system 26 that can rotate one or a plurality of drive shafts 28, where the one or a plurality of drive shafts 28 can correspondingly rotate the supporting material 12, such as a flexible sheet material. In one or more embodiments, the flexible sheet material is selected from the group consisting of cheesecloth, fiberglass, porous PTFE coated fiberglass, chamois, vermiculite, microfiber, synthetic chamois, burlap, cotton duck, velvet, poly-lactic acid, abraised poly-lactic acid, vinyl laminated nylon, polyester, wool, acrylic, lanolin, woolen, cashmere, leather, silk, lyocell, hemp fabric, polyurethane, olefin fibre, polylactide, carbon fiber, and a combination thereof. The supporting material 12 can be rotated into contact with the contacting liquid 14, which can allow the algal cells 18 to attach to the supporting material 12. The drive motor 24 can include a gear system 26 or pulley system that can drive the one or a plurality of drive shafts 28, where the one or a plurality of drive shafts 28 can rotate the supporting material 12 in and out of a contacting liquid 14, for example. Embodiments can also include a liquid reservoir 30, mister, water dripper, or any other suitable component or mechanism that can keep algae, which can be attached to the support material 12, moist. As stated above, the liquid reservoir 30 can be continuously supplied with water as a contacting liquid 14 by utilizing the water recaptured by the resource reclamation device 44. Embodiments can also include any suitable scraping system, vacuum system or mechanism for harvesting the algal cells 18 from the supporting material 12. It will be appreciated that the system can include one or a plurality of rollers (not shown) that can guide and support the supporting material 12 in addition to the one or a plurality of drive shafts 28. Referring to FIG. 7, grow lights 42 having any suitable wavelength can be provided in the system In an example embodiment, a generally triangle-shaped mechanized harvesting system 22 can be provided. Such a configuration can be beneficial in maximizing the amount of sunlight or light that algal cells 18 are exposed to. However versions of the system can be designed, for example, in any configuration that includes a "sunlight capture" part 32 which can be exposed to air and sunlight, and a "nutrient capture" part 34 which can be submerged into a nutrient solution or contacting liquid 14. It will be appreciated that, in a first position, the supporting material 12 can have a portion that is in the "sunlight capture" part 32 and a portion that is in the "nutrient capture" part 34, where rotation of the supporting material 12 to a second position can result in different regions of the supporting material 12 being in the "sunlight capture" part 32 and "nutrient capture" part 34. Such movement of the supporting material 12 can, for example, beneficially transition algal cells 18 from a nutrient rich liquid within the nutrient capture part 34 to the sunlight capture part 32 with sunlight and a carbon dioxide content higher than the outside atmosphere. As will be shown in more detail herein, a substantially vertical design is contemplated, which may be the simplest and most cost efficient design because such a system may minimize the amount of wasted space and may maximize the amount of algae produced in a small area by growing this system vertically. Alternative designs can include a straight vertical reactor, a reactor that is straight but slightly angled to provide more surface area for sunlight to hit, a cylindrical reactor, or a square shaped reactor.

Figure 8:
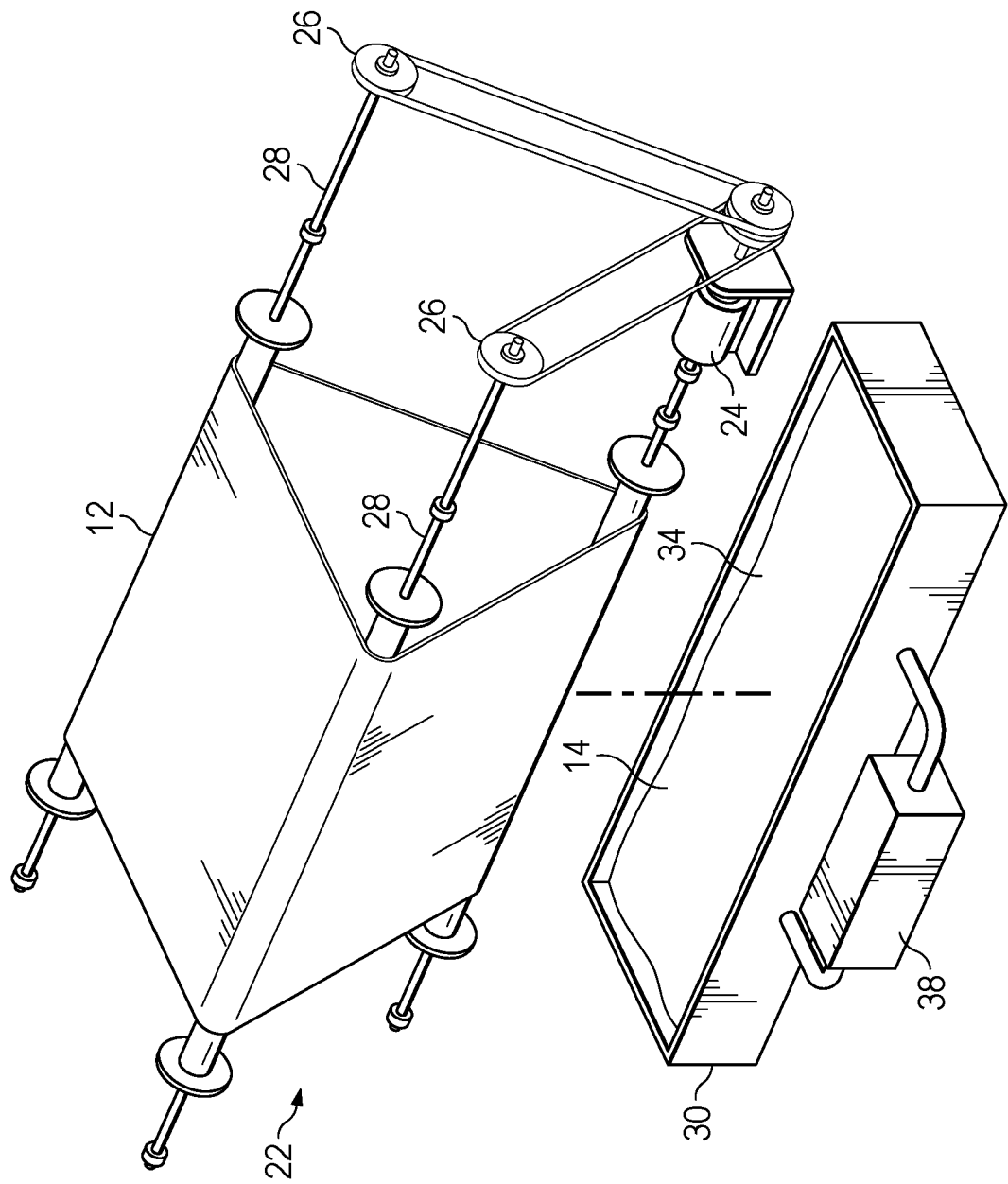
FIG. 8 depicts a partial exploded view of the algal growth system of the revolving algal biofilm bioreactor shown in FIG. 3.

Referring to FIG. 8, the generally triangle-shaped algal growth and mechanized harvesting system 22 can include a supporting material 12 that is movable or removable relative to the liquid reservoir 30. The supporting material 12, and any associated components such as the one or a plurality of drive shafts 28 and gear system 26, can be movable or removable for cleaning, replacement, harvesting, adjustment, or the like. It will be appreciated that such movement can be manual or can be automated if desirable. In an example embodiment, the liquid reservoir 30 can contain a contacting liquid 14 having a first chemical or fluid makeup, where the supporting material 12 can be lifted or otherwise transitioned from the liquid reservoir 30 into a second liquid reservoir (not shown) having a second liquid (not shown) having a different chemical or fluid makeup from the contacting liquid 14. In this manner, the supporting material 12 retaining algal cells 18 can be dipped or transitioned into a variety of fluids or materials that may maximize algal growth or otherwise provide a benefit. Such a system can be repeated or adjusted as appropriate. In an alternate embodiment, the supporting material 12 can be lifted or moved from the liquid reservoir 30 and transitioned to a harvesting station. In one embodiment, harvesting can take place while the supporting material 12 is positioned within the liquid reservoir 30

Still referring to FIG. 8, the liquid reservoir 30 can include a pump 38 or any other suitable actuator or fluid control. The pump 38 can circulate the contacting liquid 14, which may improve the growth of algal cells 18 and the efficiency of the overall system 10. It will be appreciated that the pump 38 can be an electric pump, a wheel, a paddlewheel, or can have any other suitable configuration to create any desirable flow pattern. It will be appreciated that the pump 38 can heat, cool, or otherwise adjust the conditions associated with the contacting liquid 14. The pump 38 can also be configured for the delivery of supplemental nutrients, such as supplemental fluids delivered at pre-specified times, where such delivery can be manual or automated.

It will be appreciated that the pump 38, and any other suitable components, can be associated with a computer, controller, or microcontroller that can be programmed to provide any suitable automated functionality. Numerous sensors may be associated with resources, such as water, $CO_2$, ammonia, heat, or the like, that are recycled or otherwise used by the system. Such sensors may communicate with a controller to provide detailed information on ecosystem conditions. The monitoring of such systems can be used by the computer, controller, or microcontroller to optimize the overall system for efficiency. For example, during a "night phase" various aspects of the system may go into a power down or sleep mode, followed by a "day phase" where these systems are powered up. A computer, controller, or microcontroller can alternate between direct power from solar, from a battery source, and/or an AC power source depending upon availability. A computer, controller, or microcontroller programmed with any suitable modes is contemplated.

Figure 5:
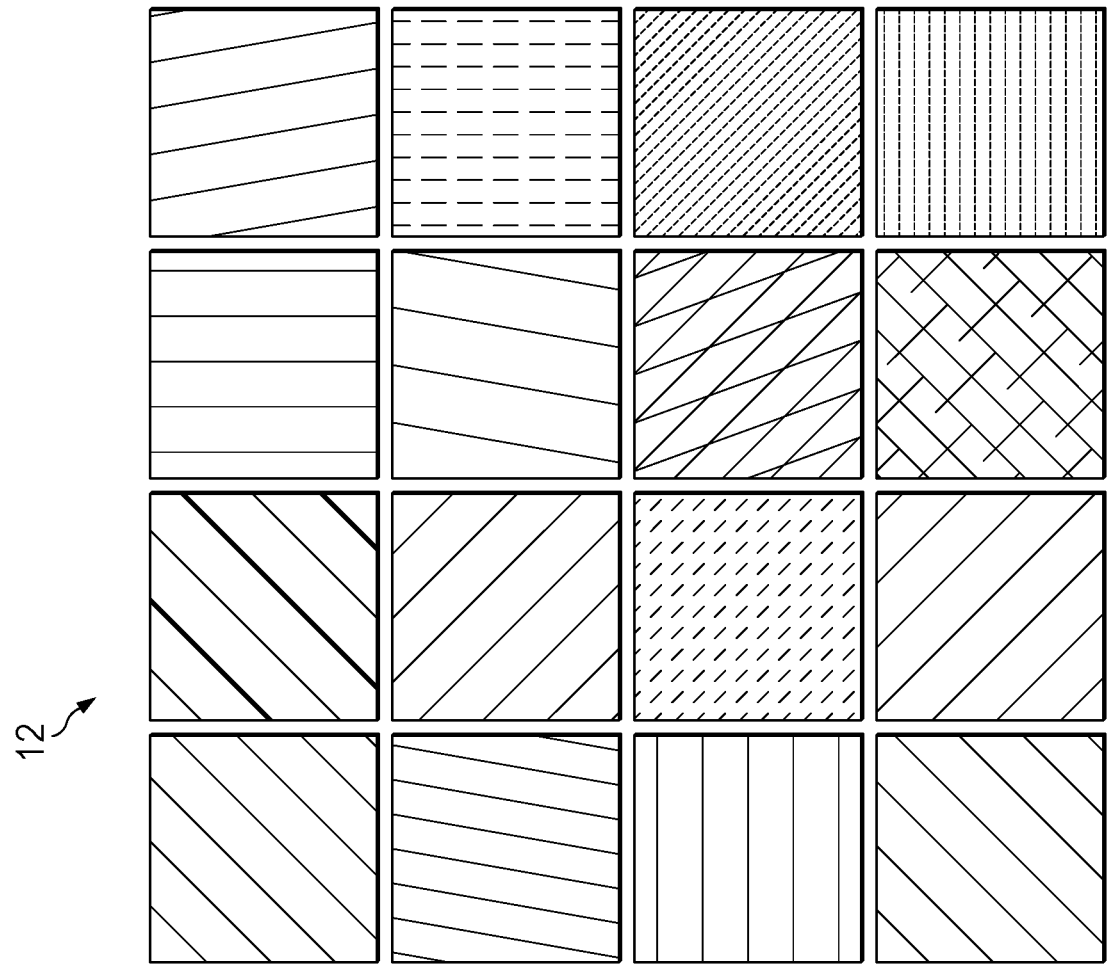
FIG. 5 depicts a top view of microalgae being grown on a variety of materials.

Referring to FIG. 5, any suitable supporting material 12, such as any suitable flexible fabric, can be used with the systems and methods described herein to grow any suitable material. For example, the microalga Chlorella, such as Chlorella vulgaris can be grown on materials such as, muslin cheesecloth, aramid fiberglass, porous PTFE coated fiberglass, chamois, vermiculite, microfiber, synthetic chamois, fiberglass, burlap, cotton duct, velvet, TYVEK, polylactic acid, abraised poly-lactic acid, vinyl laminated nylon, polyester, wool, acrylic, lanolin, woolen, cashmere, leather, silk, lyocell, hemp fabric, SPANDEX, polyurethane, olefin fiber, polylactide, LUREX, carbon fiber, and combinations thereof. The supporting material or associated material can include rubbers such as, for example, buna-n Rubber, butyl rubber, ECH rubber, EPDM rubber, gum rubber, polyethylene rubber, latex rubber, neoprene rubber, polyurethane, santoprene rubber, SBR rubber, silicone rubber, vinyl rubber, VITON fluoroelastomer, aflas, fuorosilicone, or combinations thereof. The supporting material or associated material can include plastics such as, for example, PETG, acrylic, cast acrylic, cellulose, polycarbonate, LDPE, PLA, PVC, ABS, polystyrene, HDPE, polypropylene, UHMW, delrin, acetal resin, nylon, cast nylon, CPVC, rexolite polystyrene, noryl PPO, polyester, PVDF, polysulfone, radel PPSU, ulrem PEI, FEP, PPS, PEEK, PFA, torlon PAI, reflon PTFE, polyimide, antistatic polycarbonate, antistatic cast acrylic, conductive ABS/PVC, antistatic acetal, atatic-dissipative UHMW, conductive UHMW, antistatic PTFE, glass-filled polycarbonate, strengthened acrylic, strengthened PVC, glass-filled nylon, glass-Filled acetal, glass-filled UHMW, glass-filled PTFE, and combinations thereof. The supporting material 12 and associated materials can include metals such as, for example, aluminum, steel, cast iron, tungsten carbide, tungsten alloy, stainless steel, nickel, titanium, copper, brass, bronze, lead, tin, zinc, casting alloys, or combinations thereof. Any suitable material for the supporting material 12 and associated materials is contemplated including ceramic, felt, fiberglass, foam, foam rubber, foam plastic, glass, leathers, carbon fiber, wire cloth, or the like.

Figure 18:
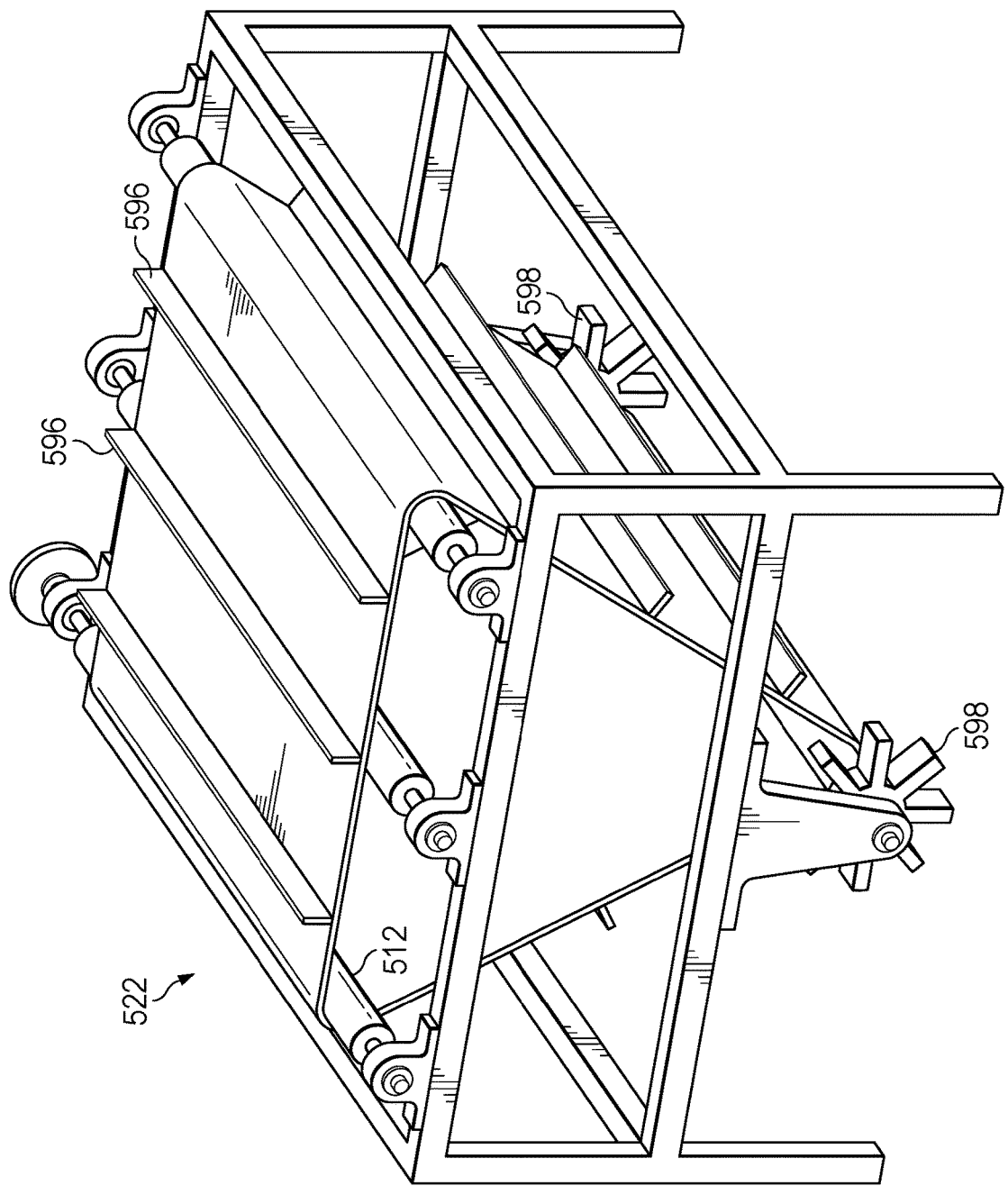
FIG. 18 depicts a perspective view of an algal growth system with a supporting material that includes a plurality of ribs according to one embodiment.

The material associated with the supporting material 12 can have a high surface roughness, high hydrophobicity, and high positive surface charge in one embodiment. It will be appreciated that any suitable texture, surface treatment, hybrid material, or the like is contemplated. The supporting material 12 can be in the form of a belt, sheet, or band which can be altered, modified, or changed with heat, abrasion, applying another material, chemically treating, applying a charged molecule, applying a polar molecule, or combinations thereof. Referring to FIG. 18, in one embodiment of an algal growth system 522, the supporting material 512 can include one or a plurality of ribs 596. The supporting material 512 can also be finned or otherwise textured such that a pump is not needed within the liquid reservoir (not shown) to agitate an associated contacting liquid (not shown), where rotation of the textured supporting material 512 can sufficiently agitate or otherwise create a desirable fluid dynamic.

The algal growth system 522 can also include an integrated paddle 598 that can be positioned within a contacting liquid with the liquid reservoir such that rotation of the textured supporting material 512 correspondingly can rotate the integrated paddle 598. In alternate embodiments, the textured supporting material 512 can include flexible regions and rigid regions, can be a hinged belt, can have removable sections, or can otherwise be suitably configured. Similar to greenhouse 40, the algal growth system 522 will also be contained within an enclosure (not shown), such as a greenhouse, to act as a natural apparatus to assist in the capture of resources produced by the growing process. In one or more embodiments, a resource reclamation device (not shown), similar to resource reclamation device 44, is located on a top portion of the greenhouse to assist in the recapture of the resources produced during the growing process.

For example, in one embodiment, strips of material can be attached to a rotating belt with a hook and loop fastener, where such strips can be pulled off of the rotating belt supporting material 12 during harvesting and replaced when harvesting is complete. The supporting material 12 utilized within embodiments of the algal growth system of the present disclosure can be reinforced by attaching a high strength and slowly degradable second layer of material to a cell growth material. The photobioreactors of the present disclosure can be configured such that the high strength material comes in contact with components such as rollers, drive shafts, and the like. Such a configuration may help avoid the wearing off of the cell growth material during operation of photobioreactors of the present disclosure. Suitable materials can include materials that are not easily degraded by water and microbes such as plastic, rubber, TYVEK, or other slowly degrading materials. Additionally, materials, adhesives, chemicals, or the like can be sprayed onto or otherwise provided on the supporting material 12 to facilitate algal attachment. It will be appreciated that any suitable number of layers of material is contemplated.

It will be appreciated that any suitable algal cells utilized within embodiments of the algal growth system of the present disclosure (including cyanobacteria) as well as fungal strains, such as strains that can be used in aquaculture feed, animal feed, nutraceuticals, or biofuel production can be used. In one or more embodiments, the flexible sheet material is configured to grow algae selected from the group consisting of *Nannochloropsis, Scenedesmus, Haematococcus, Botryococcus, Spirulina, Dunaliella, Arthrospira, Porphyridium, Phaeodactylum, Nitzschia, Crypthecodinium*, and *Schizochytrium. Nannochloropsis* sp., can be used for both biofuel production and aquacultural feed, *Scenedesmus* sp., is a green microalga that can be used in wastewater treatment as well as for fuel production feedstock, *Haematococcus* sp, which can produce a high level of astaxanthin, *Botryococcus* sp. a green microalga with high oil content, *Spirulina* sp. a blue-green alga with high protein content, *Dunaliella* sp. a green microalga containing a large amount of carotenoids, and/or a group of microalgae species producing a high level of long chain polyunsaturated fatty acids can include *Arthrospira, Porphyridium, Phaeodactylum, Nitzschia, Crypthecodinium* and *Schizochytrium*. Any suitable parameter, including gaseous phase $CO_2$ concentration, harvesting frequency, the rotation speed of the RAB reactor, the depth of the biofilm harvested, the ratio of submerged portion to the air-exposure portion of the RAB reactor, or the gap between the different modules of the RAB system can be optimized for any suitable species. It will be appreciated that the listed genus and species are described by way of example and additions and combinations are contemplated.

It will be appreciated that any suitable algal cells utilized within embodiments of the algal growth system of the present disclosure (including cyanobacteria) as well as fungal strains, such as strains that can be used in aquaculture feed, animal feed, nutraceuticals, or biofuel production can be used. Such strains can include *Nannochloropsis* sp., which can be used for both biofuel production and aquacultural feed, *Scenedesmus* sp., a green microalga that can be used in wastewater treatment as well as for fuel production feedstock, *Haematococcus* sp, which can produce a high level of astaxanthin, *Botryococcus* sp. a green microalga with high oil content, *Spirulina* sp. a blue-green alga with high protein content, *Dunaliella* sp. a green microalga containing a large amount of carotenoids, and/or a group of microalgae species producing a high level of long chain polyunsaturated fatty acids can include Arthrospira, Porphyridium, *Phaeodactylum, Nitzschia, Crypthecodinium* and *Schizochytrium*. Any suitable parameter, including gaseous phase $CO_2$ concentration, harvesting frequency, the rotation speed of the RAB reactor, the depth of the biofilm harvested, the ratio of submerged portion to the air-exposure portion of the RAB reactor, or the gap between the different modules of the RAB system can be optimized for any suitable species. It will be appreciated that the listed genus and species are described by way of example and additions and combinations are contemplated.

Figure 6:
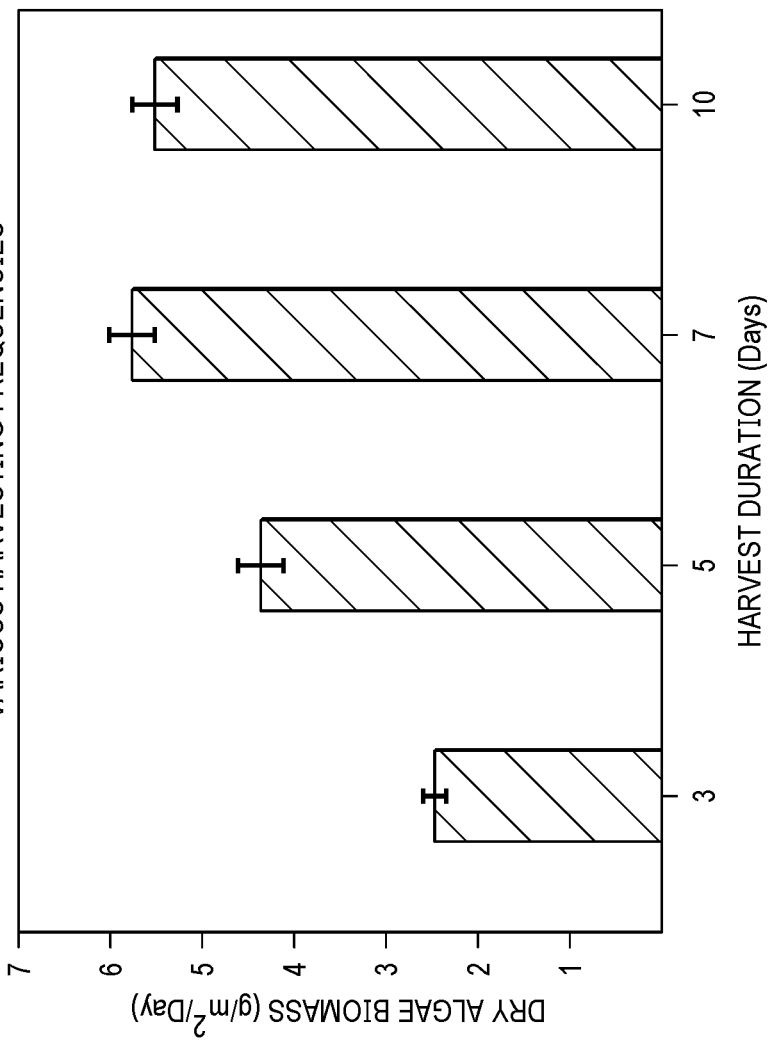
FIG. 6 depicts a bar chart of harvesting frequencies for an algal strain according to one embodiment.

Referring to FIG. 6, any harvesting schedule can be used in accordance with example embodiments described herein. The mechanism of harvesting biomass from the biofilm can be, for example, scraping, high pressure air, vacuum, or combinations thereof. Biomass productivity may vary by species and any suitable harvesting time is contemplated to maximize such productivity. For example, FIG. 6 shows a specific species as a function of harvesting time by growing the algae on a RAB system then harvesting the cells at different durations. As shown in FIG. 6, for *Chlorella*, the optimal harvest frequency may be every 7 days. In example embodiments, managing other parameters such as $CO_2$ concentration and nutrient loading may also impact algal growth performance.

Figure 9:
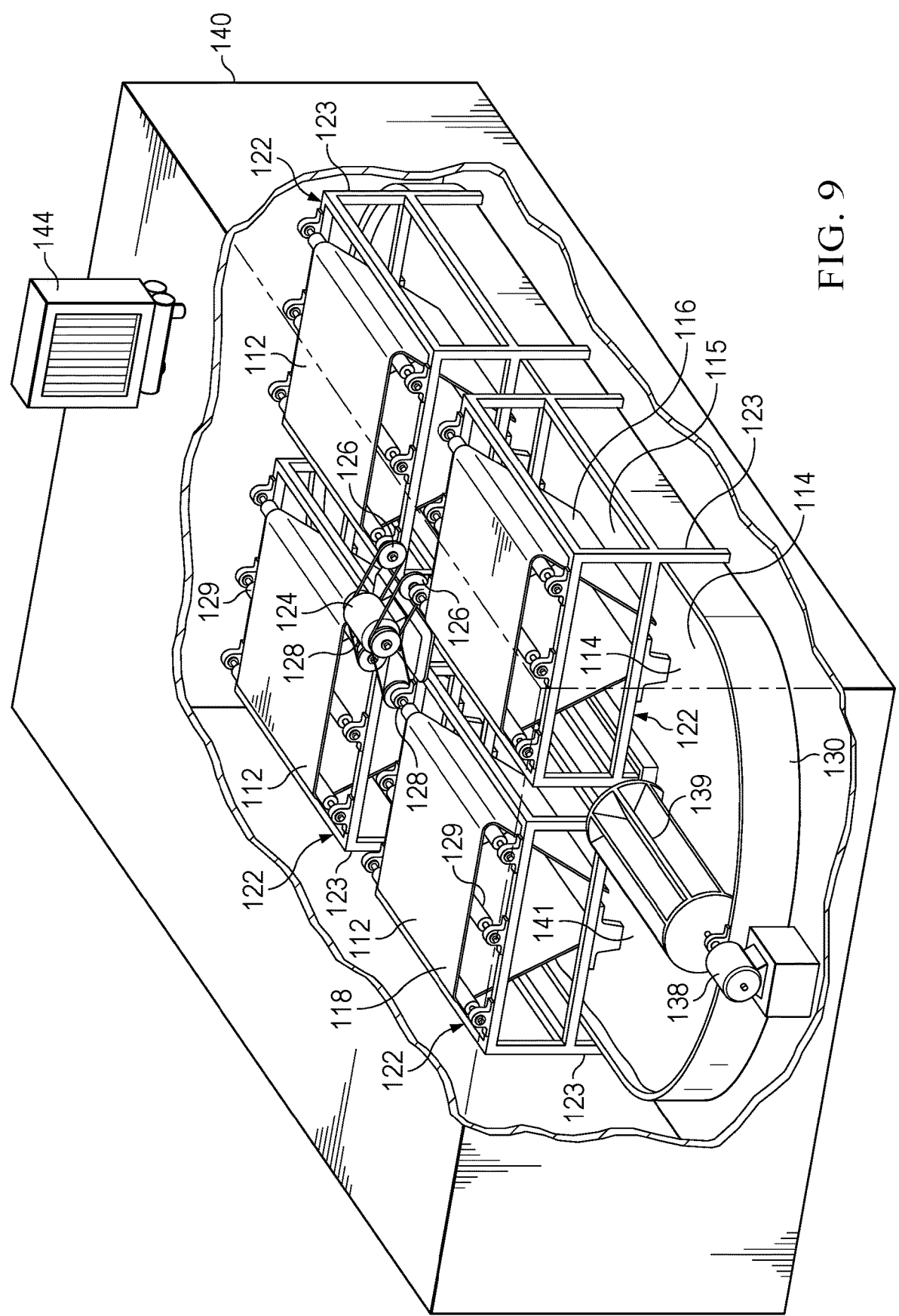
FIG. 9 depicts a partial cutaway perspective view of a revolving algal biofilm bioreactor having a plurality of associated algal growth systems, a raceway, and a resource reclamation device on a top portion thereof according to one embodiment.
Figure 10:
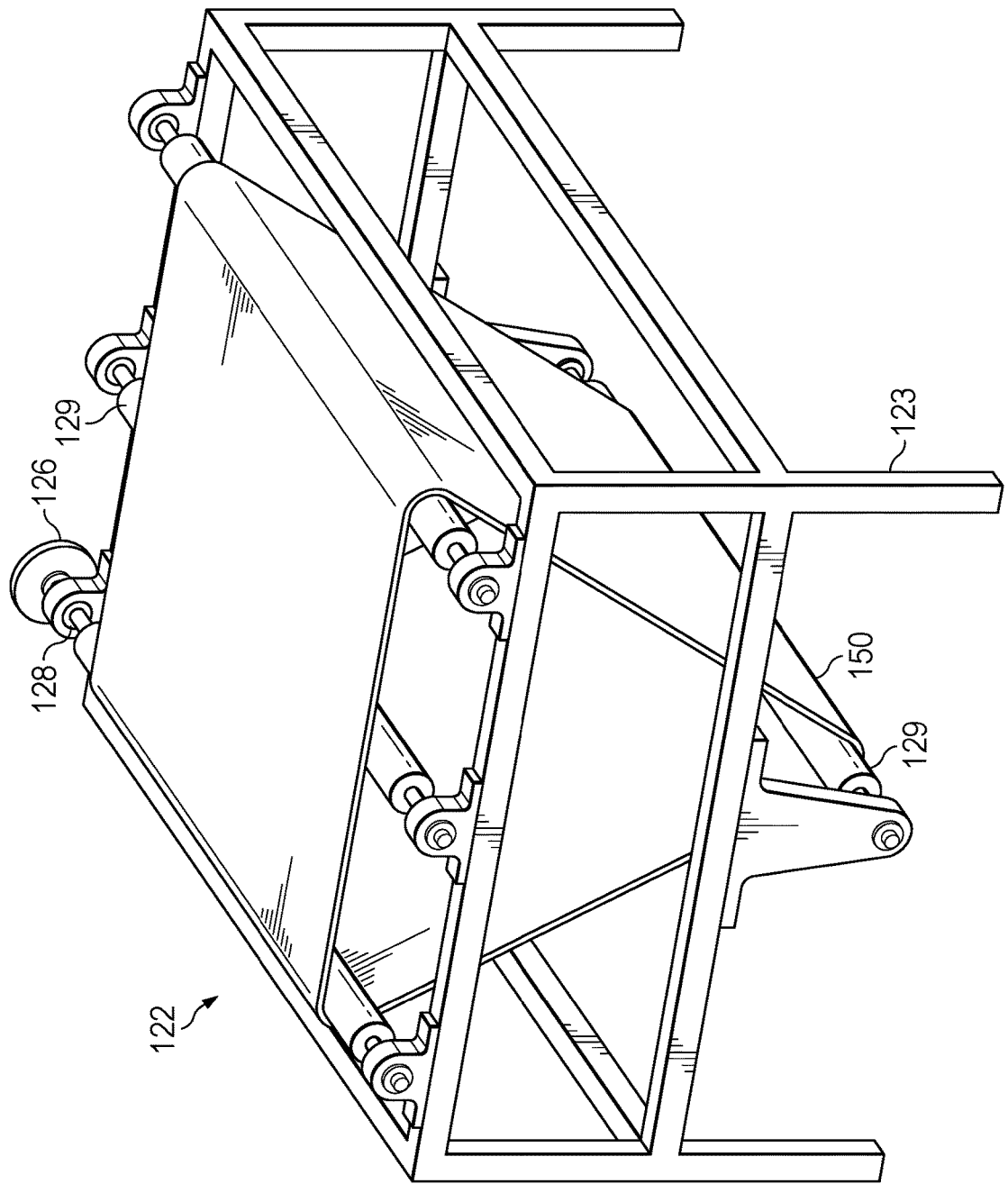
FIG. 10 depicts a perspective view of a single algal growth system of the plurality of associated algal growth systems illustrated in FIG. 9.
Figure 11:
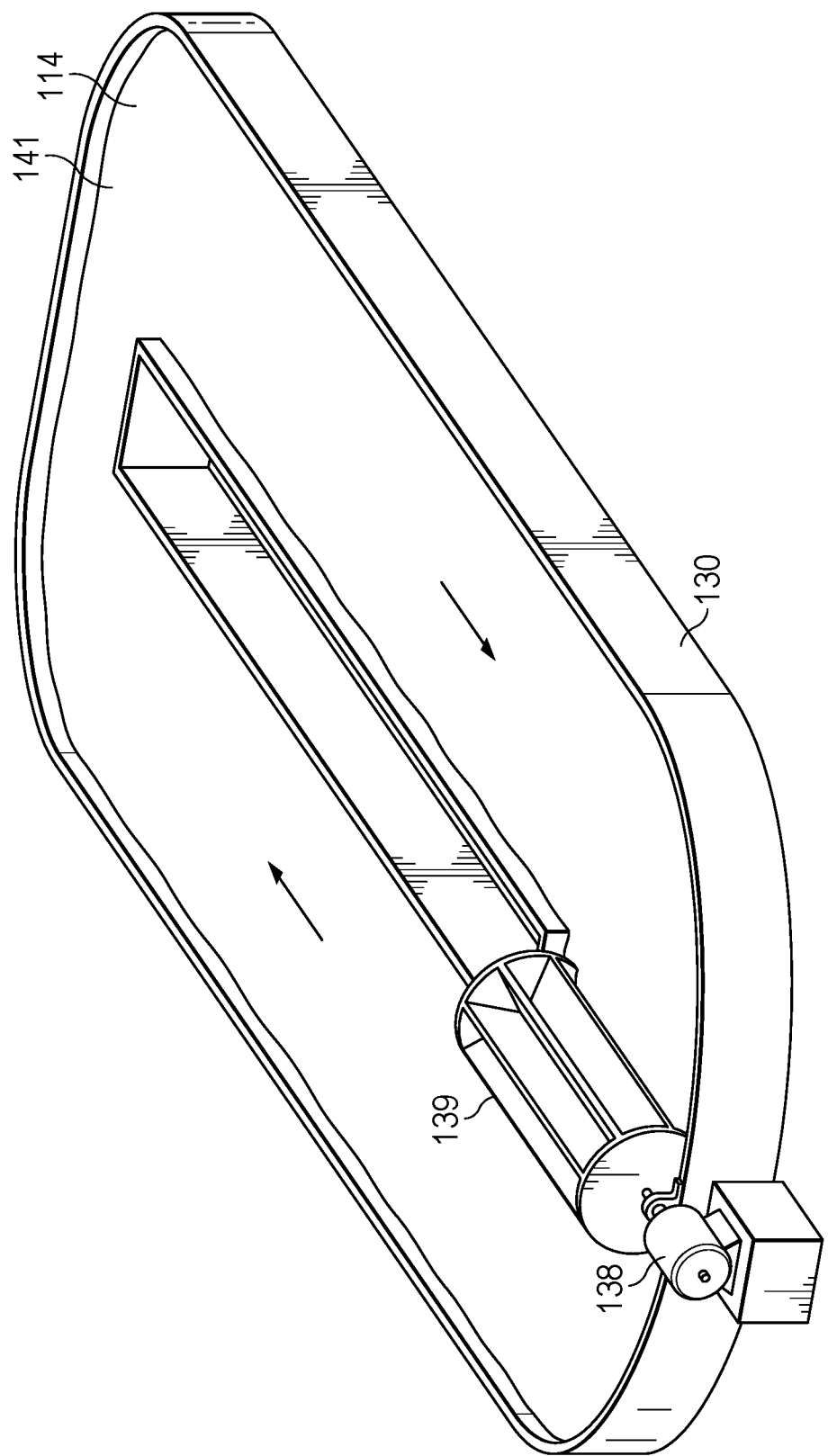
FIG. 11 depicts a perspective view of the raceway illustrated in FIG. 9.

Referring to FIGS. 9-11, shown is an alternate embodiment of a revolving algal biofilm photobioreactor (RABP) 100, in which algal cells 118 can be attached to a solid surface of a supporting material 112 that can be rotated between a nutrient-rich liquid phase 115 and a $CO_2$-rich gaseous phase 116 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 100 may require only a small amount of water for operation, relative to existing methods, where only the bottom 150 (FIG. 10) of an algal growth unit or mechanized harvesting unit 122 may be immersed in a contacting liquid 114. The photobioreactor 100 can include one or a plurality of mechanized harvesting units 122, having frames 123 that can be positioned in a raceway 130 containing contacting fluid 114. Example embodiments can include a large number of mechanized harvesting units such that the photobioreactor can be scaled up to an industrial scale. For example, a single raceway could have 20, 50, 100, or more mechanized harvesting units 122. In an example embodiment, the one or a plurality of mechanized harvesting units 122 can be retrofitted onto existing raceway pond systems.

Example embodiments can be used in fresh water systems and can be also be adapted to saltwater culture systems. In one example, the ocean can naturally supply the algal cells with sufficient sunlight, nutrient, water, and $CO_2$, which in turn may decrease operational costs associated with operation of the photobioreactor 100. Similar to greenhouse 40, the algal growth system 100 will also be contained within greenhouse 140 to act as a natural apparatus to assist in the capture of resources produced by the growing process, which will also decrease operational costs associated with operation of the photobioreactor 100. In one or more embodiments, a resource reclamation device 144, similar to resource reclamation device 44, is located on a top portion of the greenhouse 140 to assist in the recapture of the resources produced during the growing process. Embodiments of the mechanized harvesting units 122 can be placed, for example, in any suitable fluid retaining location or device.

Embodiments of the photobioreactor 100 can include a drive motor 124 and a gear system 126 that can rotate one or a plurality of drive shafts 128, where the one or a plurality of drive shafts 128 can correspondingly rotate the supporting material 112, such as a flexible sheet material for growing algal cells 118. The photobioreactor 100 can include one or a plurality of rollers 129 that can support and guide the supporting material 112. The supporting material 112 can be rotated into contact with the contacting liquid 114, which can allow the algal cells 118 to attach to the supporting material 112. The drive motor 124 can include a gear system 126 or pulley system that can drive the one or a plurality of drive shafts 128, where the one or a plurality of drive shafts 128 can rotate the supporting material 112 into and out of the contacting liquid 114.

Embodiments can also include a raceway 130, mister, water dripper, or any other suitable component or mechanism that can keep algae, which can be attached to the support material 112, moist. Embodiments can include any suitable scraping system, vacuum system or mechanism for harvesting the algal cells 118 from the supporting material 112. It will be appreciated that the drive motor 124 can be associated with a plurality of mechanized harvesting units 122 or, in an alternate embodiment, each mechanized harvesting unit 122 can be associated with an independent motor, gear, and/or drive shaft system. It may be efficient to operate one or more of the mechanized harvesting units 122 on the same schedule, but it may also be advantageous to operate some or all of the mechanized harvesting units 122 on different schedules. For example, in one embodiment, a mechanized harvesting unit 122 exposed to natural light can be associated with a light sensor (not shown) and controller (not shown) such that the rotation speed of the supporting material 112 is optimized relative to the available light coming through greenhouse 140. In such an example, the mechanized harvesting units 122 in the same facility may have different, or slightly different environmental conditions, where operating each mechanized harvesting unit 122 independently may substantially optimize the overall system 100.

The mechanized harvesting unit 122 can have a generally triangle-shaped configuration supported by frame 123. It will be appreciated that the frame 123 can be constructed from any suitable material, such as metal, and can have any suitable configuration. The frame 123 can be substantially level relative to a flat surface, can be stepped, or otherwise shaped to accommodate an incline or an uneven surface. The frame 123 can include telescoping components (not shown), such as telescoping legs, which may allow the frame to be used effectively as a retrofit in existing raceways, for example. The frame 123 can be stackable (not shown) or can be coupled in a side-by-side fashion with other frames in an interlocking manner such that a plurality of mechanized harvesting systems 122 can be connected to form a photobioreactor 100. Such a modular system may allow for a few mechanized harvesting system designs to be used in a wide variety of locations and situations.

One or a plurality of mechanized harvesting units 122 can be associated with the raceway 130 in any suitable manner or configuration. For example, each mechanized harvesting unit 122 can be integral with or permanently affixed to the raceway 130. In an alternate embodiment, each mechanized harvesting unit 122 can be selectively removable or adjustable relative to the raceway 130, where the mechanized harvesting unit 122 can be removed for cleaning, harvesting, replacement, upgrade, or the like.

One or a plurality of mechanized harvesting units 122 can be associated with the raceway 130 in any suitable manner or configuration. For example, each mechanized harvesting unit 122 can be integral with or permanently affixed to the raceway 130. In an alternate embodiment, each mechanized harvesting unit 122 can be selectively removable or adjustable relative to the raceway 130, where the mechanized harvesting unit 122 can be removed for cleaning, harvesting, replacement, upgrade, or the like.

Referring to FIG. 11, the raceway 130 can have any suitable shape or configuration. In one example, the raceway 130 can include a motor 138 that can be configured to drive a paddlewheel 139. The paddlewheel 139 can be configured to create a current or flow within the raceway 130 that may facilitate the growth of algal cells 118. It will be appreciated that the raceway 130, motor 138, and paddlewheel 139 are shown by way of example only, where any suitable mechanism to provide a desirable flow or current in a suitable reservoir is contemplated. The raceway 130 can be open or otherwise exposed to light coming through the greenhouse 140 such that algae cells 118 can easily grow within the raceway 130. The raceway 130 can have a region 141 that can be exposed to light coming through the greenhouse 140 and may not contain a mechanized harvesting unit 122, where the region 141 can be used to cultivate or grow a supply of algal cells 118 within the raceway 130. Providing such a region 141, where the region 141 can have any suitable shape or configuration, may make the system self-sustaining and may reduce the likelihood that the system needs to be seeded or reseeded with algal cells 118.

Figure 12:
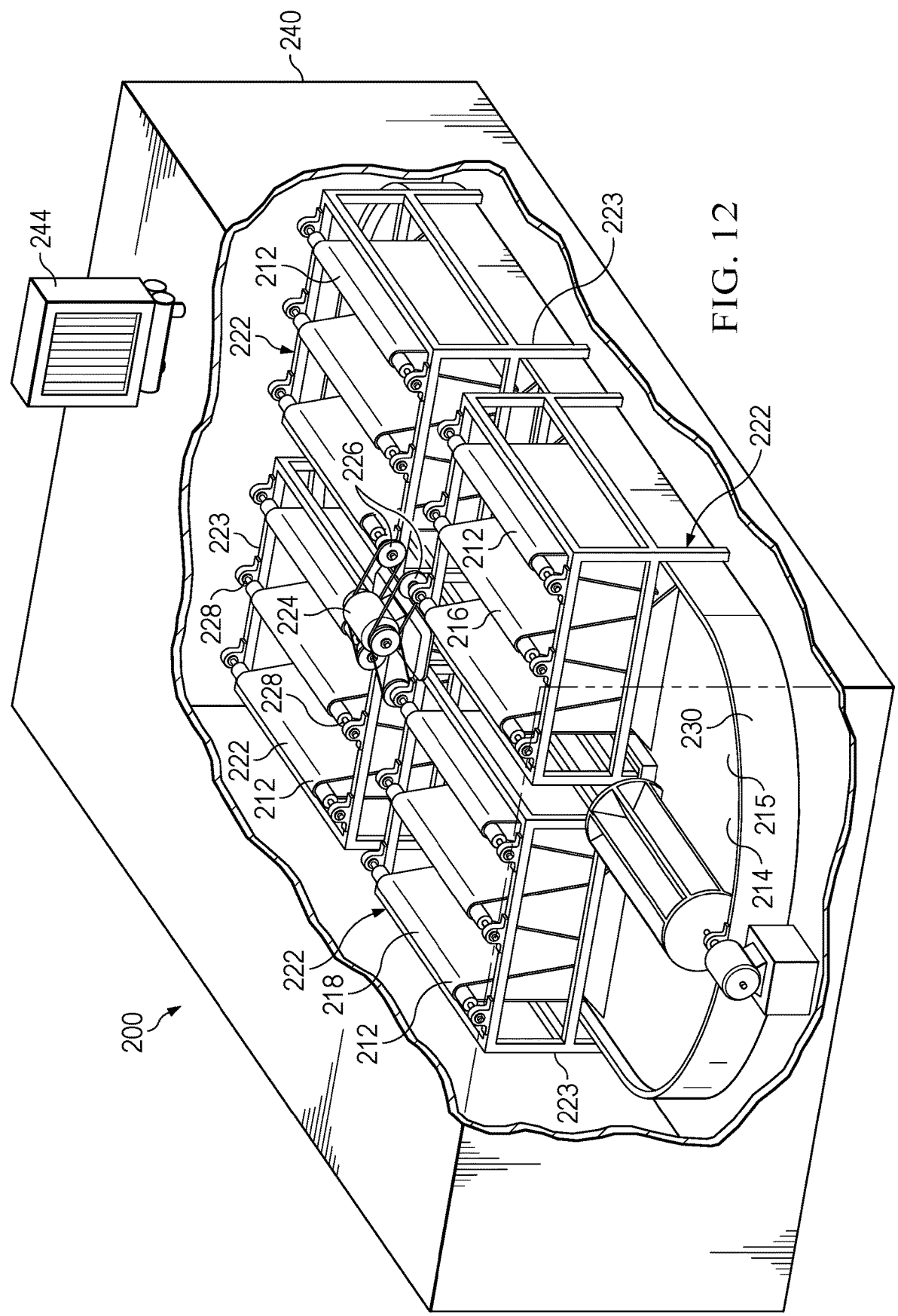
FIG. 12 depicts a partial cutaway perspective view of a revolving algal biofilm bioreactor having a plurality of associated algal growth systems, a raceway, and a resource reclamation device on a top portion thereof according to an alternate embodiment.
Figure 13:
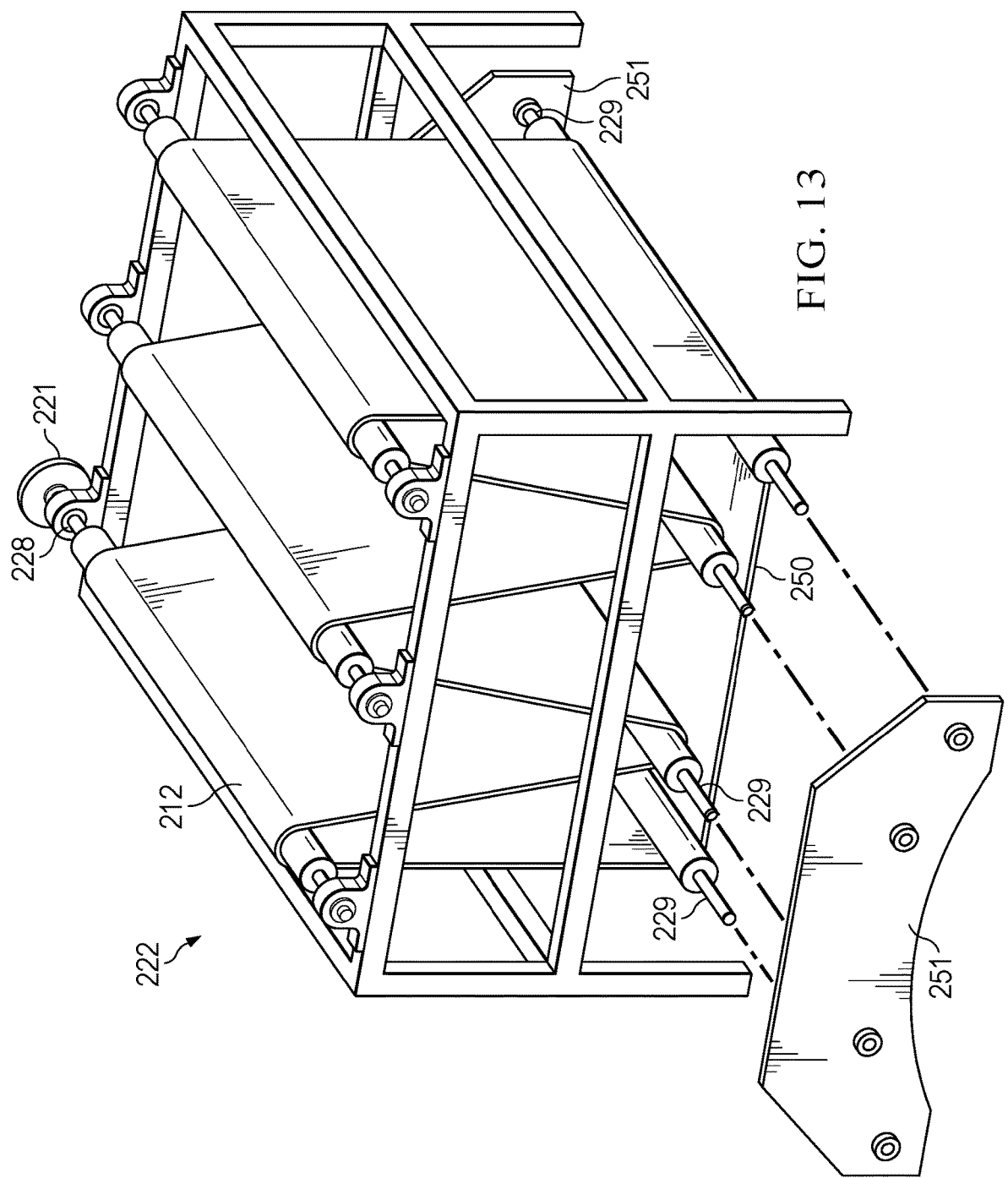
FIG. 13 depicts a perspective view of a single algal growth system of the plurality of associated algal growth systems illustrated in FIG. 12.

Referring to FIGS. 12 and 13, shown is an alternate embodiment of a revolving algal biofilm photobioreactor (RABP) 200, in which algal cells 218 can be attached to a solid surface of a supporting material 212 that can be rotated between a nutrient-rich liquid phase 215 and a $CO_2$-rich gaseous phase 216 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 200 may require only a small amount of water for operation, relative to existing methods, where only the bottom 250 (FIG. 13) of an algal growth unit or mechanized harvesting unit 222 may be immersed in a contacting liquid 214.

The photobioreactor 200 can include one or a plurality of mechanized harvesting units 222, having frames 223, which can be positioned in a raceway 230 containing contacting fluid 214. Example embodiments can include a large number of mechanized harvesting units 222 such that the photobioreactor 200 can be scaled up to an industrial scale. For example, a single raceway could have 20, 50, 100, or more mechanized harvesting units 222. In an example embodiment, the one or a plurality of mechanized harvesting units 222 can be retrofitted onto existing raceway pond systems. Embodiments of the mechanized harvesting units 222 can be placed, for example, in any suitable fluid retaining location or device. Similar to greenhouse 40, the photobioreactor 200 will also be contained within greenhouse 240 to act as a natural apparatus to assist in the capture of resources produced by the growing process, which will also decrease operational costs associated with operation of the photobioreactor 200. In one or more embodiments, a resource reclamation device 244, similar to resource reclamation device 44, is located on a top portion of the greenhouse 240 to assist in the recapture of the resources produced during the growing process.

Embodiments of the photobioreactor 200 can include a drive motor 224 and a gear system 226 that can rotate one or a plurality of drive shafts 228, where the one or a plurality of drive shafts 228 can correspondingly rotate the supporting material 212, such as a flexible sheet material for growing algal cells 218. The photobioreactor 200 can include one or a plurality of rollers 229 that can support and guide the supporting material 212. The supporting material 212 can be rotated into contact with the contacting liquid 214, which can allow the algal cells 218 to attach to the supporting material 212. The drive motor 224 can include a gear system 226 or pulley system that can drive the one or a plurality of drive shafts 228, where the one or a plurality of drive shafts 228 can rotate the supporting material 212 into and out of the contacting liquid 214. Embodiments can also include a raceway 230, mister, water dripper, or any other suitable component or mechanism that can keep algae, which can be attached to the support material 212, moist.

Embodiments can include any suitable scraping system, vacuum system or mechanism (not shown) for harvesting the algal cells 218 from the supporting material 212. It will be appreciated that the drive motor 224 can be associated with a plurality of mechanized harvesting units 222 or, in an alternate embodiment, each mechanized harvesting unit 222 can be associated with an independent motor, gear, and/or drive shaft system. It may be efficient to operate one or more of the mechanized harvesting units 222 on the same schedule, but it may also be advantageous to operate some or all of the mechanized harvesting units 222 on different schedules. For example, in one embodiment, a mechanized harvesting unit 222 exposed to natural light coming through greenhouse 240 can be associated with a light sensor (not shown) and controller (not shown) such that the rotation speed of the supporting material 212 is optimized relative to the available light. In such an example, mechanized harvesting units 222 in the same facility may have different, or slightly different environmental conditions, where operating each mechanized harvesting unit 222 independently may substantially optimize the overall system.

The mechanized harvesting unit(s) 222 can have a generally wave-shaped configuration supported by the frame 223. It will be appreciated that the frame 223 can be constructed from any suitable material, such as metal, and can have any suitable configuration in accordance with embodiments described herein. The supporting material 212 of the mechanized harvesting unit 222 can have a substantially wave-shaped configuration as best illustrated in FIG. 13. The supporting material 212 can be a contiguous band of material and can be wound about the one or a plurality of drive shafts 228 or rollers 229 such that any suitable configuration is created. It is contemplated that the supporting material 212 can be a long, contiguous band of material having multiple peaks and valley, as illustrated in FIG. 12. As illustrated, a portion of the supporting material 212 can also pass along the bottom 250 of the mechanized harvesting unit 222. It will be appreciated that a single long band and a plurality of bands having any suitable relationship or configuration are contemplated as making the supporting material 212.

In an example embodiment, the one or a plurality of drive shafts 228 or rollers 229 can be adjusted such that different configuration can be created using the same frame 223. Such an interchangeable system may be beneficial in that certain configurations may be beneficial to particular species of algal cells. An interchangeable system may also allow for different environmental conditions, uses, or use on a wide range of scales. Any other suitable component, such as a plate 251 can be provided to secure components, such as the rollers 229, in a desired configuration.

Figure 14:
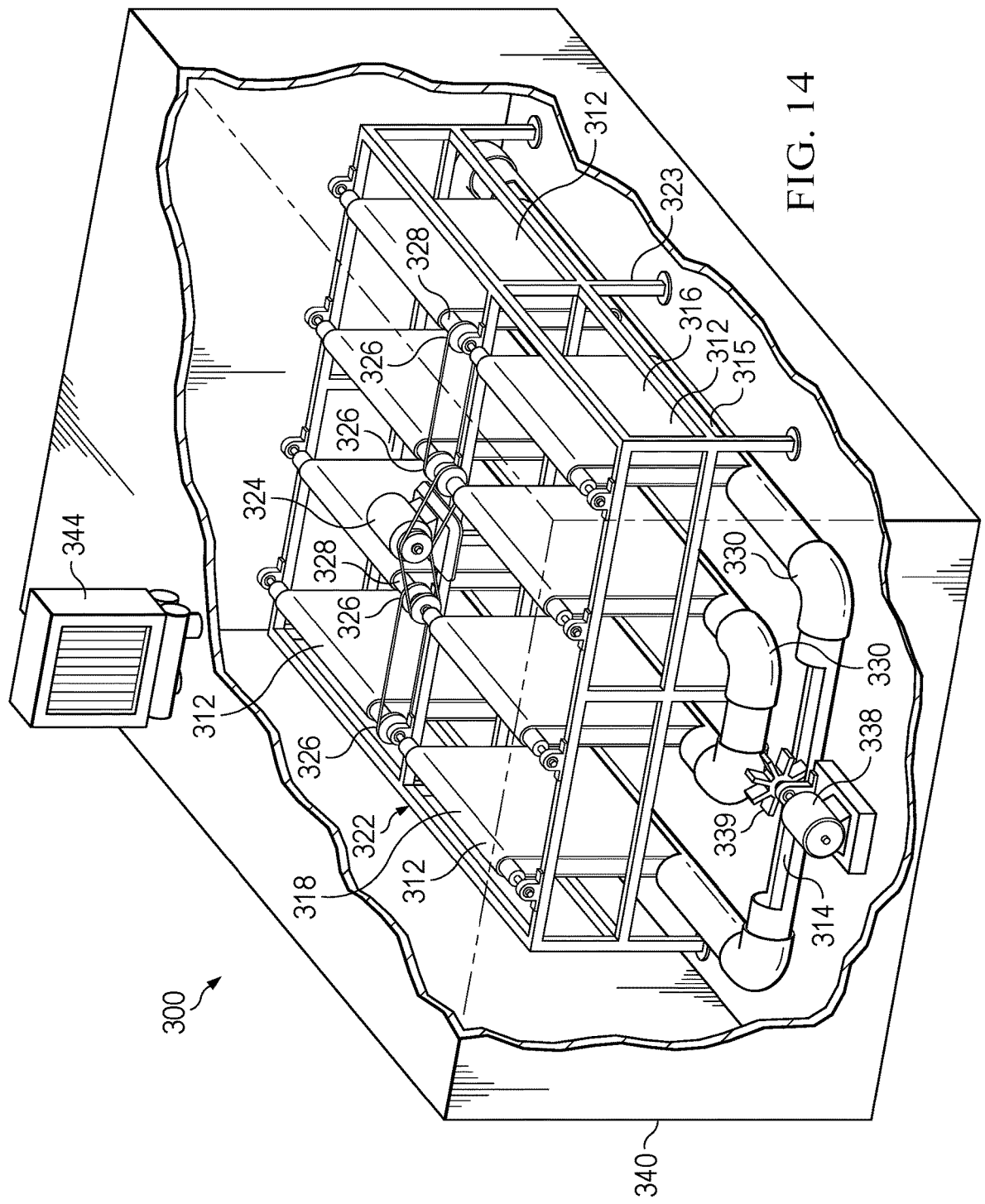
FIG. 14 depicts a partial cutaway perspective view of a revolving algal biofilm bioreactor having an associated algal growth system, a trough system, and a resource reclamation device on a top portion thereof according to one embodiment.
Figure 15:
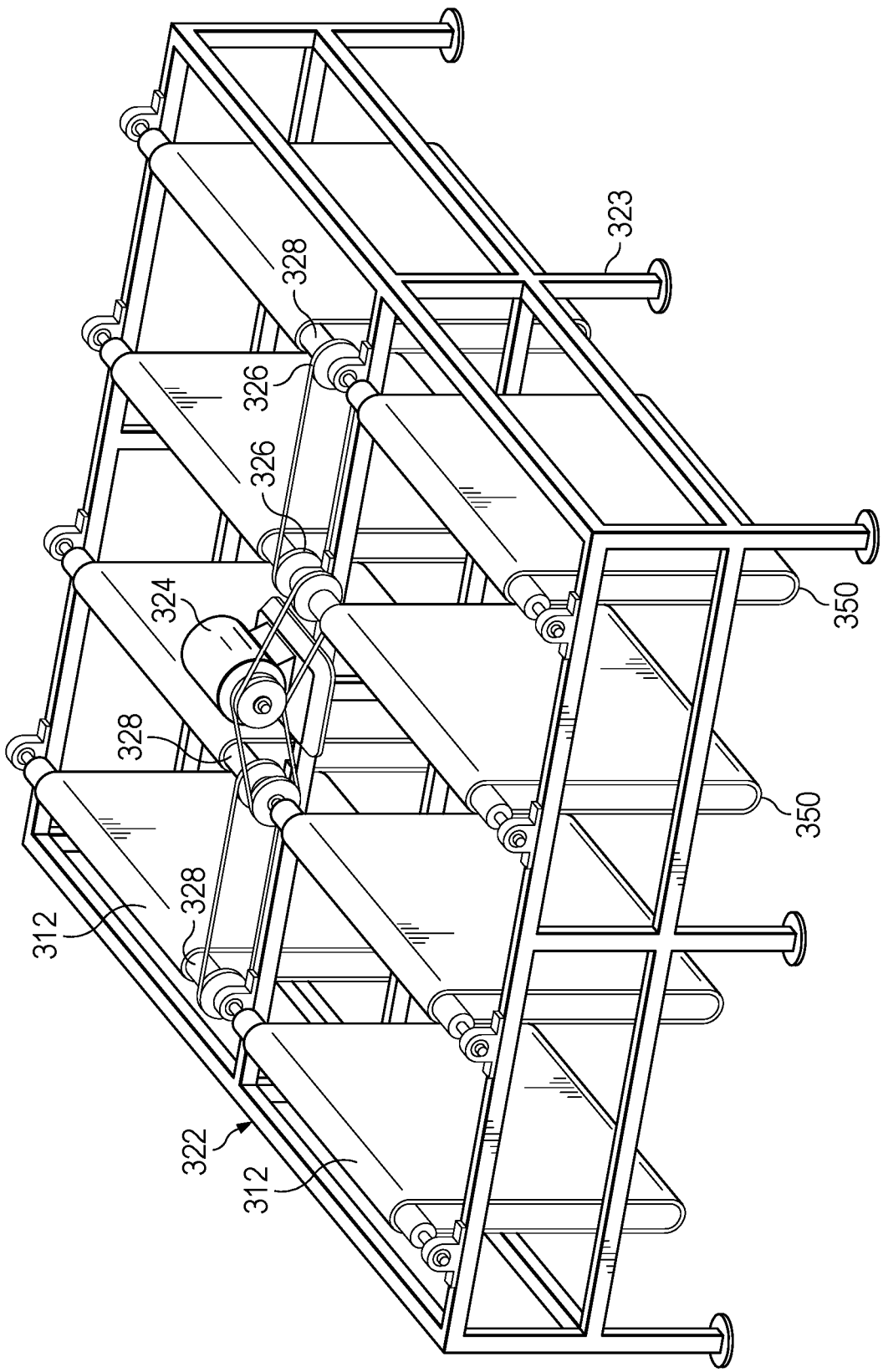
FIG. 15 depicts a perspective view of the algal growth system illustrated in FIG. 14.
Figure 16:
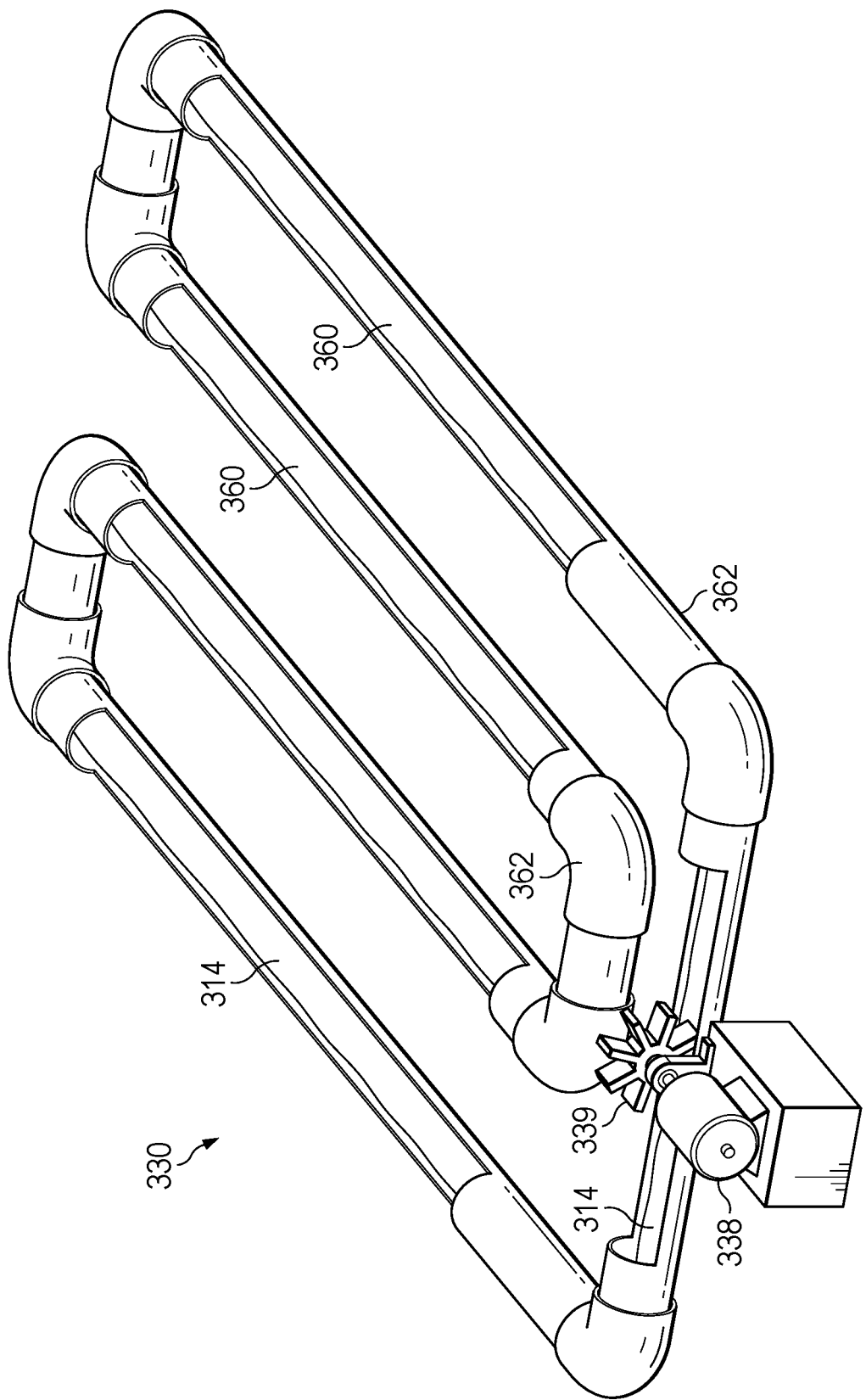
FIG. 16 depicts a perspective view of the trough system illustrated in FIG. 14.

Referring to FIGS. 14-16, shown is an alternate embodiment of a revolving algal biofilm photobioreactor (RABP) 300, in which algal cells 318 can be attached to a solid surface of one or a plurality of supporting materials 312 that can be rotated between a nutrient-rich liquid phase 315 and a $CO_2$-rich gaseous phase 316 for alternative absorption of nutrients and carbon dioxide. The algal biomass can be harvested by scrapping the biomass from the attached surface with a harvesting mechanism (not shown) such as a squeegee, vacuum, reaper, or the like. The photobioreactor 300 may require only a small amount of water for operation, relative to existing methods, where only the bottom 350 (FIG. 15) of an algal growth unit or mechanized harvesting unit 322 may be immersed in a contacting liquid 314. The photobioreactor 300 can include a frame 323, which can be positioned in a trough system 330 containing contacting fluid 314. Example embodiments can include a large number of mechanized harvesting units 322 such that the photobioreactor 300 can be scaled up to an industrial scale.

For example, a single trough system could have 20, 50, 100, or more mechanized harvesting units 322. In an example embodiment, the one or a plurality of mechanized harvesting units 322 can be retrofit onto existing raceway pond systems. Embodiments of the mechanized harvesting units 322 can be placed, for example, in any suitable fluid retaining location or device. Similar to greenhouse 40, the photobioreactor 300 will also be contained within greenhouse 340 to act as a natural apparatus to assist in the capture of resources produced by the growing process, which will also decrease operational costs associated with operation of the photobioreactor 300. In one or more embodiments, a resource reclamation device 344, similar to resource reclamation device 44, is located on a top portion of the greenhouse 340 to assist in the recapture of the resources produced during the growing process.

It will be appreciated that the trough system 330 is shown by way of example only, where any suitable tubing, configuration, or construction is contemplated. The trough system 330 can have a serpentine configuration such that the trough system 330 forms a substantially closed circuit for fluid flow. The trough system 330 can have any suitable shape, where the trough system 330 can have interchangeable parts such that different configurations can be created. The trough system 330 can include any suitable number of apertures 360 and closed sections 362, where apertures 360 can be configured to accept each of the one or a plurality of supporting materials 312. In one embodiment, the apertures 360 can be associated with a closure unit when not in use. Alternatively, apertures 360 can be used in sunlight or well lighted areas to help facilitate algal growth in the contacting liquid 314. The trough system 330 can be associated with a motor 338 and paddlewheel 339 that can be configured to create a fluid dynamic or current flow in the trough system 330. In one embodiment, one or a plurality of paddlewheels 339, or other actuators, can be positioned in the apertures 360.

Embodiments of the photobioreactor 300 can include a drive motor 324 and a gear system 326 that can rotate one or a plurality of drive shafts 328, where the one or a plurality of drive shafts 328 can correspondingly rotate the one or a plurality of supporting materials 312, such as a flexible sheet material for growing algal cells 318. The photobioreactor 300 can include one or a plurality of rollers that can support and guide the one or a plurality of supporting materials 312 or, as illustrated in FIG. 15. The bottom of each of the one or a plurality of supporting materials 312 can hang freely in a substantially vertical configuration. The one or a plurality of supporting materials 312 can be rotated into contact with the contacting liquid 314, which can allow the algal cells 318 to attach to the one or a plurality of supporting materials 312. The drive motor 324 can include a gear system 326 or pulley system that can drive the one or a plurality of drive shafts 328, where the one or a plurality of drive shafts 328 can rotate the one or a plurality of supporting materials 312 into and out of the contacting liquid 314.

Embodiments can also include a trough system 330, mister, water dripper, or any other suitable component or mechanism that can keep algae, which can be attached to the one or a plurality of supporting materials 312, moist. Embodiments can include any suitable scraping system, vacuum system or mechanism for harvesting the algal cells 318 from the one or a plurality of supporting materials 312. It will be appreciated that the drive motor 324 can be associated with a plurality of mechanized harvesting units 322 or one or a plurality of supporting materials 312. In an alternate embodiment, each of the one or a plurality of supporting materials 312 can be associated with an independent motor, gear, and/or drive shaft system (not shown). It may be efficient to operate one or more of the one or a plurality of supporting materials 312 on the same schedule, but it may also be advantageous to operate some or all of the one or a plurality of supporting materials 312 on different schedules. For example, in one embodiment, a supporting material 312 exposed to natural light coming through the greenhouse 340 can be associated with a light sensor (not shown) and controller (not shown) such that the rotation speed of the supporting material 312 is optimized relative to the available light. In such an example, one or a plurality of supporting materials 312 in the same facility may have different, or slightly different environmental conditions, where operating each one or a plurality of supporting materials 312 independently may substantially optimize the overall system.

Figure 17:
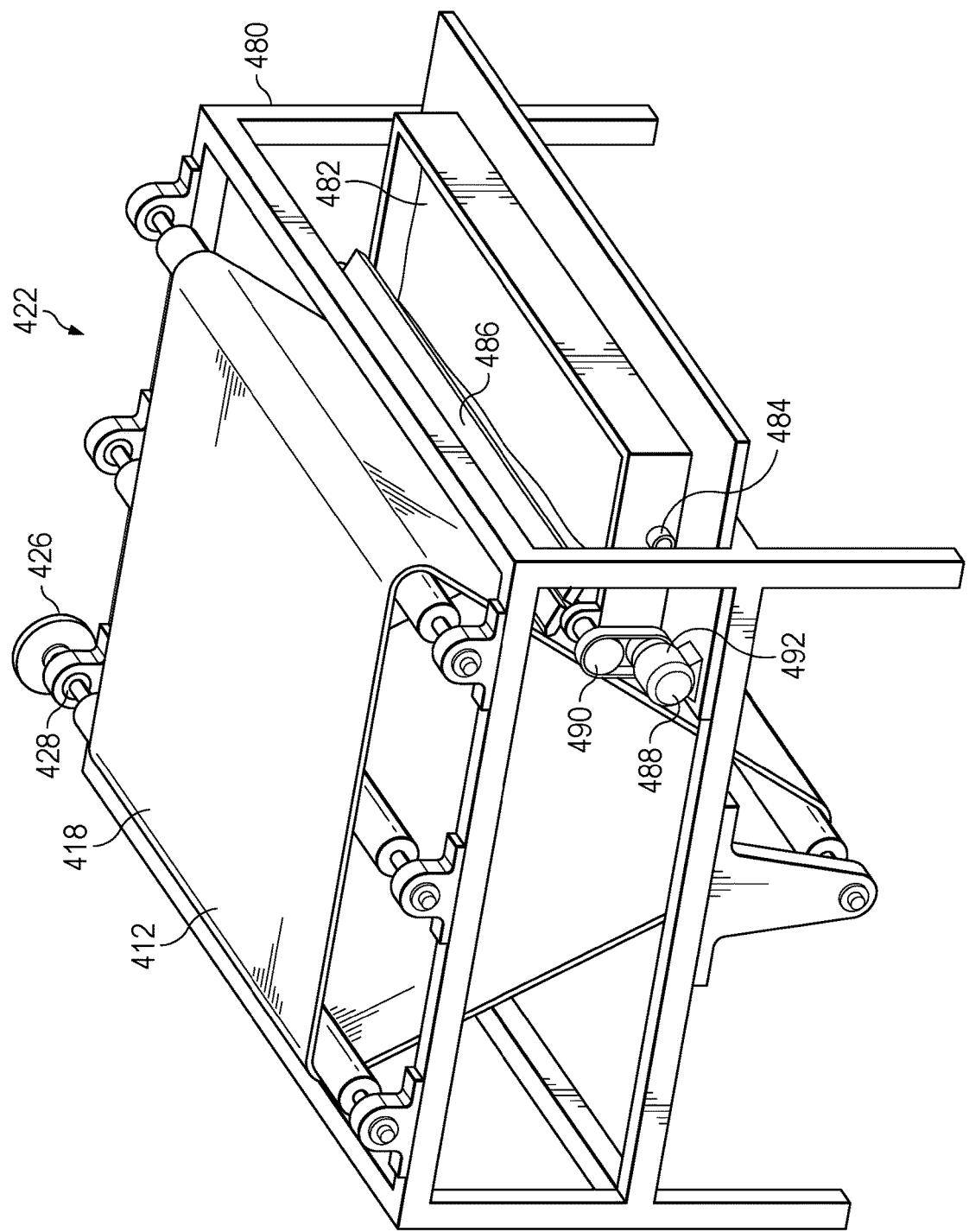
FIG. 17 depicts a perspective view of an algal growth system shown with a harvesting system according to one embodiment.

Referring to FIG. 17, an example embodiment of an algal growth system or mechanized harvesting unit 422 is shown, in which algal cells 418 can be attached to a solid surface of a supporting material 412. Embodiments of the mechanized harvesting unit 422 can include a drive motor (not shown), and a gear system 426 that can rotate one or a plurality of drive shafts 428, where the one or a plurality of drive shafts 428 can correspondingly rotate the supporting material 412, such as a flexible sheet material. Embodiments of the mechanized harvesting unit 422 can include a harvesting system 480 that can include any suitable manual or automatic harvesting mechanism and/or a harvesting reservoir 482.

The harvesting system 480 can include a vacuum system 484 and a scraper 486 for harvesting the algal cells 418 from the supporting material 412. The scraper 486 can be coupled with a motor 488 and a pulley system or actuator 490 such that the scraper 486 can be selectively engaged with the supporting material 412. The motor 488 can be associated with a controller 492 such that the harvesting system 480 can be programmed to scape, harvest, or perform any other suitable function automatically or on a predetermined schedule. Similar to greenhouse 40, the algal growth system 422 will also be contained within greenhouse (not shown) to act as a natural apparatus to assist in the capture of resources produced by the growing process, which will also decrease operational costs associated with operation. In one or more embodiments, a resource reclamation device (not shown), similar to resource reclamation device 44, will be located on a top portion of the greenhouse to assist in the recapture of the resources produced during the growing process.

Figure 20:
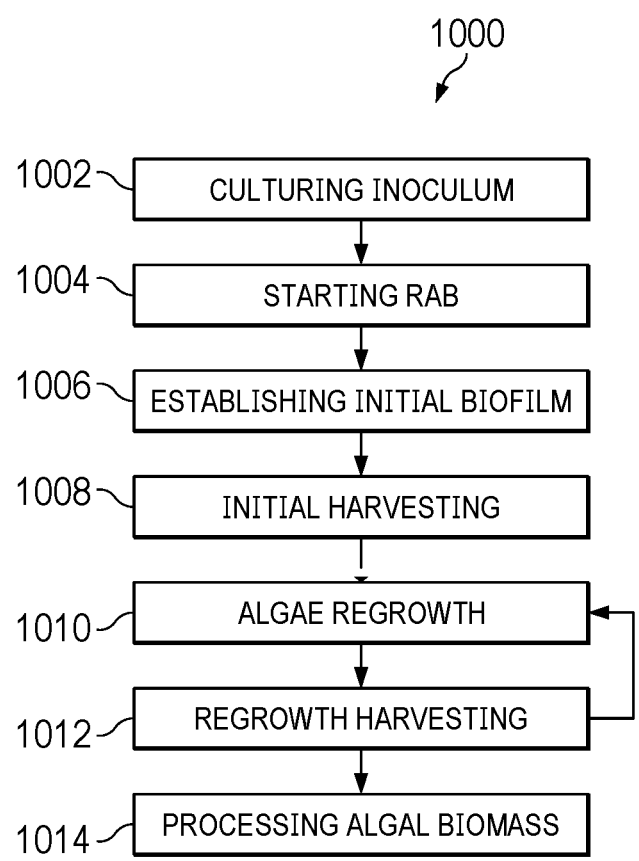
FIG. 20 depicts a flow chart showing a method for growing and harvesting algae using a raceway according to one embodiment.

FIG. 20 depicts a flow chart illustrating one example of a method 1000 that can be used for growing and/or harvesting algal cells using a raceway, such as the raceway 130 shown in FIGS. 9 and 11. The method 1000 can include Culturing Algal Inoculum 1002, which can include culturing suspended algae in an open pond, raceway, or the like, until the algal cell density is between from about 0.05 g/L to about 1.0 g/L. It will be appreciated that any suitable density of any suitable algal cells is contemplated. The method 1000 can include Starting the RAB 1004, which can include rotating or actuating the supporting material of the RAB, algal growth system, mechanized harvesting unit, or the like, in accordance with versions described herein. The RAB or other suitable system can be rotated, for example, at a speed ranging from about ¼ cm/sec to about 10 cm/sec. The RAB can be rotated at from about 2 cm/sec to about 6 cm/sec. In one embodiment, the RAB can be rotated at about 4 cm/sec.

The RAB can be rotated or otherwise actuated at different speeds, which can be selectable, preprogrammed, or based on environmental conditions. Starting the RAB 1004 can include rotating the RAB system for any duration of time such as from about 5 days to about 20 days, where duration of operation can depend on the speed of the algal cells attachment on the surface of the RAB materials.

The method 1000 can include Establishing the Initial Biofilm 1006, which can include the growth of algal cells on the supporting material of the RAB or photobioreactor. The initial biofilm can be deemed to be established when, for example, a threshold density of algal cells is determined. Such a threshold can be any suitable density and the density can be determined using any suitable system or method. The method 1000 can include Initial Harvesting 1008, which can include harvesting the algal biomass from the supporting material of the RAB or photobioreactor. Initial Harvesting 1008 can be accomplished by scraping the algal biofilm, vacuuming, pressurized air, or by any other suitable method.

The method 1000 can include Algae Regrowth 1010, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1010 can include operating, actuating, or rotating the algal biofilm, RAB, or photobioreactor for any suitable time period such as from about 3 days to about 8 days. The time for operating the RAB can depend, for example, on the algal species, culture conditions, rotating speed of the RAB system, the liquid fluid rate reservoir, or any other suitable factor. Method 1000 can include Regrowth Harvesting 1012, which can include harvesting the algal biofilm that has accumulated on the supporting material. The method 1000 can include repeating Algae Regrowth 1010 and Regrowth Harvesting 1012 for as many times as appropriate. The system can operate substantially indefinitely, or can be periodically interrupted for cleaning or for other reasons. The method 1000 can include Processing Algal Biomass 1014, which can include processing the harvested algae by, for example, drying and extracting oil from the harvested algal cells. It will be appreciated that any suitable processing is contemplated. Although not shown as a specific step, it is also contemplated that throughout the method 1000 of FIG. 20, resources produced by the growing process can be collected through a resource reclamation device located on a greenhouse that the method 1000 takes place in.

Figure 19:
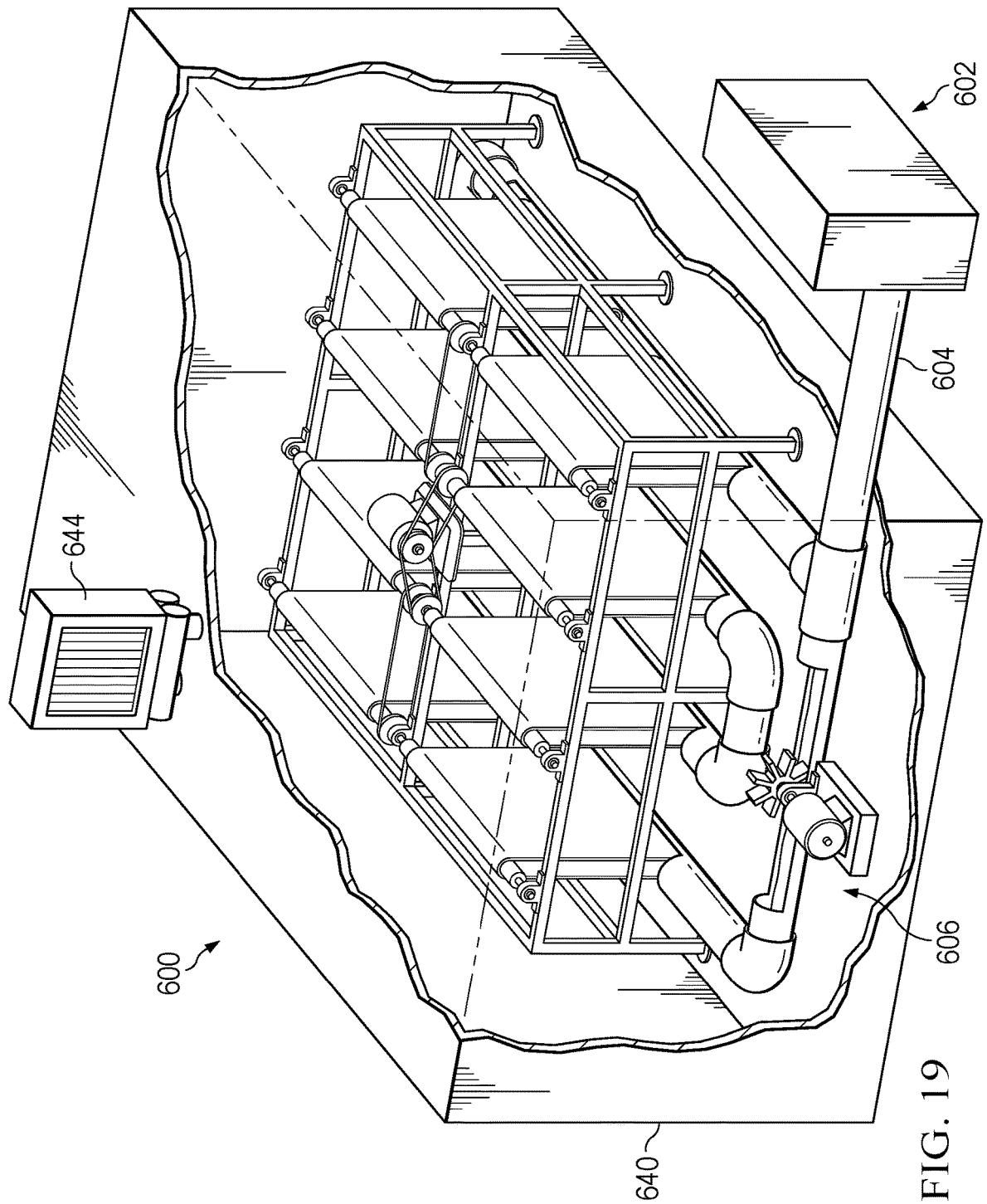
FIG. 19 depicts a partial cutaway perspective view of a photobioreactor with a resource reclamation device on a top portion thereof according to one embodiment.
Figure 21:
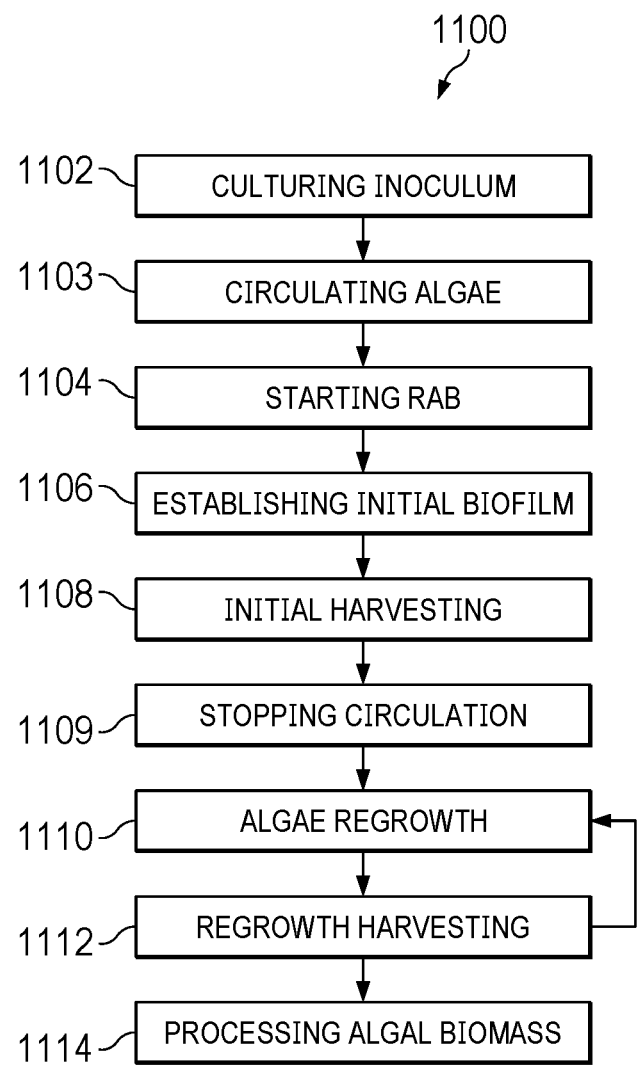
FIG. 21 depicts a flow chart showing a method for growing and harvesting algae using a trough according to one embodiment.

FIG. 21 depicts a flow chart illustrating one example of a method 1100 that can be used for growing and/or harvesting algal cells, such as with a photobioreactor 600 shown in FIG. 19, a trough, a partially enclosed fluid reservoir, or other suitable bioreactor. In such a system, it may be beneficial to seed or otherwise provide algal cells grown at a first location 602 (FIG. 19) and transport the algal cells via a channel 604 (FIG. 19), or other suitable connection, to a second location 606 (FIG. 19), such as to a photobioreactor provided in accordance with versions described herein. The first location can be fluidly coupled to the second location or, in an alternate embodiment, the first location can be a portable bioreactor that can be selectively connected to the second location as needed. Similar to greenhouse 40, the photobioreactor 600 will also be contained within a greenhouse 640 to act as a natural apparatus to assist in the capture of resources produced by the growing process, which will also decrease operational costs associated with operation of the photobioreactor 600. In one or more embodiments, a resource reclamation device 644, similar to resource reclamation device 44, is located on a top portion of the greenhouse 640 to assist in the recapture of the resources produced during the growing process.

The method 1100 can include Culturing Algal Inoculum 1102, which can include culturing suspended algae in an open pond, portable photobioreactor, or the like, at the first location until the algal cell density is between, for example, from about 0.05 g/L to about 3.0 g/L. It will be appreciated that any suitable density of any suitable algal cells is contemplated, although in one embodiment the cell density can be higher than in an open raceway system, where the reduction of light in a trough system may benefit from a higher initial cell density. The method 1100 can include Circulating Algae 1103, which can include providing or otherwise delivering the algal cells from the first location to the trough or partially enclosed system, which can include generating a fluid dynamic or flow such that algal cells from the first growth region are transitioned to the trough in the second region. The method 1100 can include Starting the RAB 1104, which can include rotating or actuating the supporting material of a photobioreactor, algal growth system, mechanized harvesting unit, or the like, in accordance with versions described herein. The RAB or other suitable system can be rotated, for example, at a speed ranging from about ¼ cm/sec to about 10 cm/sec. The RAB can be rotated at from about 2 cm/sec to about 6 cm/sec. The RAB can be rotated at about 4 cm/sec. The RAB can be rotated or otherwise actuated at different speeds, which can be selectable, preprogrammed, or based on environmental conditions. Starting the RAB 1104 can include rotating the RAB system for any duration of time such as from about 5 days to about 20 days, where duration of operation can depend on the speed of the algal cells attachment on the surface of the RAB materials.

The method 1100 can include Establishing the Initial Biofilm 1106, which can include the growth of algal cells on the supporting material of an RAB or photobioreactor. The initial biofilm can be deemed to be established when, for example, a threshold density of algal cells is determined. Such a threshold can be any suitable density and the density can be determined using any suitable system or method. The method 1100 can include Initial Harvesting 1108, which can include harvesting the algal biomass from the supporting material of the RAB or photobioreactor. Initial Harvesting 1108 can be accomplished by scraping the algal biofilm, vacuuming, pressurized air, or by any other suitable method.

The method 1100 can include Stopping Circulation 1109, which can include stopping delivery of algal cells from the first growth location to the second trough location, for example. In one embodiment, once the RAB is seeded with algal cells, the RAB may no longer need to be seeded or otherwise infused with additional algal cells for subsequent regrowth and harvesting steps. It will be appreciated that a feeder or seeding system for algal cells can be reattached or can be maintained throughout if desirable. The method 1100 can include Algae Regrowth 1110, where after harvesting, residual algal cells can remain on the supporting material surface and can automatically serve as inoculum for a next cycle of growth or regrowth. Harvesting can be performed such that a sufficient density of algal cells can be left on the supporting material to facilitate regrowth. Algae Regrowth 1110 can include operating, actuating, or rotating the algal biofilm, RAB, or photobioreactor for any suitable time period such as from about 3 days to about 8 days.

The time for operating the RAB can depend, for example, on the algal species, culture conditions, rotating speed of the RAB system, the liquid fluid rate of the reservoir, the type of reservoir, or any other suitable factor. Method 1100 can include Regrowth Harvesting 1112, which can include harvesting the algal biofilm that has accumulated on the supporting material. The method 1100 can include repeating Algae Regrowth 1110 and Regrowth Harvesting 1112 for as many times as appropriate. The system can operate substantially indefinitely, or can be periodically interrupted for cleaning or for other reasons. The method 1100 can include Processing Algal Biomass 1114, which can include processing the harvested algae by, for example, drying and extracting oil from the harvested algal cells. It will be appreciated that any suitable processing is contemplated. Although not shown as a specific step, it is also contemplated that throughout the method 1100 of FIG. 21, resources produced by the growing process can be collected through the resource reclamation device 644 located on greenhouse 640 that the method 1100 takes place in.

Figure 25:
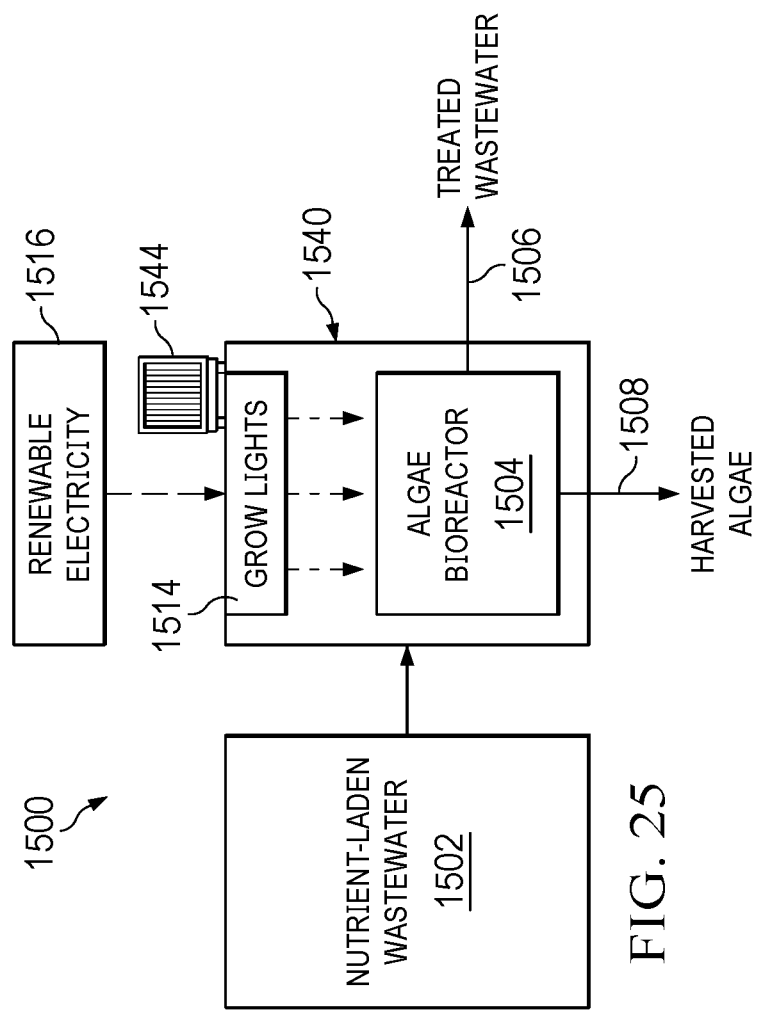
FIG. 25 depicts a plan view of a photobioreactor with a resource reclamation device on a top portion thereof and grow lights within according to one embodiment.

Referring to FIG. 25, an example embodiment of an algal growth system 1500 is shown. System 1500 can be utilized to treat municipal, industrial, and agricultural wastewater 1502. System 1500 utilizes a RAB system 1504 that is modeled after any of the RAB systems disclosed above. Similar to greenhouse 40, algal growth system 1500 will also be contained within a greenhouse 1540 to act as a natural apparatus to assist in the capture of resources produced by the growing process, which will also decrease operational costs associated with operation of system 1500. In one or more embodiments, a resource reclamation device 1544, similar to resource reclamation device 44, is located on a top portion of the greenhouse 1540 to assist in the recapture of the resources produced during the growing process. In one embodiment, the resources collected within system 1500 can be recycled back into the greenhouse 1540 to enrich the growing environment for the algae being produced within the system 1500. Once cycled through the system 1500, the wastewater 1502 will come out as treated wastewater 1506 that can be reused. The RAB system 1504 will also produce algae as in any of the embodiments discussed above, that produced algae can be harvested. The harvested algae 1508 is an additional resource of system 1500.

It is also contemplated that the greenhouse 1540 can contain grow lights 1514 that can help the system 1500 run when sunlight is not available. In one or more embodiments, the grow lights 1514 can be powered by renewable energy 1516 in order to reduce the carbon footprint of the system 1500. Renewable energy 1516 can be from wind, solar, or hydro sources of electricity. In other embodiments, the renewable energy 1516 could come from a renewable fuel generated electricity that is produced through system 1500 or additional upstream processes. In one embodiment, onsite generated renewable energy 1516 can come from solar panels mounted on greenhouse 1540.

Figure 26:
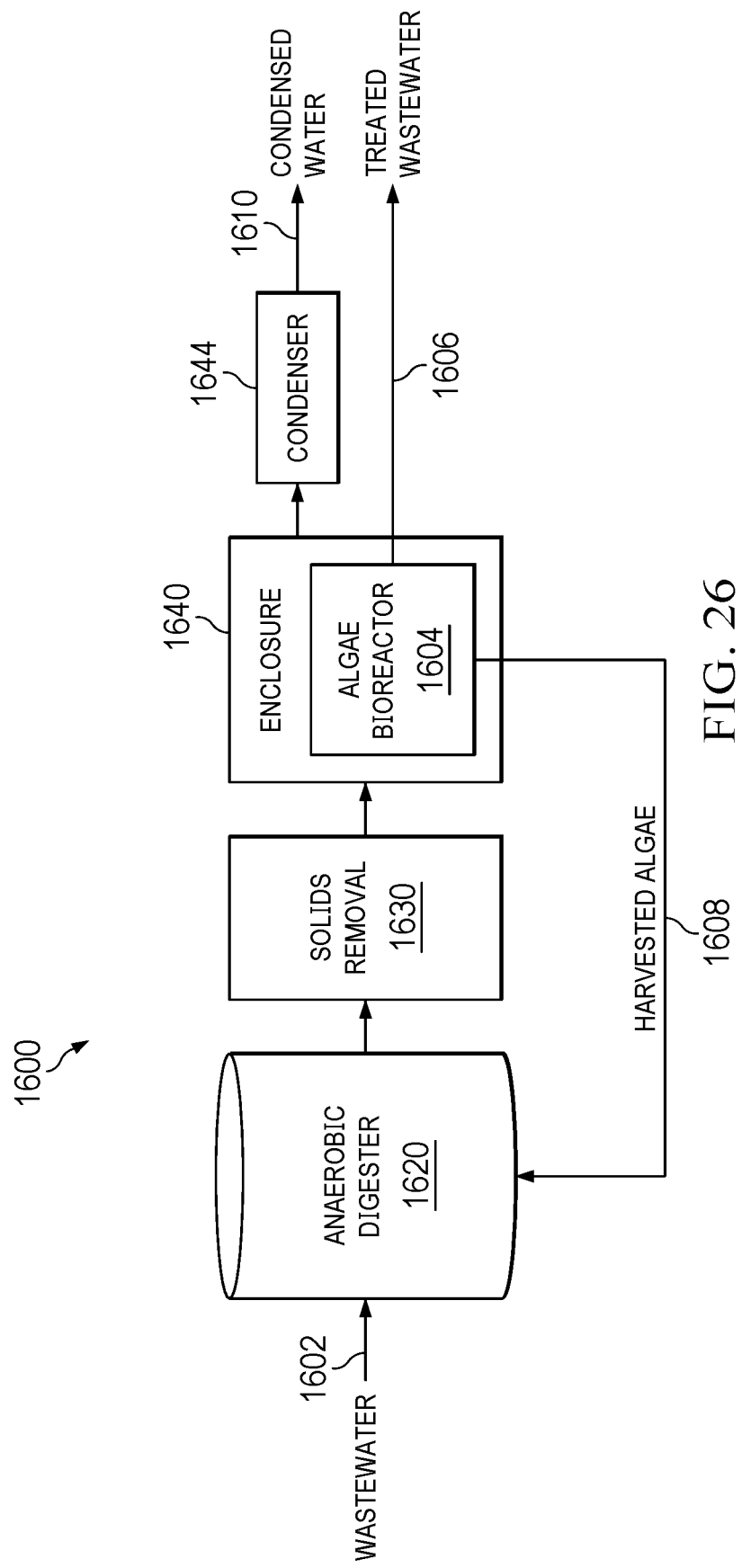
FIG. 26 depicts a plan view of an algae growth system having a photobioreactor with a resource reclamation device on a top portion thereof while also utilizing an integrated anaerobic digester and a solids removal apparatus.

Referring to FIG. 26, an example embodiment of an algal growth system 1600 is shown. System 1600 can be utilized to treat municipal, industrial, and agricultural wastewater 1602. System 1600 utilizes a RAB system 1604 that is modeled after any of the RAB systems disclosed above. Similar to greenhouse 40, algal growth system 1600 will also be contained within a greenhouse 1640 to act as a natural apparatus to assist in the capture of resources produced by the growing process, which will also decrease operational costs associated with operation of system 1600. In one or more embodiments, a resource reclamation device 1644, similar to resource reclamation device 44, is located on a top portion of the greenhouse 1640 to assist in the recapture of the resources produced during the growing process.

In the embodiment shown in FIG. 26, the resource reclamation device 1644 is a condenser which collects condensed water 1610 as a resource. In one embodiment, the condensed water 1610 can be used as water for irrigation, drinking water, or process water. In one embodiment, the condensed water 1610 can be recycled back into the greenhouse 1640 to enrich the growing environment for the algae being produced within the system 1600. Once cycled through the system 1600, the wastewater 1602 will come out as treated wastewater 1606 that can be reused. The RAB system 1604 will also produce algae as in any of the embodiments discussed above, that produced algae can be harvested. The harvested algae 1608 is an additional resource of system 1500.

FIG. 26 also shows algal growth system 1600 utilizing an integrated anaerobic digester 1620 and a solids removal apparatus 1630. A wastewater slurry containing both dissolved and solid biodegradable organics flows into an oxygen-free environment within the anaerobic digester 1620. Under proper time and temperature conditions, anaerobic bacteria that grow within the anaerobic digester 1620 feed on the biodegradable organics, converting the carbon in the organics into a gas mixture consisting of $CH_4$ and $CO_2$ called biogas. The undigested solids, also known as the digestate, exits the anaerobic digester 1620, typically in the form of a slurry with 5% solids. In one or more embodiments, the solids removal apparatus 1630 is a screw press for dairy digesters or a centrifuge for municipal digesters. The solids removal apparatus 1630 then separates the slurry into a sludge "cake" and a liquid stream with low solids (<1%) that becomes the feed to the RAB system 1604. This feed still contains dissolved nutrients and some dissolved organics that grow algae and aerobic bacteria within the RAB system 1604. The RAB system 1604 then grows biomass that is a mixture of both algae (that uses the nutrients, $CO_2$, and water to grow algae) and bacteria (that uses oxygen and organics to grow bacteria), all combined into a semi-slurry stream, the Harvested Algae 1608. As shown, the harvested algae 1608 produced within the RAB system 1604 can then be recycled back into the integrated anaerobic digester 1620 to begin the process again.

Figure 35:
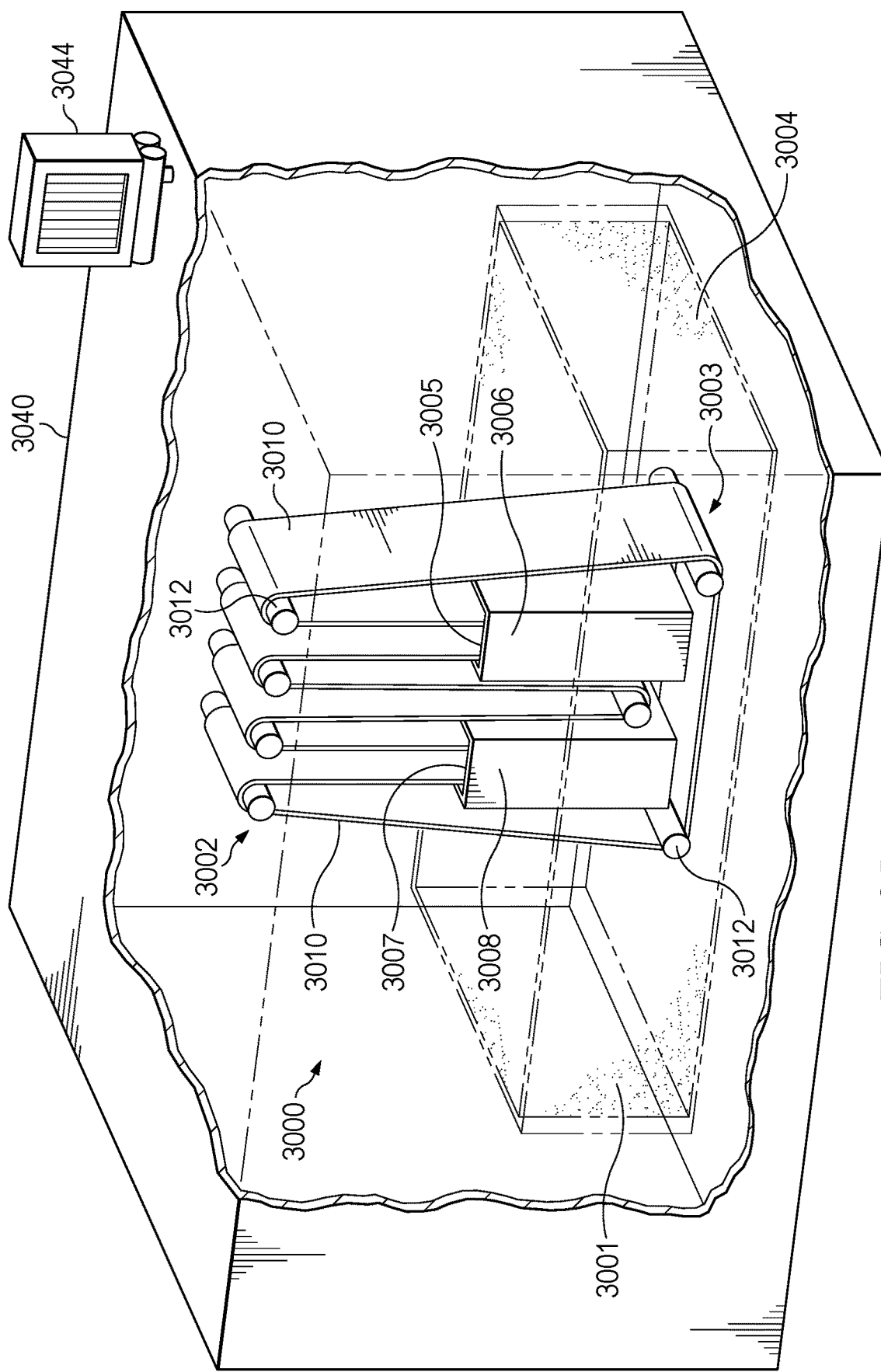
FIG. 35 depicts a perspective view of an algae growth system housed within a greenhouse which utilizes a dual reservoir system.

Referring to FIG. 35, embodiments of the present disclosure also contemplate a system wherein a plurality of reservoirs are utilized within the overall system, similar to those discussed in U.S. Pat. No. 11,339,070, the contents of which are hereby incorporated by reference. Algal growth system 3000 utilizes a revolving algal biofilm photobioreactor 3002 which includes a first liquid reservoir 3004, a second liquid reservoir 3006, and a third reservoir 3008. The photobioreactor 3002 also includes a flexible sheet material 3010 and a plurality of rollers 3012 to rotate the flexible sheet material 3010 through the reservoirs 3004, 3006, and 3008. The photobioreactor 3000 cultivates algae as discussed in any embodiment above. In practice, the algae grown by the photobioreactor 3000 can be utilized to remove a contaminant or pollutant 3001 from the liquid 3003 of the first liquid reservoir 3004.

The liquid 3003 found in the first liquid reservoir 3004 is controlled to have a first condition. The second liquid reservoir 3006 is filled with a second liquid 3005 and the second liquid 3005 is controlled to have a second condition. The algae grown by the photobioreactor 3002 is exposed to the liquid 3003 found in the first liquid reservoir 3004 wherein the algae is exposed to the first condition and the algae uptakes the pollutant 3001 from the liquid 3003 found in the first liquid reservoir 3004. The algae is then removed from the liquid 3003 found in the first liquid reservoir 3004 such that it is exposed to light and air within greenhouse 3040. The algae is then exposed to the second liquid 3005 within the second liquid reservoir 3006 wherein the algae is exposed to the second condition within the second liquid reservoir 3004 and the algae is stimulated to release the pollutant 3001. In one or more embodiments, the system 3000 also includes a third reservoir 3008. In one or more embodiments, the third reservoir 3008 is filled with a third liquid 3007 and the third reservoir 3008 is controlled to have a third condition. In one or more embodiments, the third reservoir 3008 is dry/empty (not shown) and the third reservoir 3008 is controlled to have a third condition. If a third reservoir 3008 is present, it is contemplated that the algae is then removed from the liquid 3005 found in the second liquid reservoir 3006 such that it is exposed to light and air within greenhouse 3040. The algae is then exposed to the third reservoir 3008 wherein the algae is exposed to the third condition within the third liquid reservoir 3008. The addition of a third reservoir 3008 creates the opportunity to enhance the growth of algae. This enhancement could be in the form of conditions that stimulate the growth of traits such as increased lipids, the release of excess nutrients, or the control of inhibiting organisms or conditions to the algae. By increasing the number of the reservoirs, it allows for separate growth enhancements to all occur on the same rotating flexible sheet material 3010. In one or more embodiments, either the first condition, the second condition, or the third condition facilitates growth of a desirable species or consortium of microorganisms, or inhibits growth of an undesirable species or consortium of microorganisms.

In one or more embodiments, the first liquid reservoir 3004 is separate from the other reservoirs that the flexible sheet material 3010 travels through. This allows for the other reservoirs, such as second liquid reservoir 3006, have the amount of the second liquid 3005 therein that is 10 to 1000 times lower in volume than the liquid 3003 found in the first liquid reservoir 3004. In one or more embodiments, the second liquid 3005 can be manipulated to provide delivery of chemicals, vitamins, and conditions directly to the flexible sheet material 3010 without being diluted in the first liquid reservoir 3004. In one or more embodiments, ocean water makes up the first liquid reservoir 3004. The second liquid reservoir 3006 can have targeted delivery of nutrients and vitamins that are usually lacking in ocean water but are required for rapid algae growth. So in this case, the second liquid reservoir 3006 is to supply the algae "food and nutrients" to rapidly grow. The system 3000 also contemplates the use of a resource reclamation device 3044 on or within greenhouse 3040 that is similar to any resource reclamation device described within the body of the present disclosure. Although the above discussion focused on the use of algae, it is also contemplated that other microorganisms, such as bacteria, could be utilized within the system 3000.

Figure 27:
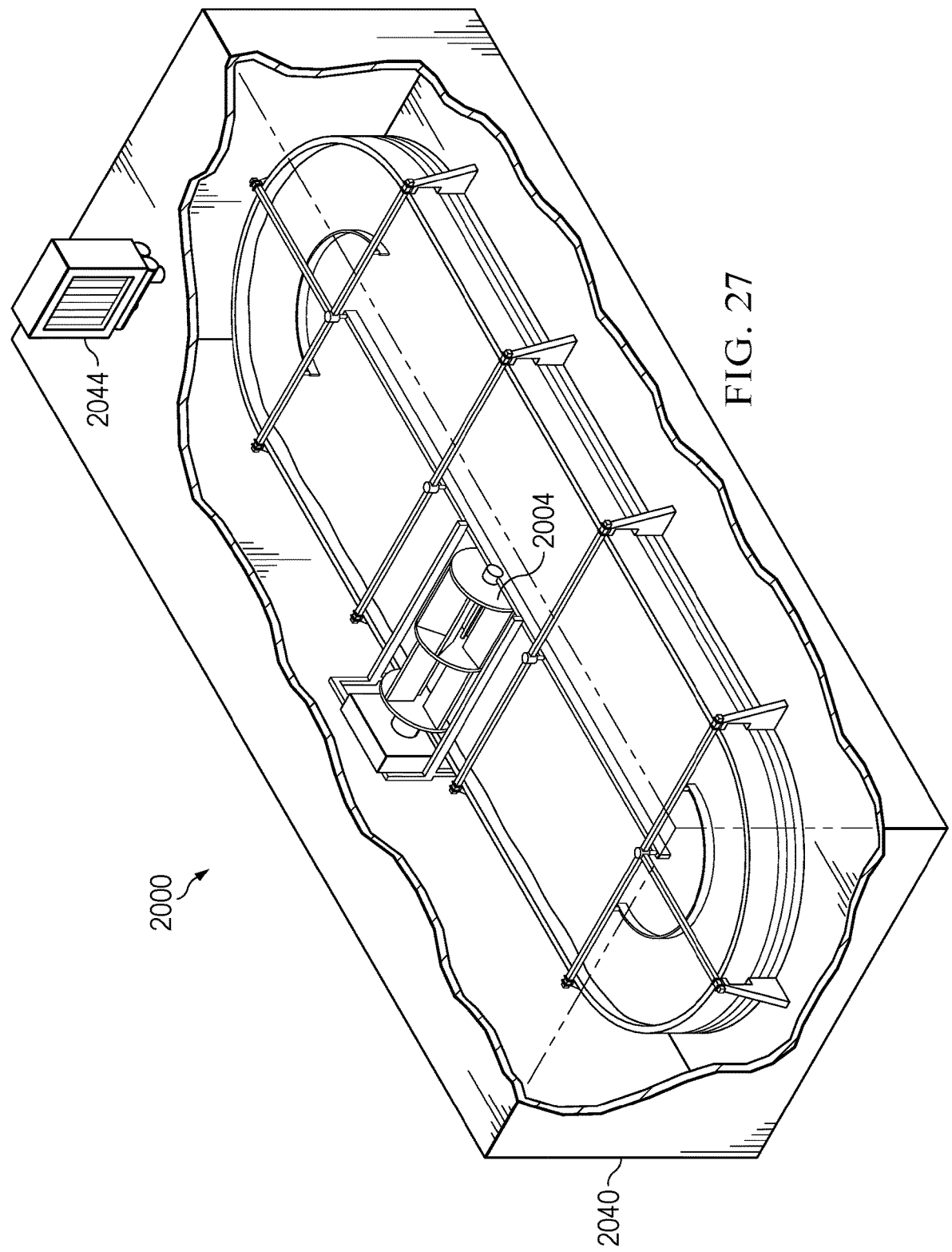
FIG. 27 depicts a partial cutaway perspective view of an algae growth system utilizing an algae wheel system within a greenhouse having a resource reclamation device on a top portion thereof according to one embodiment.

Although all of the disclosed embodiments discussed above disclosed the use of a "belted" type RAB system, other types of RAB systems are also contemplated as being utilized within any of the above disclosed embodiments. Any system that has a high surface area, also known as the gas/liquid interface surface area, which grows biomass such as algae are contemplated. For example, the belted type RAB system could be replaced with an algae wheel system 2004, such as the one shown in the system 2000 shown in FIG. 27. The algae wheel system 2000 will similarly be contained within a greenhouse 2040 with a resource reclamation device 2044, similar to resource reclamation device 44, located on a top portion of the greenhouse 2040 to assist in the recapture of the resources produced during the growing process. Other types of RAB systems contemplated by the present disclosure include static/non-moving type RAB systems.

Although versions described herein use algae as the cultivated biomass, other types of biomass are contemplated for use within the RAB systems of the present disclosure. In one or more embodiments, the biomass utilized within the RAB systems of the present disclosure include algae, bacteria, and microorganisms.

Water Reclamation

A condenser is considered to be any device that converts water vapor to liquid water. In most instances, this is done by reducing the water temperature (and sometimes pressure) below its dew point. Condensing liquid is about creating a temperature differential between a solid surface and a gas that contains air. Air located within enclosures of the present disclosure is air that contains the water vapor that the present disclosure is looking to capture. That temperature of the air within the enclosures of the present disclosure will be different than either the water temperature or the outside air temperature. This delta in temperature will be the driving force of the system utilized to capture water vapor from the atmosphere within the enclosures of the present disclosure. For example, often at night, the temperature outside of the enclosures of the present disclosure will drop much faster than the air inside the enclosures. As such, the outside air can be pumped through a resource reclamation device, such as a condenser, to capture the water vapor within the air inside the enclosure. In another example, a cool influent water, such as seawater, could be used to cool the condenser and capture the water vapor within the air inside the enclosure.

An air-conditioning compressor will remove water vapor within the air inside the enclosure when said air has a high humidity. A chiller will allow for the air from within the enclosure to flow through it with a refrigerant on the other side of the surface to remove water vapor within the air inside the enclosure.

In one embodiment, the resource reclamation device 44 is a condenser, such as a finned condenser. The condenser 44 works by capturing the water released by the algae into the greenhouse 40 by evaporation. The roof and walls of greenhouse 40 will act as condensing surfaces as long as the air outside of the greenhouse 40 is cooler than the air inside greenhouse 40. In another embodiment, the roof of the greenhouse 40 could also utilize a cooling system (not shown) to maintain a constant condensing surface temperature. After the air is run through the condenser 44 to collect the water vapor, the captured air can then either be released into the environment outside of the greenhouse 40, or it can be re-circulated back within the interior of the greenhouse 40. Along the same lines, the water captured by the condenser 44 can either be recirculated back into the RAB system within the greenhouse 40, or it can be utilized as a source of clean water outside of the greenhouse 40. Such uses could be as a source of water for agricultural or industrial needs, or even as a source of clean drinking water. The condenser 44 will be connected to any suitable piping or water transfer system using appropriate valves, pumps, and/or further treatment steps depending upon its end use.

In one or more embodiments, when the resource reclamation device 44 is a condenser, it is contemplated that after the captured water is taken from the condenser, a post condensation step needs to occur to be sure that the captured water is safe for reuse outside of the RAB system contained within the greenhouse 40. The need for a post condensation step is that other compounds may be captured in the condensate water, such as ammonia or other volatile gases. The post condensation step will make sure that any levels of these other compounds are at safe levels for use outside of the RAB system.

Figure 22:
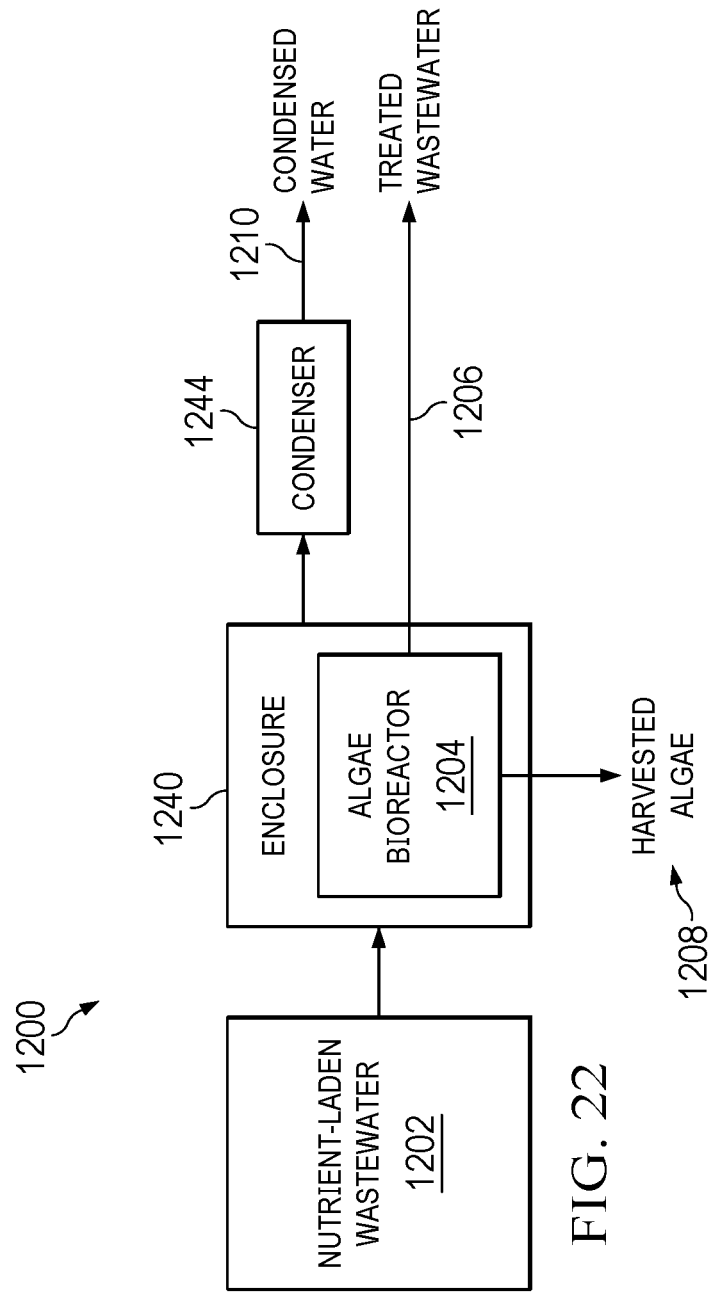
FIG. 22 depicts a plan view of a photobioreactor with a condenser as the resource reclamation device according to one embodiment.

Referring to FIG. 22, an example embodiment of an algal growth system 1200 is shown. System 1200 can be utilized to treat municipal, industrial, and agricultural wastewater 1202. System 1200 utilizes a RAB system 1204 that is modeled after any of the RAB systems disclosed above. Similar to greenhouse 40, algal growth system 1200 will also be contained within a greenhouse 1240 to act as a natural apparatus to assist in the capture of resources produced by the growing process, which will also decrease operational costs associated with operation of the system 1200. In one or more embodiments, a resource reclamation device 1244, similar to resource reclamation device 44, is located on a top portion of the greenhouse 1240 to assist in the recapture of the resources produced during the growing process. In the embodiment shown in FIG. 22, the resource reclamation device 1244 is a condenser which collects condensed water 1210 as a resource. Once cycled through the system 1200, the wastewater 1202 will come out as treated wastewater 1206 that can be reused. The RAB system 1204 will also produce algae as in any of the embodiments discussed above, that produced algae can be harvested. The harvested algae 1208 is an additional resource of system 1200.

Figure 29:
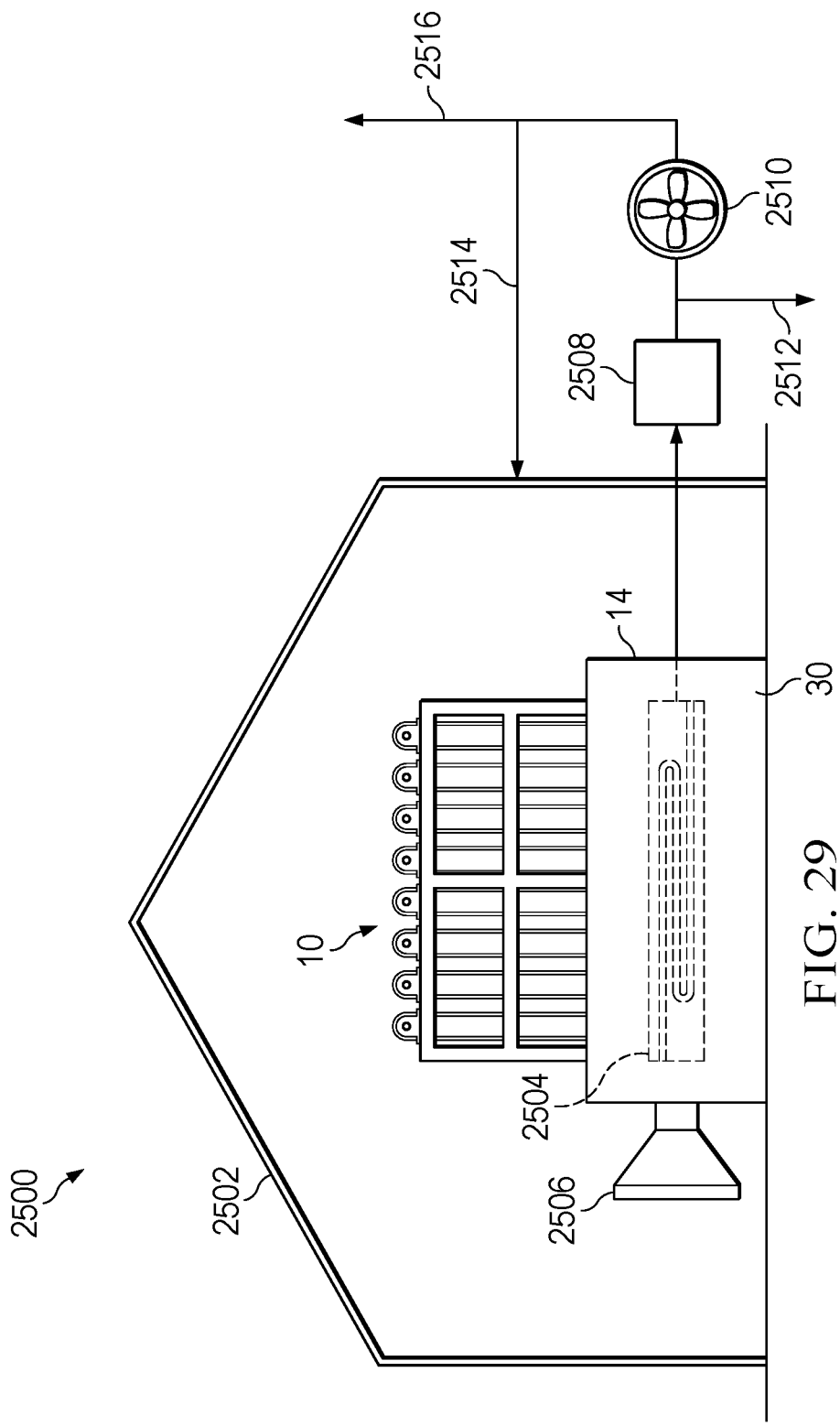
FIG. 29 depicts a perspective view of an algae growth system housed within a greenhouse and having a heat exchanger associated therewith.

The system 2500 as shown in FIG. 29 contemplates any of the RAB systems discussed above, such as RAB 10 similar to the one shown in FIGS. 3, 4, 7, and 8, surrounded by a greenhouse 2502. As shown in FIGS. 3, 4, 7, and 8, RAB 10 includes a liquid reservoir 30 which carries a contacting liquid 14. In one or more embodiments, there is a heat exchanger 2504 located within the liquid reservoir 30. The heat exchanger 2504 will take in the warm air from within greenhouse 2502 through an air intake 2506 and heat the contacting liquid 14. Algae grows faster when grown within a contacting liquid 14 with a temperature near 90° F. Dependent upon the initial source of the contacting liquid 14, it could enter the reservoir 30 at a temperature as low as 50° F., while the air temperature within greenhouse 2502 can be as high as 135° F. Bringing the heat from within greenhouse 2502 into the reservoir 30 benefits the algae growth rate, causes condensation to form, and reduces the overall power demand on the condenser 2508 that will take in air from within the greenhouse 2502 and condensate the water vapor. The air from within greenhouse 2502 will enter the condenser 2508 with assistance of a fan 2510. Water 2512 produced by the condenser 2508 can be sent for further processing as needed. Additionally, the condenser 2508 will produce a form of dry air 2514 which can be returned to the greenhouse 2502 if it is considered to be $CO_2$ enriched, or that dry air can be sent to further processing units 2516 to capture $NH_3$.

Figure 30:
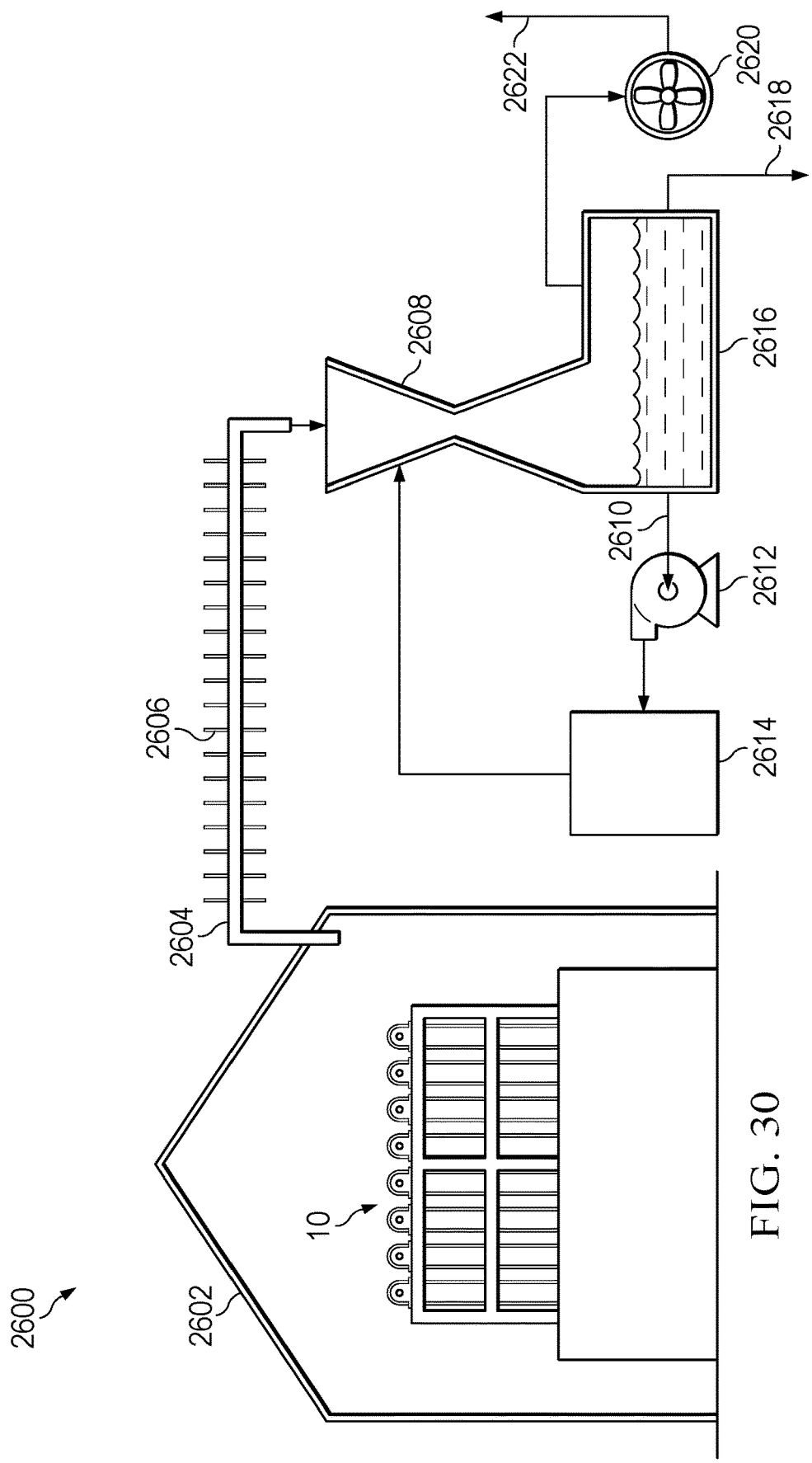
FIG. 30 depicts a perspective view of an algae growth system housed within a greenhouse and having an exhaust system associated therewith to take air out of the greenhouse

The system 2600 as shown in FIG. 30 contemplates any of the RAB systems discussed above, such as RAB 10 similar to the one shown in FIGS. 3, 4, 7, and 8, surrounded by a greenhouse 2602. The system 2600 contemplates the use of an exhaust system 2604 to take air out of the greenhouse 2602 that includes water vapor and $NH_3$ amongst other constituents. In one or more embodiments, the exhaust system 2604 includes thermofans 2606 which help to reduce the temperature of the air exiting the greenhouse 2602 such that more water vapor and condensable gases will be produced. The air from the exhaust system 2604 will be sent to a wet scrubber such as a Venturi scrubber 2608. In one or more embodiments, the Venturi scrubber 2608 includes three sections: a converging section, a throat section, and a diverging section. The inlet gas stream from exhaust system 2604 enters the converging section and, as the area decreases, gas velocity increases. Liquid is introduced either at the throat or at the entrance to the converging section. The inlet gas, forced to move at extremely high velocities in the small throat section, turbulently mixes with the liquid, producing an enormous number of very tiny droplets. Particle and gas removal occur in the diverging section as the inlet gas stream mixes with the fog of tiny liquid droplets. The inlet stream then exits through the diverging section, where it is forced to slow down.

In one or more embodiments, the liquid introduced into the Venturi scrubber 2608 comes from the water produced within the Venturi scrubber 2608. A portion 2610 of the formed water will exit the scrubber 2608 through a spray nozzle 2612 and will enter a water coolant device 2614 before being introduced back into the top of scrubber 2608. A second portion 2616 of the formed water will remain within the scrubber 2608, while a third portion 2618 of the formed water can be used directly as liquid fertilizer as it will be ammonia rich. A fan 2620 will force the dry and clean air to a secondary exhaust system 2622.

Heat Recovery

In one or more embodiments, waste heat recovered from sources external to the greenhouses discussed above can be used in order to operate the RAB systems discussed above under optimum temperature conditions. Available waste heat from external waste sources will be in the form of a hot gas or hot liquid that will exchange heat with a heat transfer medium such as air, water, or oil via a tube or plate heat exchanger that would then transfer heat to the liquid waste within the RAB system. A blower could also be used to recirculate the air within the greenhouse discussed above through a tube or plate heat exchanger, which will exchange heat with the medium that removed heat from the waste heat source.

Figure 24:
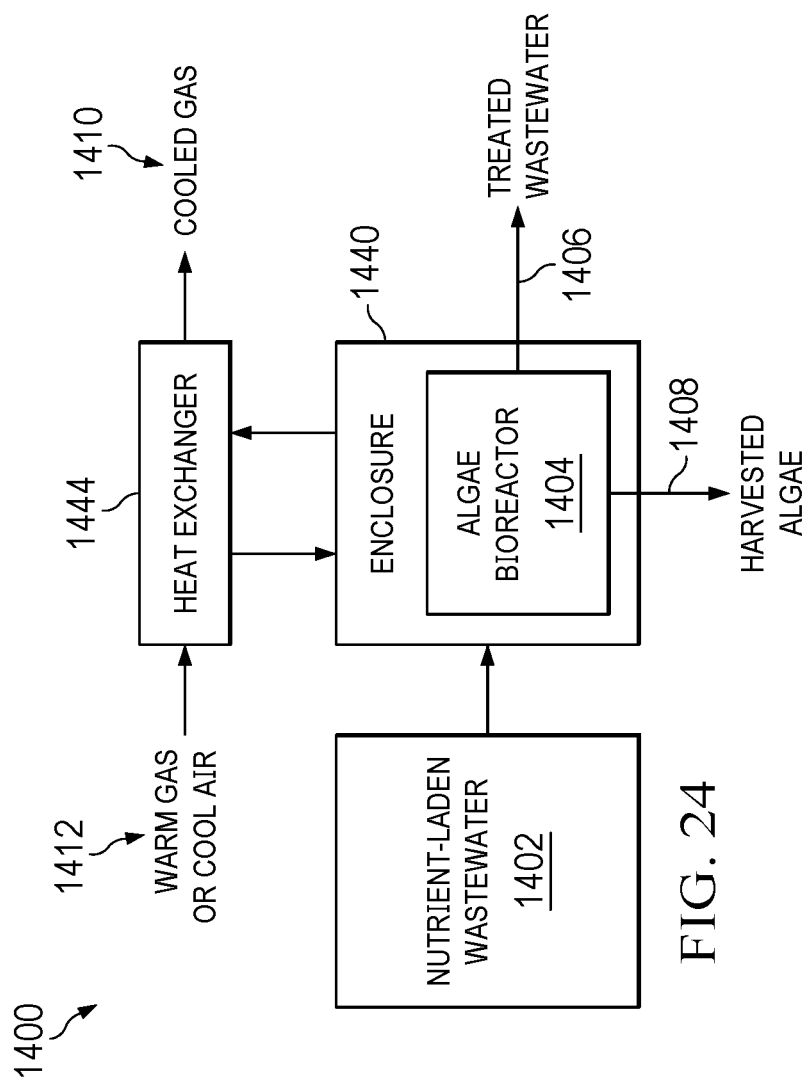
FIG. 24 depicts a plan view of a photobioreactor with a heat exchanger as the resource reclamation device according to one embodiment.

Referring to FIG. 24, an example embodiment of an algal growth system 1400 is shown. System 1400 can be utilized to treat municipal, industrial, and agricultural wastewater 1402. System 1400 could also be utilized to grow algae utilizing freshwater, saltwater, or brackish water 1402. System 1400 utilizes a RAB system 1404 that is modeled after any of the RAB systems disclosed above. Similar to greenhouse 40, algal growth system 1400 will also be contained within a greenhouse 1440 to act as a natural apparatus to assist in the capture of resources produced by the growing process, which will also decrease operational costs associated with operation of system 1400. In one or more embodiments, a resource reclamation device 1444, similar to resource reclamation device 44, is located on a top portion of the greenhouse 1440 to assist in the recapture of the resources produced during the growing process.

In the embodiment shown in FIG. 24, the resource reclamation device 1444 is a heat exchanger which captures heat produced within the greenhouse 140 as a resource. In one embodiment, the resource heat collected within system 1300 can be recycled back into the greenhouse 1440 to enrich the growing environment for the algae being produced within the system 1400. The heat exchanger 1444 can also take the resource heat and produce a source of cool air 1410 that can be utilized in other downstream processes.

The heat exchanger 1444 can remove heat from the greenhouse 1400 and replace it with a cooler gas, such as simply the air outside of the greenhouse or an actively chilled gas. The heat exchanger 1444 can also take in warm air from a source outside the greenhouse 1400 and provide it within the greenhouse 1400 during the colder winter months if the temperature within the greenhouse 1400 needs raised.

Once cycled through the system 1400, the wastewater 1402 will come out as treated wastewater 1406 that can be reused. The RAB system 1404 will also produce algae as in any of the embodiments discussed above, that produced algae can be harvested. The harvested algae 1408 is an additional resource of system 1400. It is also contemplated that additional upstream processes from the RAB system 1404, such as an anaerobic digester, can produce excess heat or cool air 1412. Additionally, the natural environment that the system 1400 is placed within can produce an additional source of hot or cold air, and that hot or cold air can also be captured by the heat exchanger 1444. This upstream and environmental air 1412 can also be recycled back into the greenhouse 1440.

In one embodiment, the biogas produced within the system can be burned, which will generate heat, which can be captured, either by sending the stack gas directly into the greenhouse 1440, exchanging stack gas heat with air entering or recirculating within the greenhouse 1440, exchanging heat with wastewater 1406 entering the enclosure, or a combination of the above.

Gas/Ammonia and $CO_2$ Recovery

In one or more embodiments, RAB systems of the present disclosure produce ammonia that volatizes from the RAB system running and producing algae. In such embodiments, the present disclosure can optionally be set up to remove the produced ammonia gas from within the enclosure, such as greenhouse 40. The removal of ammonia from the environment of greenhouse 40 can be accomplished through methods such as, but not limited to, biological treatment, biofiltration treatment, air/steam stripping, supercritical water oxidation, break-point chlorination, chemical precipitation, and ion exchange and adsorption.

Ammonia evaporated during the algae drying process can be recovered by sending the dryer off gas to any of the ammonia recovery processes discussed above, and in one or more embodiments, it can be combined with the moist air from within the greenhouse. In one or more embodiments, an acid scrubber is utilized and a fan will recirculate moist air through the scrubber that will convert gaseous ammonia into an ammonium salt. In one or more embodiments, a condenser is used and a fan will recirculate moist air through the condenser to first remove water, then the air will travel to a low temperature chiller to condense the ammonia as anhydrous ammonia. In one or more embodiments, an ammonia adsorbent media is used (such as regenerable ion exchange resins, activated carbon, or biochar). A fan will recirculate moist air through the adsorbent media. If the adsorbent media is a resin, it can eventually be regenerated with an acid to produce $(NH_4)SO_4$ and if the adsorbent media is activated carbon or biochar, it can be regenerated with hot air followed by chilling to produce anhydrous ammonia.

In one or more embodiments, carbon dioxide recovered from sources external to the greenhouses discussed above can be used in order to operate the RAB systems discussed above under optimum growing conditions. Gas containing carbon dioxide collected from an external source can be bubbled into the contacting liquid within reservoir systems of the RAB systems discussed above by using a blower and a gas distributor. The contacting liquid can be pumped to a gas scrubber used to remove carbon dioxide from the mixed gas stream and then the contacting liquid can be returned to the reservoir. In other embodiments, gas containing carbon dioxide collected from an external source can be fed directly into the greenhouse, controlled with carbon dioxide monitors to assure the optimum greenhouse carbon dioxide concentrations.

Figure 23:
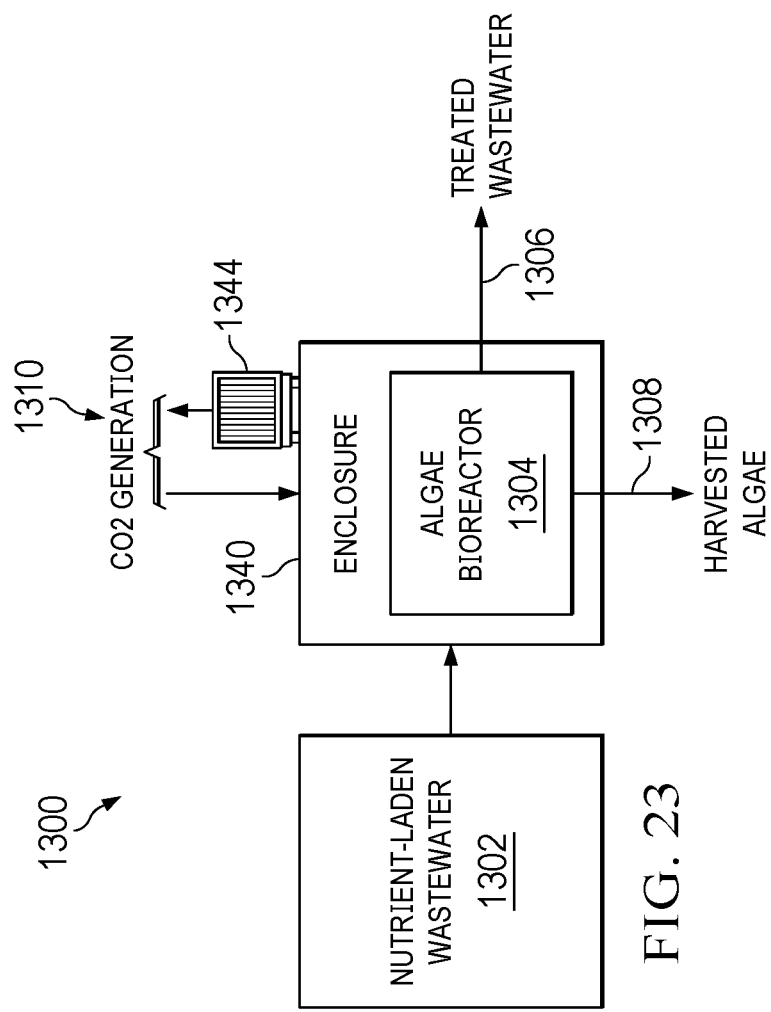
FIG. 23 depicts a plan view of a photobioreactor with a $CO_2$ capturing reclamation device according to one embodiment.

Referring to FIG. 23, an example embodiment of an algal growth system 1300 is shown. System 1300 can be utilized to treat municipal, industrial, and agricultural wastewater 1302. System 1300 utilizes a RAB system 1304 that is modeled after any of the RAB systems disclosed above. Similar to greenhouse 40, algal growth system 1300 will also be contained within a greenhouse 1340 to act as a natural apparatus to assist in the capture of resources produced by the growing process, which will also decrease operational costs associated with operation of the system 1300. In one or more embodiments, a resource reclamation device 1344, similar to resource reclamation device 44, is located on a top portion of the greenhouse 1340 to assist in the recapture of the resources produced during the growing process. In the embodiment shown in FIG. 23, the resource reclamation device 1344 is a direct air capture device which collects $CO_2$ 1310 as a resource.

Embodiments of the present disclosure produce "biogas", that is typically 50% $CO_2$ and 50% methane ($CH_4$) by volume. The produced biogas can be utilized in a flare, engine, turbine, or high temperature fuel cell to produce a stack gas containing $CO_2$. If then burned with air, the gas will be roughly 80% nitrogen and 20% $CO_2$. However, if utilized in a fuel cell, the $CO_2$ purity will be close to 100%. The methane and $CO_2$ can also be separated, usually utilizing a pressure swing adsorption (PSA) method or by the use of membranes. The $CO_2$ collected after separation is close to 100% pure.

In one embodiment, the resource $CO_2$ 1310 that is collected within system 1300 can be recycled back into the greenhouse 1340 to enrich the growing environment for the algae being produced within the system 1300. Once cycled through the system 1300, the wastewater 1302 will come out as treated wastewater 1306 that can be reused. The RAB system 1304 will also produce algae as in any of the embodiments discussed above, that produced algae can be harvested. The harvested algae 1308 is an additional resource of system 1300. It is also contemplated that additional upstream processes from the RAB system 1304, such as an anaerobic digester, can produce $CO_2$. This upstream $CO_2$ that is produced can also be recycled back into the greenhouse 1340, or it can be utilized to produce renewable gas or stack gas from combustion of carbon-based fuels.

Figure 31:
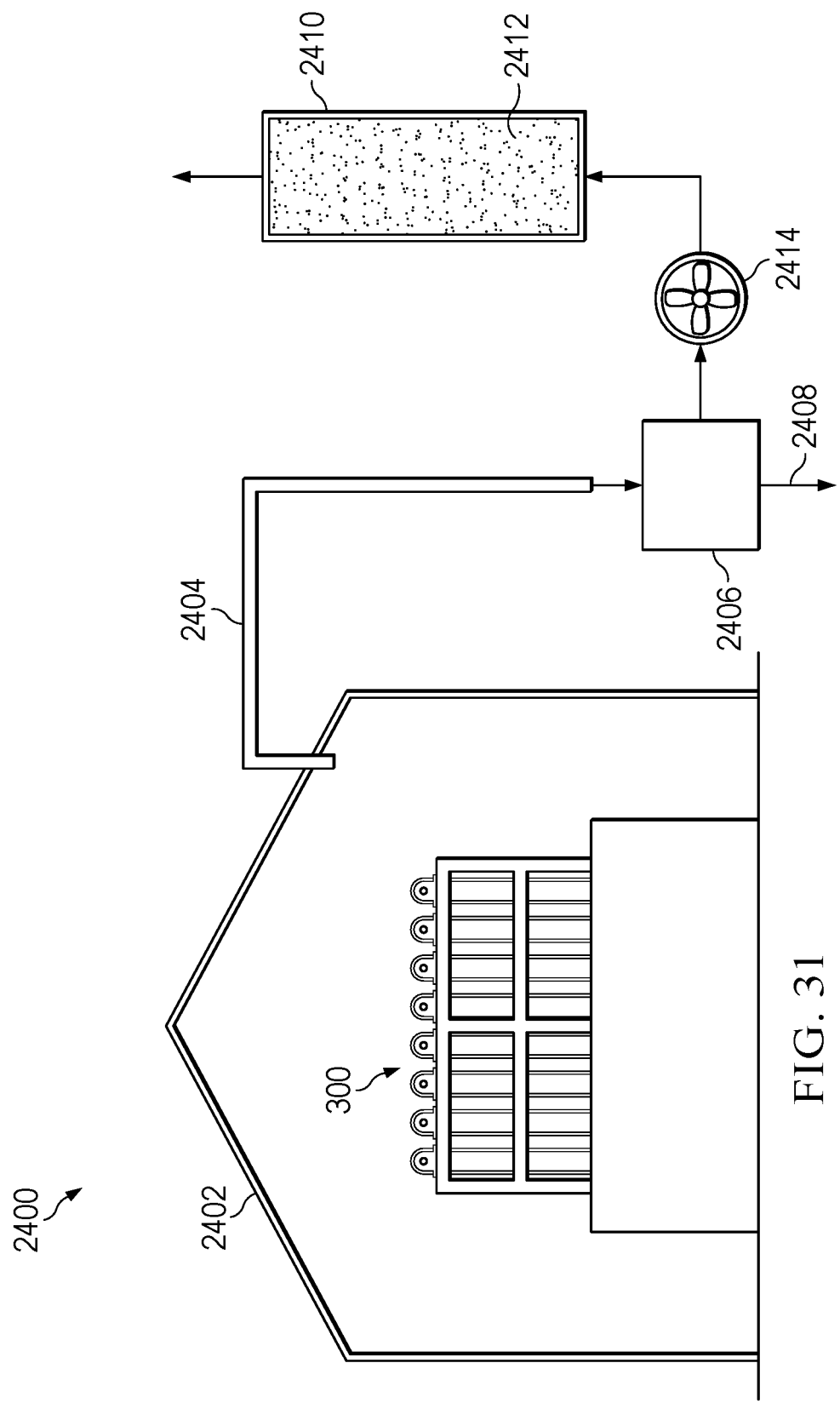
FIG. 31 depicts a perspective view of an algae growth system housed within a greenhouse and having an ammonia capture device associated therewith.

The system 2400 as shown in FIG. 31 contemplates any of the RAB systems discussed above, such as a photobioreactor 300 similar to the one shown in FIGS. 14-16, surrounded by a greenhouse 2402. System 2400 includes an apparatus 2404 to capture the air from within greenhouse 2402. In one or more embodiments, apparatus 2404 is selected from the group consisting of ducting, pipes, or other apparatuses to convey gases and vapors to the water separation device 2406. The air captured by apparatus 2404 will include at least water vapor and ammonia. The air captured by apparatus 2404 will travel to a water separation device 2406. In one or more embodiments, water separation device 2406 is selected from the group consisting of a condenser, chiller, compressor, or any other apparatus disclosed in the present disclosure that allows for the capture and removal of water vapor from the humid air within greenhouse 2402. Water separation device 2406 will separate the water vapor from the air via a temperature differential and/or a pressure differential. The reclaimed water 2408 from water separation device 2406 can be used directly once reclaimed or in other embodiments, it can be sent for further treatment. Once the air travels through water separation device 2406, it will travel to an ammonia capture device 2410. In one or more embodiments, ammonia capture device 2410 includes an absorption media 2412. In one or more embodiments, absorption media 2412 is selected from biochar or activated charcoal. In one or more embodiments, the absorption media 2412 may require acid impregnation or other chemical treatments to increase ammonia absorption efficiency. In one or more embodiments, spent absorption media 2412 may be regenerated or utilized as an additive in an algae based produce such as turf grass fertilizer. A fan 2414 can be utilized to drawn the air through both apparatus 2404 and ammonia capture device 2410.

Enclosure Improvements

In one or more embodiments, any of the enclosures disclosed above could contain fins on the enclosure structure itself which will allow for the condensed water on the enclosure panels to pool into a central collection area close to a reclamation device. In one or more embodiments, any of the enclosures disclosed above should be made of a material that allows for sufficient light to pass through in order to deliver the necessary light needed to grow the algae. Such materials includes polycarbonate or glass. In one or more embodiments, any of the enclosures disclosed above should be designed with a roof and walls that allow for condensation of water from the enclosure air and to allow that water to flow down the walls of the enclosure to a common drain.

Figure 28:
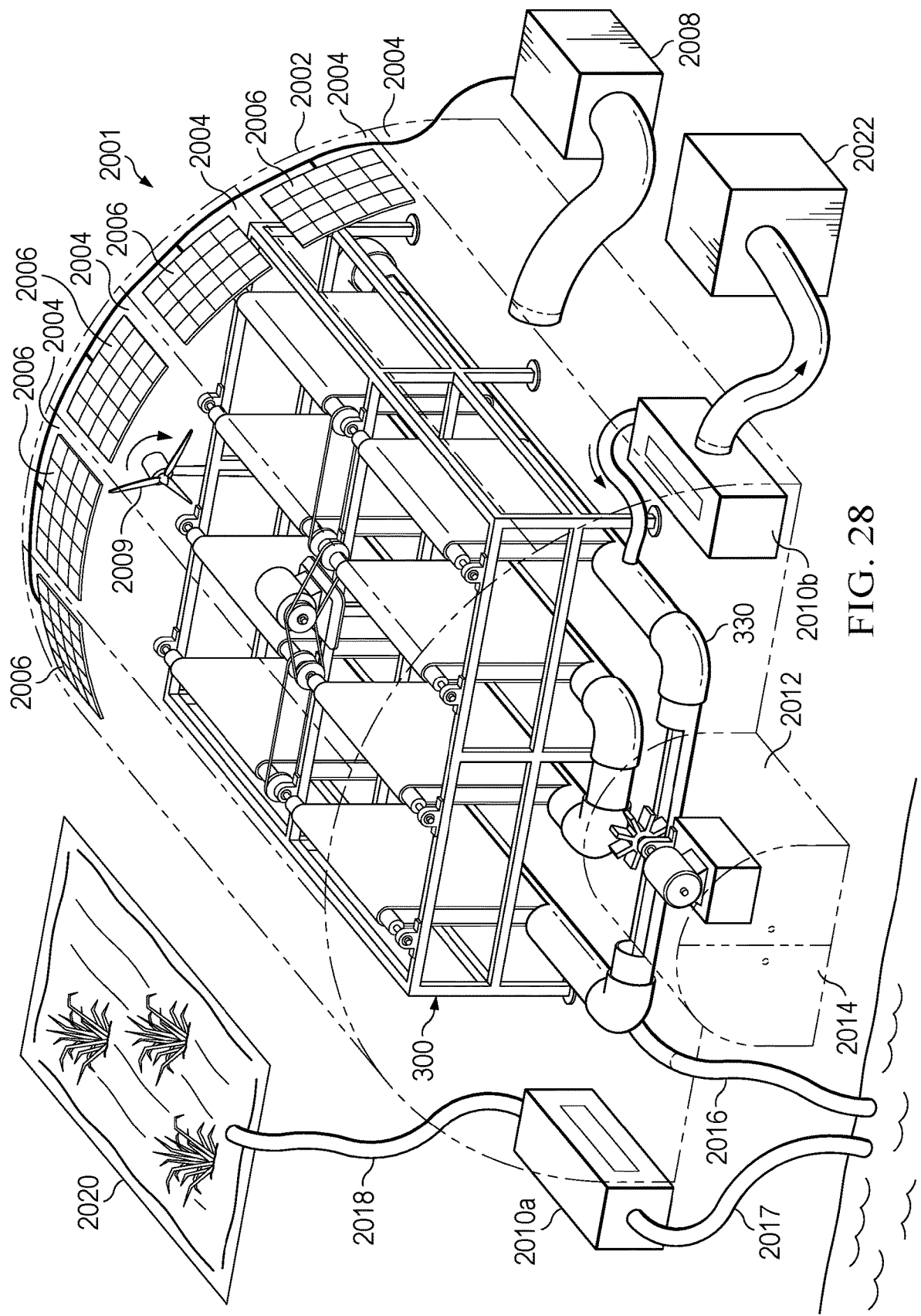
FIG. 28 depicts a perspective view of a revolving algal biofilm bioreactor having an associated algal growth system, a trough system, and a resource reclamation device on a side portion of an air dome according to one embodiment.

Although the embodiments above describe and show a greenhouse that is a rigid structure, it is also contemplated that the RAB systems disclosed above could be contained within an air dome 2001, bio-dome, or the like such as the one shown in FIG. 28. An air dome refers to an area covered by a sheet that is anchored to the ground and filled with pressurized air. Such designs can be lightweight and portable to facilitate easy setup and movement of the system. Any inflatable or partially inflatable setup is contemplated. Systems can also include a tent-like arrangement using tension, wiring, or other supports to maintain an enclosure.

In one or more embodiments, the sheet or suitable sheet material 2002 is transparent. Embodiments of the present disclosure contemplate utilizing an air dome or bio-dome made from a fabric, plastic, glass, or other suitable material that allows for sufficient light to pass through in order to deliver the necessary light needed to grow algae or other biomass such as by a photobioreactor 300 similar to the one shown in FIGS. 14-16. It will be appreciated that the material can be uniform in design, shape, and transparency, or can vary by section such that certain areas are opaque, transparent, or semi-transparent. Portions of the material can include filters, insulators, or other features to facilitate growth within the bio-dome. In one version the structure is divided into panels 2004 that can be adjusted or angled to provide for light optimization. It will be appreciated that such structures can have different modes for different climates or times of day. The structure can include multiple layers, such as a covering for the evening that is removable during the day, where such coverings or layers can be manual or automatically adjusted. Retractable blinds, shades, and the like are contemplated. It is contemplated that grow lights can be incorporated into the system where the structure is opaque, for example, or to supplement natural light permeating the enclosure. Additional features like grow lights may be powered by renewable energy systems, such as solar panel 2006 associated with the air dome 2001 as described herein.

Embodiments that incorporate a dome can include one or more blower unit(s) 2008 in order to keep the air dome 2001 inflated. The one or more blower unit(s) 2008 can be positioned at any suitable location within the air dome 2001 or any location external to the air dome 2001, such as shown in FIG. 28. The one or more blower unit(s) 2008 and can be powered by AC or, for example, by the solar panels 2006 associated with the air dome 2001 or other renewable energy sources. The one or more blower unit(s) 2008 and or fans 2009 can also assist in pushing high humidity air towards one or more condenser(s) 2010 located adjacent to, within, or on the top surface of the air dome 2001. Similar to a greenhouse, the air dome 2001 can have an increased carbon dioxide concentration relative to the atmosphere, which may improve the growth rate of the algae grown by the photobioreactor 300. The air dome 2001 also acts a natural enclosure to assist in the capture of evaporated water produced by the growing process. Various features of the structure can cooperate for the conservation of resources including moisture, gasses, heat, etc. The overall shape of the air dome 2001 can be designed to further funnel, collect, or otherwise direct air flow in a particular direction. For example, the one or more blower unit(s) 2008 can force air into a smaller area near the one or more condenser(s) 2010 to facilitate condensation, water reclamation, or the like. Positive pressure associated with the one or more blower unit(s) 2008 may also improve condensation and other environmental factors.

The system of FIG. 28 shows an entrance way 2012 into the air dome 2001, along with two separate condenser units 2010 utilized to capture the evaporated water produced by the growing process of the photobioreactor 300. Any suitable condenser or heat exchanger is contemplated and the one or more condenser units 2010 can be positioned at any suitable location within or outside of the air dome 2001. For example, a condenser unit 2010 may be positioned in the natural airflow of high humidity air as part of the fluidic design of the air dome 2001.

It is contemplated that the air dome 2001 may, in at least one version, be periodically or entirely inaccessible by humans. Opening and closing the door 2014 of the entrance way 2012 may allow humid air to escape, diminishing condensation such that a fully enclosed, self-contained air dome 2001 may be allowed to operate uninterrupted or largely uninterrupted. Portions of the enclosure may be accessible whereas other areas that do not require human intervention can be sealed and/or inaccessible. The entrance way 2012 can include an airlock or other measures to permit egress and ingress of individuals without negatively impacting the internal environment of the air dome 2001.

The photobioreactor 300 within the air dome 2001 of FIG. 28 can be utilized to treat municipal, industrial, and agricultural wastewater pumped into the air dome 2001 through a water entrance pipe 2016, and the water captured by the condenser units 2010 will be cleaner than the wastewater that entered the system, and can therefore safely be used in reuse applications. Such an external water source can also be used a source of coolant 2017 within the condenser units 2010 associated with the photobioreactor 300. Condensation is encouraged by providing a heat differential and, where natural occurring water sources are available, the system can utilize this cooler water to facilitate condensation within the air dome 2001. Such systems may also use a natural pressure differential or flow of liquid to move the fluid through the system unaided or with less reliance on pumps or the like.

In one or more embodiments, a first condenser unit 2010*a* can utilize the captured water to send clean water through a water exit pipe 2018 to irrigate crops 2020 situated close to the air dome 2001 of FIG. 28; and a second condenser unit 2010*b* can utilized the captured water to be a source of drinking water 2022. It will be appreciated that the system can utilize any fluid inputs and that the outputs will be cleaner, even more potable, relative to the input fluid. Cleaner water may be a useful byproduct for agriculture or drinking water uses especially in isolated communities.

The system shown in FIG. 28 can be an OEM fully integrated system where a trough system 330 is integral with the air dome 2001. Such a system may be designed to be easily compact or foldable for transportation. In an alternate embodiment, the system can be modular and allow for interchangeability of various power sources, blowers, RAB systems, etc. Such a modular system can allow for a single chassis or base design to be used while adjusting certain aspects for environment, biomass, power source, etc. In yet another example, the enclosure may be a retrofit system that can be used with any suitable existing raceway, RAB, or the like. Such a retrofit system can turn a basic bioreactor system into a one that recycles one or a plurality of different resources.

Figure 32:
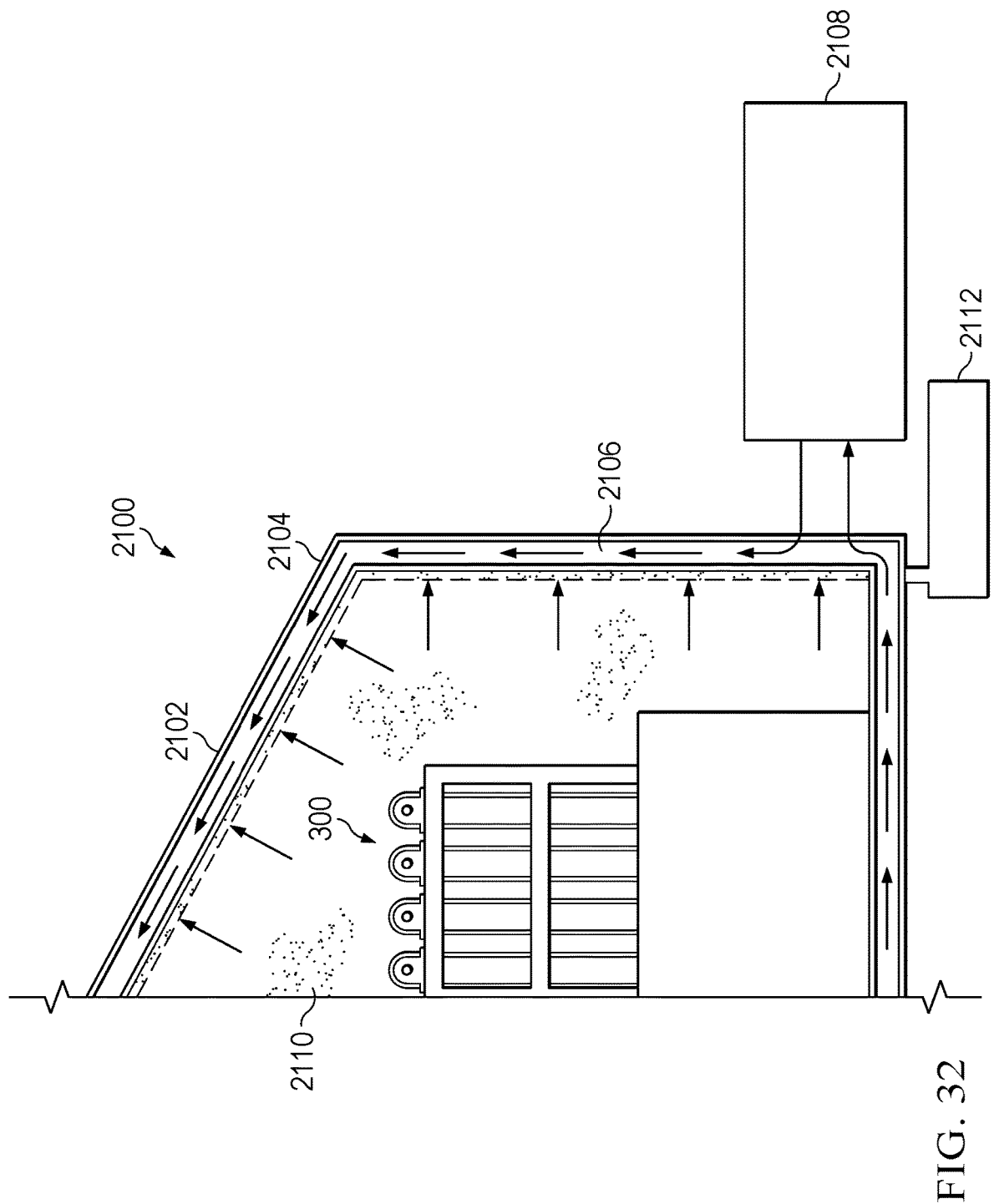
FIG. 32 depicts a perspective view of an algae growth system housed within a greenhouse wherein the greenhouse includes structural framing having a chilled fluid conveyed through the structural framing.

The system 2100 as shown in FIG. 32 contemplates any of the RAB systems discussed above, such as a photobioreactor 300 similar to the one shown in FIGS. 14-16, surrounded by a greenhouse 2102. Greenhouse 2102 is contemplated to include structural framing 2104. Structural framing 2104 is made from a tube structure that has a chilled fluid 2106 being conveyed through the structural framing 2104. The chilled fluid 2106 is produced and forced through the tube structure of the structural framing 2104 by an apparatus for of producing and pumping chilled fluid 2108. The chilled fluid 2106 will allow the structural tubing 2104 to experience a temperature drop. This reduced temperature allows for the structural framing 2104 to create a localized point below the dew point, which will cause water vapor 2110 to condense on the inner surface of the structural frame 2104. The system 2100 of FIG. 32 will also include an apparatus 2112 of capturing the condensed water. In one or more embodiments, apparatus 2112 is an integrated gutter/trough system.

Power Systems

In one or more embodiments, the resource reclamation device 44 can be powered from AC supplied via a grid, or through AC/DC power supplied via a renewable energy source, such as solar power.

FIG. 28 shows how the enclosures used to house the RAB systems, such as a greenhouse or air dome, can draw on solar panels 2006 to power the RAB systems. Any suitable power source, such as renewable power from wind or hydroelectric, can be used to sustainably power the system described herein. Solar panels, windmills, or turbines can be associated with the enclosure and a single enclosure can be constructed to modularly accept a variety of different power options. For example, when using solar as a power source, certain panels of the dome may be interchangeable to allow for solar arrays or the like. The power source can be electrically coupled to a battery for storage, a generator, or directly to for example a blower used to inflate the dome. Excess power generated by such systems can also be usable outside of the system, such as via an external outlet, particularly in remote areas.

Figure 33:
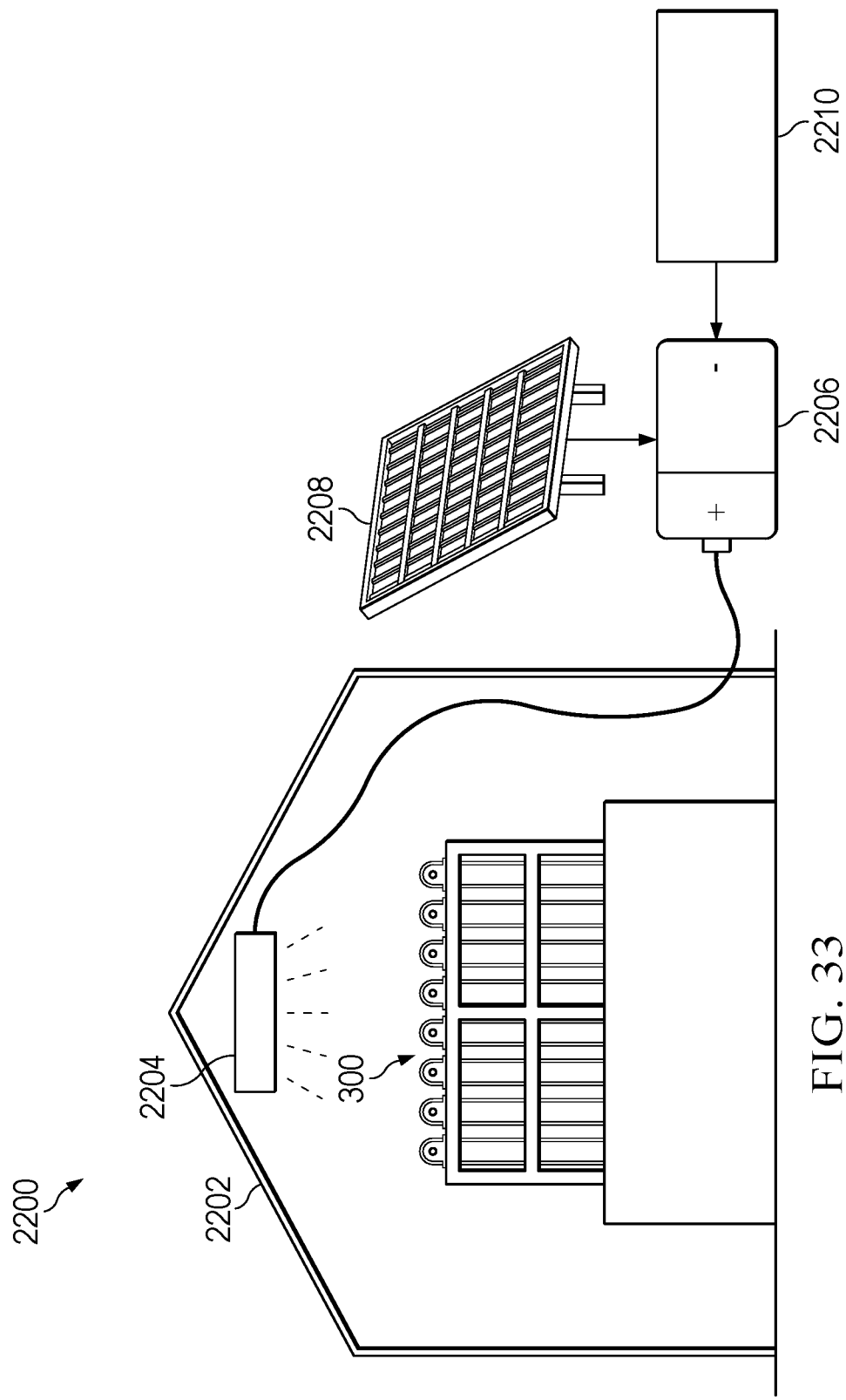
FIG. 33 depicts a perspective view of an algae growth system housed within a greenhouse utilizing grow lights powered by an energy source.

The system 2200 as shown in FIG. 33 contemplates any of the RAB systems discussed above, such as a photobioreactor 300 similar to the one shown in FIGS. 14-16, surrounded by a greenhouse 2202. System 2220 utilizes grow lights 2204 that are powered by an energy source 2206 which is powered by a solar array 2208 and/or a waste heat energy generator 2210. The use of grow lights will increase the hours of "daylight" in which the algae within photobioreactor 300 can grow. This increased amount of growing time will result in more carbon, nitrogen, and phosphorous being produced, which will also lead to an increase in the heat produced within greenhouse 2202. This increase in heat production will allow for more heat to be captured by the waste heat energy generator 2210 which can be used to produce energy stored within the energy source 2206.

Figure 34:
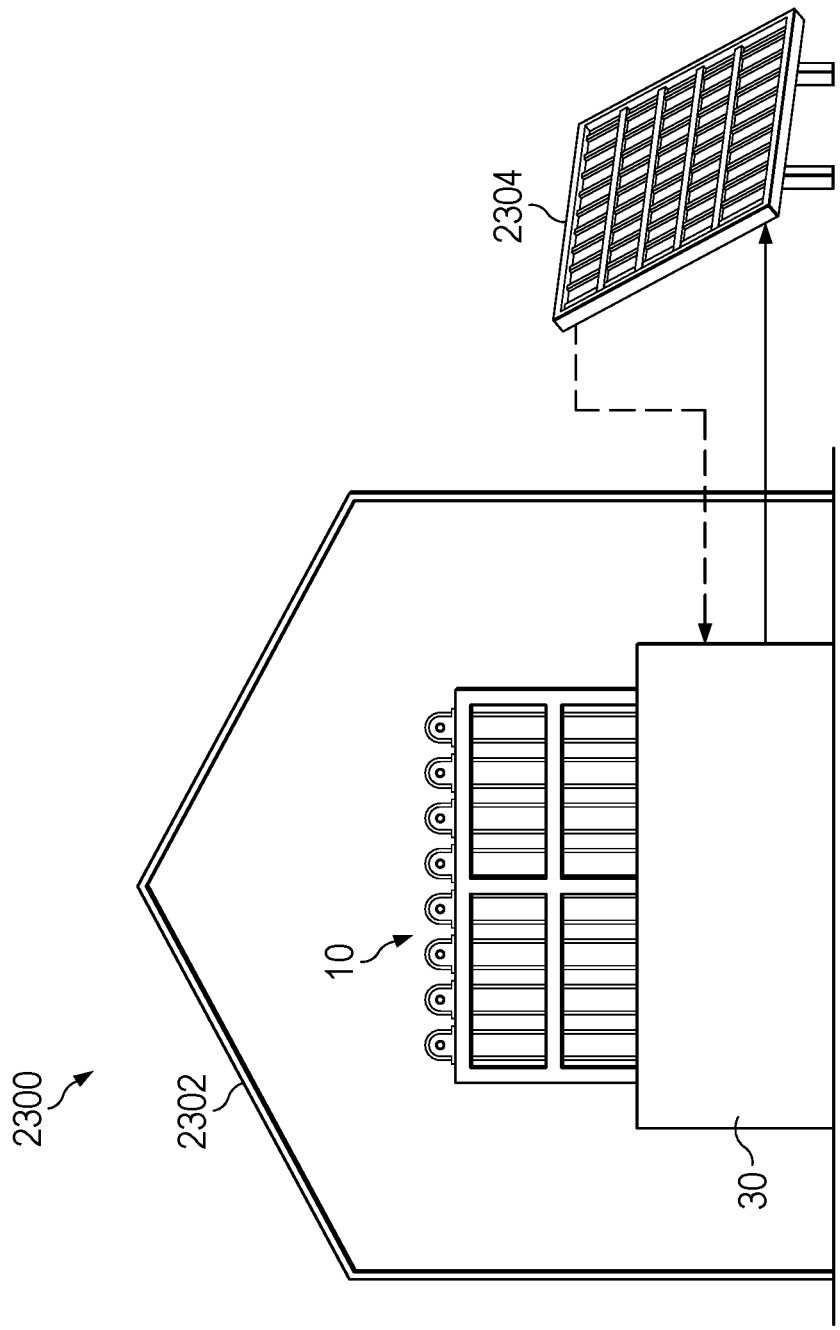
FIG. 34 depicts a perspective view of an algae growth system housed within a greenhouse wherein the liquid source of the algae growth system is heated by a solar powered water heater.

The system 2300 as shown in FIG. 34 contemplates any of the RAB systems discussed above, such as RAB 10 similar to the one shown in FIGS. 3, 4, 7, and 8, surrounded by a greenhouse 2302. As shown in FIGS. 3, 4, 7, and 8, RAB 10 includes a liquid reservoir 30 which carries a contacting liquid 14. The temperature of the contacting liquid 14 has a large impact on the algae growth rate within RAB 10. Algae grows best at about 90° F., at about this temperature the algae is best situated to capture the most carbon, nitrogen, and phosphorus. However, keeping the contacting liquid at this temperature can be difficult in cooler climates. Therefore, in one or more embodiments, a solar powered water heater 2304 is utilized in concert with the liquid reservoir 30. By increasing the temperature of the contacting liquid 14, it will also increase the volatilization of ammonia. Therefore, in one or more embodiments, an ammonia gas capture system (not shown) is coupled to system 2300.

Systems described herein can utilize one or more air circulating systems, such as one or a plurality of fans 2009 as shown in FIG. 28, within the enclosure. The increased circulation may have numerous benefits including movement of high humidity air towards the condenser and increasing evaporation off of the surface of the RAB. The enclosure can include other features, such as baffles or directional features, to encourage air flow around, for example, the vertical bioreactors. Airflow speed and direction can be consistent, can be modified manually, or can be adjustable via an algorithm to depending on growth cycle, time of day, or the like.

In one or more embodiments, the algae formed within the systems disclosed above can have lipids removed therefrom, and those lipids can be used to produce biomethane that can serve as an onsite fuel source to power any of the elements disclosed above.

In various embodiments disclosed herein, a single component can be replaced by multiple components and multiple components can be replaced by a single component to perform a given function or functions. Except where such substitution would not be operative, such substitution is within the intended scope of the embodiments.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the present disclosure to be defined by the claims appended hereto.

What is claimed is:

1. An algal growth system comprising:
   a. a flexible sheet material to facilitate growth of a biofilm;
   b. a liquid reservoir configured to retain a contacting liquid in contact with the flexible sheet material;
   c. a mechanism to rotate the flexible sheet material through the contacting liquid;
   d. an enclosure housing the flexible sheet material and the liquid reservoir; and
   e. a resource reclamation device associated with the enclosure, wherein the resource reclamation device is configured to collect and provide a resource for reuse, wherein the resource reclamation device is an exhaust system, wherein the exhaust system removes air from the enclosure; and wherein the system further comprises a wet scrubber operably connected to the exhaust system.

2. The algal growth system of claim 1, further comprising a frame and wherein the flexible sheet material is mounted on the frame in a first mounted geometry, wherein a first height of the first mounted geometry is greater than a first width of the first mounted geometry.

3. The algal growth system of claim 2, wherein the mechanism to rotate the flexible sheet material includes a motor coupled with an actuator system, wherein the actuator system is operably coupled to the first frame, and wherein the motor is operably configured to actuate the actuator system such that the flexible sheet material is actuated.

4. The algal growth system of claim 3, wherein the motor and actuator system are powered through a renewable energy source.

5. The algal growth system of claim 2, wherein the flexible sheet material has a height of between about 500 feet and about 1 foot.

6. The algal growth system of claim 1, wherein a majority of the flexible sheet material is positioned within a gaseous phase and a minority of the flexible sheet material is in contact with the contacting liquid, wherein the mechanism rotates the flexible sheet material through a sunlight capture part in the gaseous phase.

7. The algal growth system of claim 1, wherein the flexible sheet material is selected from the group consisting of cheesecloth, fiberglass, porous PTFE coated fiberglass, chamois, vermiculite, microfiber, synthetic chamois, burlap, cotton duck, velvet, poly-lactic acid, abraised poly-lactic acid, vinyl laminated nylon, polyester, wool, acrylic, lanolin, woolen, cashmere, leather, silk, lyocell, hemp fabric, polyurethane, olefin fibre, polylactide, carbon fiber, and a combination thereof.

8. The algal growth system of claim 1, wherein the flexible sheet material is operably configured to grow algae selected from the group consisting of *Nannochloropsis, Scenedesmus, Haematococcus, Botryococcus, Spirulina, Dunaliella, Arthrospira, Porphyridium, Phaeodactylum, Nitzschia, Crypthecodinium*, and *Schizochytrium*.

9. The algal growth system of claim 1, wherein the enclosure is selected from either a greenhouse or an air dome.

10. The algal growth system of claim 9, wherein the enclosure is a greenhouse and wherein the greenhouse includes structural framing having a chilled fluid conveyed there through.

11. The algal growth system of claim 9, wherein the enclosure is an air dome, and wherein the system further comprises one or more blower units to inflate the air dome.

12. The algal growth system of claim 1, wherein the liquid source is wastewater.

13. The algal growth system of claim 1, wherein the liquid reservoir includes a heat exchanger which will heat the contacting liquid contained within the reservoir.

14. The algal growth system of claim 1, further comprising grow lights and an air circulation system positioned within the enclosure, and wherein the grow lights and air circulation system are powered by a renewable energy source.

15. The algal growth system of claim 1, further comprising an anaerobic digester and a solid removal apparatus operably connected to the enclosure; wherein the anaerobic digester is configured to receive a wastewater slurry, wherein the anaerobic digester is configured to create a digestate from the wastewater slurry, and wherein the solid removal apparatus is configured to receive the digestate and create the contacting liquid therefrom.

16. The algal growth system of claim 1, wherein a maximum percentage of the flexible sheet material that is in contact with the contacting liquid at any point in time is between about 20% and about 0.1%.

* * * * *